(12) United States Patent
Pacek et al.

(10) Patent No.: US 6,915,806 B2
(45) Date of Patent: Jul. 12, 2005

(54) METHOD FOR HARVESTING GRAFT VESSEL

(75) Inventors: James L. Pacek, Coto De Caza, CA (US); Hira V. Thapliyal, Los Altos, CA (US); Philip E. Eggers, Dublin, OH (US)

(73) Assignee: Arthrocare Corporation, Sunnyvale, CA (US)

(*) Notice: Subject to any disclaimer, the term of this patent is extended or adjusted under 35 U.S.C. 154(b) by 229 days.

(21) Appl. No.: 09/771,299

(22) Filed: Jan. 25, 2001

(65) Prior Publication Data

US 2003/0084907 A1 May 8, 2003

Related U.S. Application Data

(63) Continuation-in-part of application No. 09/162,117, filed on Sep. 28, 1998, now Pat. No. 6,117,109, and a continuation-in-part of application No. 09/041,934, filed on Mar. 13, 1998, now Pat. No. 6,391,025, which is a continuation-in-part of application No. 08/990,374, filed on Dec. 15, 1997, now Pat. No. 6,109,268, which is a continuation-in-part of application No. 08/977,845, filed on Nov. 25, 1997, now Pat. No. 6,210,402, which is a continuation-in-part of application No. 08/562,332, filed on Nov. 22, 1995, now Pat. No. 6,024,733, which is a continuation-in-part of application No. 08/485,219, filed on Jun. 7, 1995, now Pat. No. 5,697,281, which is a continuation-in-part of application No. PCT/US94/05168, filed on May 10, 1994, now Pat. No. 5,697,909, which is a continuation-in-part of application No. 08/059,681, filed on May 10, 1993, now abandoned

(60) Provisional application No. 60/182,751, filed on Feb. 16, 2000.

(51) Int. Cl.[7] .............................................. A61B 18/14

(52) U.S. Cl. ........................ 128/898; 606/32; 606/41; 606/48

(58) Field of Search ........................... 128/898; 606/32, 606/41, 48

(56) References Cited

U.S. PATENT DOCUMENTS

2,056,377 A    10/1936    Wappler (Continued)

FOREIGN PATENT DOCUMENTS

| DE | 3930451 | 3/1991 | ........... A61B/17/39 |
| DE | 29609350 | 5/1996 | |
| DE | 19537084 | 4/1997 | |

(Continued)

OTHER PUBLICATIONS

Pearce, John A. (1986) *Electrosurgery*, pp. 17, 69–75, 87, John Wiley & Sons, New York.

(Continued)

*Primary Examiner*—Lee S. Cohen
(74) *Attorney, Agent, or Firm*—John T. Raffle; Richard R. Batt

(57) ABSTRACT

The present invention provides systems, apparatus and methods for selectively applying electrical energy to body tissue in order to incise, dissect, harvest or transect tissues or an organ of a patient. The electrosurgical systems and methods are useful, inter alia, for accessing, dissecting, and transecting a graft blood vessel, such as the internal mammary arteries (IMA) or the saphenous vein, for use in a by-pass procedure. A method of the present invention comprises positioning an electrosurgical probe adjacent the target tissue so that one or more active electrode(s) are brought into at least partial contact or close proximity with a target site in the presence of an electrically conductive fluid. A high frequency voltage is then applied between the active electrode and one or more return electrode(s). During application of the high frequency voltage, the electrosurgical probe may be translated, reciprocated, or otherwise manipulated such that the active electrode is moved with respect to the tissue. The present invention volumetrically removes the tissue at the point of incision, dissection, or transection in a cool ablation process that minimizes thermal damage to surrounding, non-target tissue.

23 Claims, 40 Drawing Sheets

U.S. PATENT DOCUMENTS

| | | |
|---|---|---|
| 3,815,604 A | 6/1974 | OMalley et al. |
| 3,828,780 A | 8/1974 | Morrison, Jr. et al. |
| 3,901,242 A | 8/1975 | Storz |
| 3,920,021 A | 11/1975 | Hiltebrandt |
| 3,939,839 A | 2/1976 | Curtiss |
| 3,970,088 A | 7/1976 | Morrison |
| 4,040,426 A | 8/1977 | Morrison, Jr. |
| 4,043,342 A | 8/1977 | Morrison, Jr. |
| 4,060,087 A | 11/1977 | Hiltebrandt |
| 4,074,718 A | 2/1978 | Morrison, Jr. |
| 4,092,986 A | 6/1978 | Schneiderman |
| 4,116,198 A | 9/1978 | Roos |
| 4,181,131 A | 1/1980 | Ogiu |
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,532,924 A | 8/1985 | Auth et al. |
| 4,548,207 A | 10/1985 | Reimels |
| 4,567,890 A | 2/1986 | Ohta et al. |
| 4,582,056 A | 4/1986 | McCorkle, Jr. |
| 4,582,057 A | 4/1986 | Auth |
| 4,590,934 A | 5/1986 | Malis et al. |
| 4,593,691 A | 6/1986 | Lindstrom et al. |
| 4,641,649 A | 2/1987 | Walinsky |
| 4,643,186 A | 2/1987 | Rosen |
| 4,646,737 A | 3/1987 | Hussein |
| 4,654,024 A | 3/1987 | Crittendon |
| 4,658,817 A | 4/1987 | Hardy |
| 4,660,571 A | 4/1987 | Hess et al. |
| 4,672,962 A | 6/1987 | Hershenson |
| 4,674,499 A | 6/1987 | Pao |
| 4,682,596 A | 7/1987 | Bales et al. |
| 4,706,667 A | 11/1987 | Roos |
| 4,727,874 A | 3/1988 | Bowers et al. |
| 4,765,331 A | 8/1988 | Petruzzi et al. |
| 4,785,806 A | 11/1988 | Deckelbaum |
| 4,785,815 A | 11/1988 | Cohen |
| 4,785,823 A | 11/1988 | Eggers et al. |
| 4,799,479 A | 1/1989 | Spears |
| 4,805,616 A | 2/1989 | Pao |
| 4,823,791 A | 4/1989 | D'Amelio et al. |
| 4,832,048 A | 5/1989 | Cohen |
| 4,860,743 A | 8/1989 | Abela |
| 4,907,586 A | 3/1990 | Bille |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,966,597 A | 10/1990 | Cosman |
| 4,967,765 A | 11/1990 | Turner et al. |
| 4,968,314 A | 11/1990 | Michaels |
| 4,976,709 A | 12/1990 | Sand |
| 4,976,711 A | 12/1990 | Parins et al. |
| 4,979,948 A | 12/1990 | Geddes et al. |
| 4,998,933 A | 3/1991 | Eggers et al. |
| 5,007,908 A | 4/1991 | Rydell |
| 5,009,656 A | 4/1991 | Reimels |
| 5,035,696 A | 7/1991 | Rydell |
| 5,041,109 A | 8/1991 | Abela |
| 5,047,026 A | 9/1991 | Rydell |
| 5,047,027 A | 9/1991 | Rydell |
| 5,078,717 A | 1/1992 | Parins et al. |
| 5,078,736 A | 1/1992 | Behl |
| 5,080,660 A | 1/1992 | Buelna |
| 5,084,044 A | 1/1992 | Quint |
| 5,085,659 A | 2/1992 | Rydell |
| 5,088,997 A | 2/1992 | Delahuerga et al. |
| 5,093,877 A | 3/1992 | Aita |
| 5,098,431 A | 3/1992 | Rydell |
| 5,099,840 A | 3/1992 | Goble |
| 5,102,410 A | 4/1992 | Dressel |
| 5,108,391 A | 4/1992 | Flachenecker et al. |
| RE33,925 E | 5/1992 | Bales |
| 5,112,330 A | 5/1992 | Nishigaki et al. |
| 5,122,138 A | 6/1992 | Manwaring |
| 5,125,924 A | 6/1992 | Rudko |
| 5,125,926 A | 6/1992 | Rudko |
| 5,125,928 A | 6/1992 | Parins et al. |
| 5,137,530 A | 8/1992 | Sand |
| 5,140,987 A | 8/1992 | Schuger |
| 5,152,759 A | 10/1992 | Parel |
| 5,156,151 A | 10/1992 | Imran |
| 5,167,659 A | 12/1992 | Ohtomo et al. |
| 5,171,311 A | 12/1992 | Rydell et al. |
| 5,178,618 A | 1/1993 | Kandarpa |
| 5,178,620 A | 1/1993 | Eggers et al. |
| 5,188,635 A | 2/1993 | Radtke |
| 5,190,517 A | 3/1993 | Zieve et al. |
| 5,190,540 A | 3/1993 | Lee |
| 5,192,280 A | 3/1993 | Parins |
| 5,195,959 A | 3/1993 | Smith |
| 5,196,006 A | 3/1993 | Klopotek |
| 5,197,466 A | 3/1993 | Marchosky et al. |
| 5,197,963 A | 3/1993 | Parins |
| 5,200,604 A | 4/1993 | Rudko |
| 5,207,675 A | 5/1993 | Canady |
| 5,217,455 A | 6/1993 | Tan |
| 5,217,457 A | 6/1993 | Delahuerga et al. |
| 5,217,459 A | 6/1993 | Kamerling |
| 5,222,938 A | 6/1993 | Behl |
| 5,224,953 A | 7/1993 | Morgentaler |
| 5,230,334 A | 7/1993 | Klopotek |
| 5,242,386 A | 9/1993 | Holzer |
| 5,246,438 A | 9/1993 | Langberg |
| 5,250,045 A | 10/1993 | Bohley |
| 5,261,410 A | 11/1993 | Alfano |
| 5,263,951 A | 11/1993 | Spears |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,279,299 A | 1/1994 | Imran |
| 5,281,211 A | 1/1994 | Parel |
| 5,282,797 A | 2/1994 | Chess |
| 5,290,273 A | 3/1994 | Tan |
| 5,290,282 A | 3/1994 | Casscells |
| 5,292,321 A | 3/1994 | Lee |
| 5,293,868 A | 3/1994 | Nardella |
| 5,300,069 A | 4/1994 | Hunsberger et al. |
| 5,304,170 A | 4/1994 | Green |
| 5,306,238 A | 4/1994 | Fleenor |
| 5,312,395 A | 5/1994 | Tan |
| 5,312,400 A | 5/1994 | Bales et al. |
| 5,314,406 A | 5/1994 | Arias et al. |
| 5,318,525 A | 6/1994 | West |
| 5,324,254 A | 6/1994 | Phillips |
| 5,330,470 A | 7/1994 | Hagen |
| 5,330,496 A | 7/1994 | Alferness |
| 5,334,140 A | 8/1994 | Phillips |
| 5,334,190 A | 8/1994 | Seiler |
| 5,335,668 A | 8/1994 | Nardella |
| 5,336,217 A | 8/1994 | Buys et al. |
| 5,342,357 A | 8/1994 | Nardella |
| 5,348,554 A | 9/1994 | Imran |
| 5,366,443 A | 11/1994 | Eggers et al. |

| | | | | | | |
|---|---|---|---|---|---|---|
| 5,370,642 A | 12/1994 | Keller | | 5,681,282 A | 10/1997 | Eggers et al. |
| 5,370,644 A | 12/1994 | Langberg | | 5,681,308 A | 10/1997 | Edwards |
| 5,370,675 A | 12/1994 | Edwards et al. | | 5,683,366 A | 11/1997 | Eggers et al. |
| 5,374,265 A | 12/1994 | Sand | | 5,697,281 A | 12/1997 | Eggers et al. |
| 5,375,588 A | 12/1994 | Yoon | | 5,697,536 A | 12/1997 | Eggers et al. |
| 5,380,277 A | 1/1995 | Phillips | | 5,697,882 A | 12/1997 | Eggers et al. |
| 5,380,316 A | 1/1995 | Aita | | 5,697,909 A | 12/1997 | Eggers et al. |
| 5,383,876 A | 1/1995 | Nardella | | 5,700,262 A | 12/1997 | Acosta et al. |
| 5,383,917 A | 1/1995 | Desai et al. | | 5,725,524 A | 3/1998 | Mulier et al. |
| 5,389,096 A | 2/1995 | Aita | | 5,749,914 A | 5/1998 | Janssen |
| 5,395,312 A | 3/1995 | Desai | | 5,766,153 A | 6/1998 | Eggers et al. |
| 5,400,428 A | 3/1995 | Grace | | 5,766,192 A | 6/1998 | Zacca |
| 5,403,311 A | 4/1995 | Abele | | 5,769,843 A | 6/1998 | Abela |
| 5,417,687 A | 5/1995 | Nardella et al. | | 5,775,338 A | 7/1998 | Hastings |
| 5,419,767 A | 5/1995 | Eggers et al. | | 5,807,384 A | 9/1998 | Mueller |
| 5,423,803 A | 6/1995 | Tankovich | | 5,807,395 A | 9/1998 | Mulier et al. |
| 5,423,806 A | 6/1995 | Dale | | 5,810,764 A | 9/1998 | Eggers et al. |
| 5,423,810 A | 6/1995 | Goble et al. | | 5,810,809 A | 9/1998 | Rydell |
| 5,423,882 A | 6/1995 | Jackman et al. | | 5,817,013 A | 10/1998 | Ginn |
| 5,425,355 A | 6/1995 | Kulick | | 5,823,955 A | 10/1998 | Kuck |
| 5,429,144 A | 7/1995 | Wilk | | 5,836,868 A | 11/1998 | Ressemann |
| 5,429,604 A | 7/1995 | Hammersmark | | 5,840,059 A | 11/1998 | March |
| 5,433,708 A | 7/1995 | Nichols | | 5,843,019 A | 12/1998 | Eggers et al. |
| 5,436,566 A | 7/1995 | Thompson et al. | | 5,860,951 A | 1/1999 | Eggers |
| 5,437,658 A | 8/1995 | Muller | | 5,860,974 A | 1/1999 | Abele |
| 5,437,662 A | 8/1995 | Nardella | | 5,860,975 A | 1/1999 | Goble et al. |
| 5,438,302 A | 8/1995 | Goble | | 5,871,469 A | 2/1999 | Eggers et al. |
| 5,441,499 A | 8/1995 | Fritzsch | | 5,873,855 A | 2/1999 | Eggers et al. |
| 5,445,634 A | 8/1995 | Keller | | 5,885,277 A | 3/1999 | Korth |
| 5,451,224 A | 9/1995 | Goble et al. | | 5,888,198 A | 3/1999 | Eggers et al. |
| 5,454,809 A | 10/1995 | Janssen | | 5,891,095 A | 4/1999 | Eggers et al. |
| 5,456,680 A | 10/1995 | Taylor | | 5,891,140 A * | 4/1999 | Ginn et al. .................. 606/48 |
| 5,462,544 A | 10/1995 | Sakesena | | 5,893,885 A | 4/1999 | Webster, Jr. |
| 5,464,404 A | 11/1995 | Abela | | 5,897,553 A | 4/1999 | Mulier |
| 5,484,433 A | 1/1996 | Taylor | | 5,902,272 A | 5/1999 | Eggers et al. |
| 5,487,385 A | 1/1996 | Avitall | | 5,944,715 A | 8/1999 | Goble et al. |
| 5,496,312 A | 3/1996 | Klicek | | 6,004,319 A | 12/1999 | Goble et al. |
| 5,496,314 A | 3/1996 | Eggers | | 6,013,076 A | 1/2000 | Goble et al. |
| 5,496,317 A | 3/1996 | Goble et al. | | 6,015,406 A | 1/2000 | Goble et al. |
| 5,500,012 A | 3/1996 | Brucker | | 6,024,733 A | 2/2000 | Eggers et al. |
| 5,505,725 A | 4/1996 | Samson | | 6,027,501 A | 2/2000 | Goble et al. |
| 5,507,771 A | 4/1996 | Gianturco | | 6,039,734 A | 3/2000 | Goble et al. |
| 5,514,128 A | 5/1996 | Hillsman | | 6,056,746 A | 5/2000 | Goble et al. |
| 5,514,130 A | 5/1996 | Baker | | 6,063,079 A | 5/2000 | Hovda et al. |
| 5,540,712 A | 7/1996 | Kleshinski | | 6,066,134 A | 5/2000 | Eggers et al. |
| 5,542,928 A | 8/1996 | Evans | | 6,068,628 A | 5/2000 | Fanton et al. |
| 5,545,161 A | 8/1996 | Imran | | 6,074,386 A | 6/2000 | Goble et al. |
| 5,545,211 A | 8/1996 | An | | 6,090,106 A | 7/2000 | Goble et al. |
| 5,554,152 A | 9/1996 | Aita | | 6,093,186 A | 7/2000 | Goble et al. |
| 5,556,397 A | 9/1996 | Long et al. | | 6,102,046 A | 8/2000 | Weinstein et al. |
| 5,567,890 A | 10/1996 | Lindberg | | 6,109,268 A | 8/2000 | Thapliyal et al. |
| 5,569,242 A | 10/1996 | Lax et al. | | 6,117,109 A | 9/2000 | Eggers et al. |
| 5,571,100 A | 11/1996 | Goble et al. | | 6,126,682 A | 10/2000 | Sharkey et al. |
| 5,571,169 A | 11/1996 | Plaia | | 6,142,992 A | 11/2000 | Cheng et al. |
| 5,579,764 A | 12/1996 | Goldreyer | | 6,149,620 A | 11/2000 | Baker et al. |
| 5,584,872 A | 12/1996 | LaFontaine et al. | | 6,159,194 A | 12/2000 | Eggers et al. |
| 5,591,159 A | 1/1997 | Taheri | | 6,159,208 A | 12/2000 | Hovda et al. |
| 5,603,731 A | 2/1997 | Whitney | | 6,161,543 A | 12/2000 | Cox |
| 5,607,421 A | 3/1997 | Jeevanandam | | 6,168,593 B1 | 1/2001 | Sharkey et al. |
| 5,609,151 A | 3/1997 | Mulier et al. | | 6,174,308 B1 | 1/2001 | Goble |
| 5,620,438 A | 4/1997 | Amplatz | | 6,179,824 B1 | 1/2001 | Eggers et al. |
| 5,626,576 A | 5/1997 | Janssen | | 6,179,836 B1 | 1/2001 | Eggers et al. |
| 5,633,578 A | 5/1997 | Eggers et al. | | 6,183,469 B1 | 2/2001 | Thapliyal et al. |
| 5,643,251 A | 7/1997 | Hillsman | | 6,190,381 B1 | 2/2001 | Olsen et al. |
| 5,643,255 A | 7/1997 | Organ | | 6,203,542 B1 | 3/2001 | Ellsberry et al. |
| 5,647,869 A | 7/1997 | Goble et al. | | 6,210,402 B1 | 4/2001 | Olsen et al. |
| 5,662,680 A | 9/1997 | Desai | | 6,224,592 B1 | 5/2001 | Eggers et al. |
| 5,669,907 A | 9/1997 | Platt | | 6,228,081 B1 | 5/2001 | Goble |
| 5,672,170 A | 9/1997 | Cho | | 6,235,020 B1 | 5/2001 | Cheng et al. |
| 5,673,695 A | 10/1997 | McGee | | 6,238,391 B1 | 5/2001 | Olsen et al. |
| 5,676,693 A | 10/1997 | LaFontaine | | 6,254,600 B1 | 7/2001 | Willink et al. |

| | | | |
|---|---|---|---|
| 6,261,286 B1 | 7/2001 | Goble et al. | |
| 6,264,652 B1 | 7/2001 | Eggers et al. | |
| 6,277,112 B1 | 8/2001 | Underwood et al. | |
| 6,293,942 B1 | 9/2001 | Goble et al. | |
| 6,296,636 B1 | 10/2001 | Cheng et al. | |
| 6,296,638 B1 | 10/2001 | Davison et al. | |
| 6,306,134 B1 | 10/2001 | Goble et al. | |
| 6,312,408 B1 | 11/2001 | Eggers et al. | |
| 6,322,549 B1 | 11/2001 | Eggers et al. | |
| 6,355,032 B1 | 3/2002 | Hovda et al. | |
| 6,363,937 B1 | 4/2002 | Hovda et al. | |
| 6,379,351 B1 | 4/2002 | Thapliyal et al. | |
| 6,391,025 B1 | 5/2002 | Weinstein et al. | |
| 6,416,507 B1 | 7/2002 | Eggers et al. | |
| 6,416,508 B1 | 7/2002 | Eggers et al. | |
| 6,432,103 B1 | 8/2002 | Ellsberry et al. | |
| 6,530,922 B2 | 3/2003 | Cosman | |
| 6,602,248 B1 | 8/2003 | Sharps et al. | |
| 2002/0029036 A1 | 3/2002 | Goble et al. | |

FOREIGN PATENT DOCUMENTS

| | | | |
|---|---|---|---|
| DE | 29619029 | 4/1997 | |
| EP | 0 703 461 | 3/1996 | ........... G01R/27/02 |
| EP | 0553576 | 4/1996 | |
| EP | 0 740 926 A2 | 11/1996 | ........... A61B/17/39 |
| EP | 0 754 437 | 1/1997 | ........... A61B/17/39 |
| EP | 0515867 | 7/1999 | |
| EP | 0 694 290 | 11/2000 | ........... A61B/18/04 |
| FR | 2313949 | 1/1977 | ............ A61N/3/02 |
| GB | 2 308 979 | 7/1997 | ........... A61B/17/36 |
| GB | 2 308 980 | 7/1997 | ........... A61B/17/36 |
| GB | 2 308 981 | 7/1997 | ........... A61B/17/36 |
| GB | 2 327 350 | 1/1999 | ........... A61B/17/39 |
| GB | 2 327 351 | 1/1999 | ........... A61B/17/39 |
| GB | 2 327 352 | 1/1999 | ........... A61B/17/39 |
| JP | 57-57802 | 4/1982 | ............ A61B/1/00 |
| JP | 57-117843 | 7/1982 | ........... A61B/17/39 |
| WO | 90/03152 | 4/1990 | ........... A61B/17/39 |
| WO | 90/07303 | 7/1990 | ........... A61B/17/39 |
| WO | 92/21278 | 12/1992 | ............ A61B/5/04 |
| WO | 93/13816 | 7/1993 | ........... A61B/17/36 |
| WO | 93/20747 | 10/1993 | ............ A61B/5/00 |
| WO | 94/04220 | 3/1994 | |
| WO | 94/08654 | 4/1994 | .......... A61M/37/00 |
| WO | 94/14383 | 7/1994 | |
| WO | 95/34259 | 12/1995 | ............. A61F/5/48 |
| WO | 96/00042 | 1/1996 | ........... A61B/17/39 |
| WO | 96/35469 | 11/1996 | |
| WO | 96/39962 | 12/1996 | |
| WO | 96/39963 | 12/1996 | |
| WO | 96/39965 | 12/1996 | |
| WO | 97/00646 | 1/1997 | ........... A61B/17/39 |
| WO | 97/00647 | 1/1997 | ........... A61B/17/39 |
| WO | 97/24073 | 7/1997 | ........... A61B/17/39 |
| WO | 97/24074 | 7/1997 | ........... A61B/17/39 |
| WO | 97/24993 | 7/1997 | ........... A61B/17/39 |
| WO | 97/24994 | 7/1997 | ........... A61B/17/39 |
| WO | 97/25101 | 7/1997 | |
| WO | 97/34540 | 9/1997 | |
| WO | 97/44071 | 11/1997 | |
| WO | 97/48345 | 12/1997 | ........... A61B/17/39 |
| WO | 97/48346 | 12/1997 | ........... A61B/17/39 |
| WO | 98/07468 | 2/1998 | ............ A61N/1/40 |
| WO | 98/17185 | 4/1998 | |
| WO | 98/17186 | 4/1998 | |
| WO | 98/19614 | 5/1998 | |
| WO | 98/23324 | 6/1998 | |
| WO | 98/27877 | 7/1998 | |
| WO | 98/27879 | 7/1998 | ........... A61B/17/36 |
| WO | 98/27880 | 7/1998 | ........... A61B/17/39 |
| WO | 98/30144 | 7/1998 | |
| WO | 98/38925 | 9/1998 | |
| WO | 98/39038 | 9/1998 | |
| WO | 99/51155 | 10/1999 | ........... A61B/17/36 |
| WO | 99/51158 | 10/1999 | ........... A61B/17/39 |

OTHER PUBLICATIONS

J.W. Ramsey et al. *Urological Research* vol. 13, pp. 99–102 (1985).

V.E. Elsasser et al. *Acta Medicotechnica* vol. 24, No. 4, pp. 129–134 (1976).

P.C. Nardella (1989) *SPIE* 1068: 42–49 Radio Frequency Energy and Impedance Feedback.

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

Kramolowsky et al. *J. of Urology* vol. 143, pp. 275–277 (1990).

Kramolowsky et al. *J. of Urology* vol. 146, pp. 669–674 (1991).

Slager et al. *Z. Kardiol.* 76:Suppl. 6, 67–71 (1987).

Slager et al. *JACC* 5 (6) :1382–6 (1985).

Olsen MD, Bipolar Laparoscopic Cholecstectomy Lecture (marked confidential), Oct. 7, 1991.

Codman & Shurtleff, Inc. "The Malis Bipolar Electrosurgical System CMC–III Instruction Manual" Jul. 1991.

Valley Forge's New Products, CLINICA, 475, 5, Nov. 6, 1991.

Valley Forge Scientific Corp., "Summary of Safety and Effective Information from 510K," 1991.

Codman & Shurtleff, Inc. "The Malis Bipolar Coagulating and Bipolar Cutting System CMC–II" brochure, early 1991.

L. Malis, "The Value of Irrigation During Bipolar Coagulation" See ARTC 21602, early Apr. 9, 1993.

L. Malis, "Excerpeted from a seminar by Leonard I. Malis, M.D. at the 1995 American Association of Neurological Surgeons Meeting," 1995.

L. Malis, "Electrosurgery, Technical Note," *J. Neursurg.*, vol. 85, 970–975, Nov. 1996.

Ian E. Shuman, "Bipolar Versus Monopolar Electrosurgery: Clinical Applications," *Dentistry Today*, vol. 20, No. 12, Dec. 2001.

Protell et al., "Computer–Assisted Electrocoagulation: Bipolar v. Monopolar in the Treatment of Experimental Canine Gastric Ulcer Bleeding," *Gastroenterology* vol. 80, No. 3, pp. 451–455.

Cook and Webster, "Therapeutic Medical Devices: Application and Design," 1982.

Valleylab SSE2L Instruction Manual, Jan. 6, 1983.

Robert D. Tucker et al., "Demodulated Low Frequency Currents from Electrosurgical Procedures," *Surgery, Gynecology and Obstetrics*, 159: 39–43, 1984.

Lu, et al., "Electrical Thermal Angioplasty: Catheter Design Features, In Vitro Tissue Ablation Studies and In Vitro Experimental Findings," *Am J. Cardiol* vol. 60, pp. 1117–1122.

Selikowitz & LaCourse, "Electric Current and Voltage Recordings on the Myocardium During Electrosurgical Procedures in Canines," *Surgery, Gynecology & Obstetrics*, vol. 164, 219–224, Mar. 1987.

J. O'Malley, Schaum's Outline of Theory and Problems of Basic Circuit Analysis, McGraw–Hill, $2^{nd}$ Ed., 1992, pp. 3–5.

Arnaud Wattiez et al., "Electrosurgery in Operative Endoscopy," Electrosurgical Effects, Blackwell Science, pp. 85–93, 1995.

Leslie A. Geddes, "Medical Device Accidents: With Illustrative Cases" CRC Press, 1998.

Wyeth, "Electrosurgical Unit" pp. 1181–1202.

C.P. Swain, et al., *Gut* vol. 25, pp. 1424–1431 (1984).

Piercey et al., *Gastroenterology* vol. 74(3), pp. 527–534 (1978).

A.K. Dobbie *Bio–Medical Engineering* vol. 4, pp. 206–216 (1969).

B. Lee et al. JACC vol. 13(5), pp. 1167–1175 (1989).

K. Barry et al. *American Heart Journal* vol. 117, pp. 332–341 (1982).

W. Honig *IEEE* pp. 58–65 (1975).

Jacob Kline, *Handbood of Biomedical Engineering*, Academic Press Inc., N.Y., pp. 98–113, 1988.

M.B. Dennis et al. "Evolution of Electrofulguration in Control of Bleeding of Experimental Gastric Ulcers," Digestive Diseases and Sciences, vol. 24, No. 11, 845–848.

Letter from Department of Health to Jerry Malis dated Apr. 15, 1985.

Letter from Jerry Malis to FDA dated Jul. 25, 1985.

Letter from Department of Health to Jerry Malis dated Apr. 22, 1991.

Leonard Malis, "Instrumentation for Microvascular Neurosurgery" *Cerebrovascular Surgery*, vol. 1, 245–260, 1985.

Valleylab, Inc. "Valleylab Part No. 945 100 102 A" Surgistat Service Manual, Jul. 1988

Leonard I. Malis, "New Trends in Microsurgery and Applied Technology," *Advanced Technology in Neurosurgery*, Jan. 16, 1988.

Regional myocardial blood flow and cardiac mechanics in dog hearts with $CO_2$ laser–induced intramyocardial revascularization, Basic Research in Cardiology 85:179–197 (1990) R. Hardy, F. James, R Millard and S. Kaplan.

Transventricular Revascularization by Laser, Lasers in Surgery and Medicine 2:187–198 (1982) M. Mirhoseini MD, Muckerheide, and Cayton RN.

Transmyocardial Laser Revascularization: A Review; J. Of Clinical Laser Medicine & Surgery V. 11, No. 1 1993 pp 15–19; M. Mirhoseini, MD, S. Shelgikar MD, M Cayton RN.

Transmural Channels Can Protect Ischemic Tissue; Circulation vol. 93 No. 1, Jan. 1, 1996; P. Whittaker, PhD; Karel Rakusan, MD, Ph.D; Robert Kloner, MD, PhD.

Treatment of Acute Myocardial Infarction by Transmural Blood Supply from the Ventricular Cavity; Europ. Surg. Res. 3; 130–138 (1971) P. Walter, H. Hundeshagen and H.G. Borst.

* cited by examiner

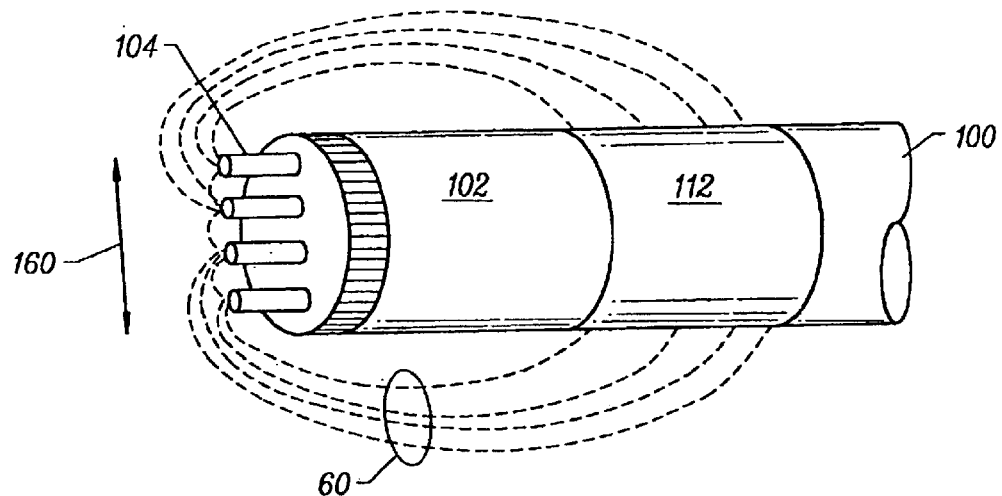
FIG. 21
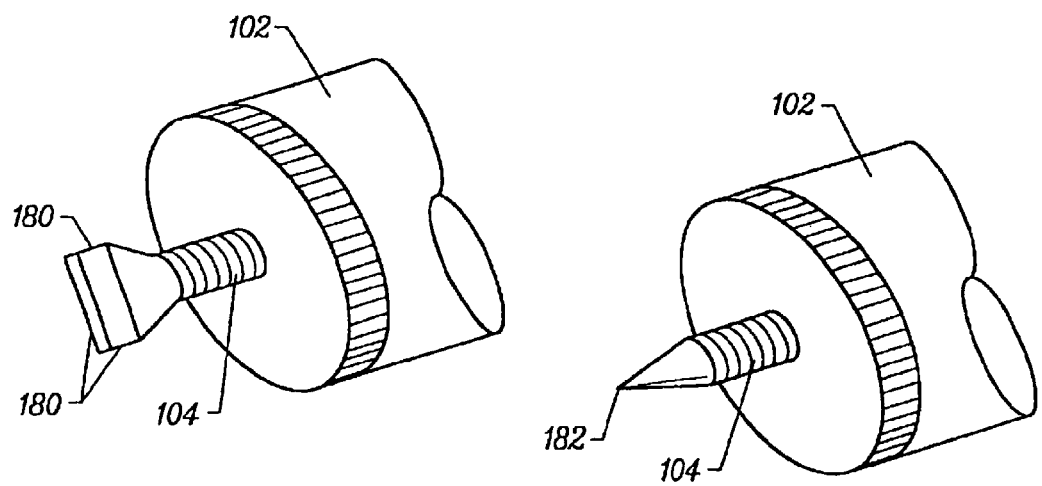
FIG. 22
FIG. 23

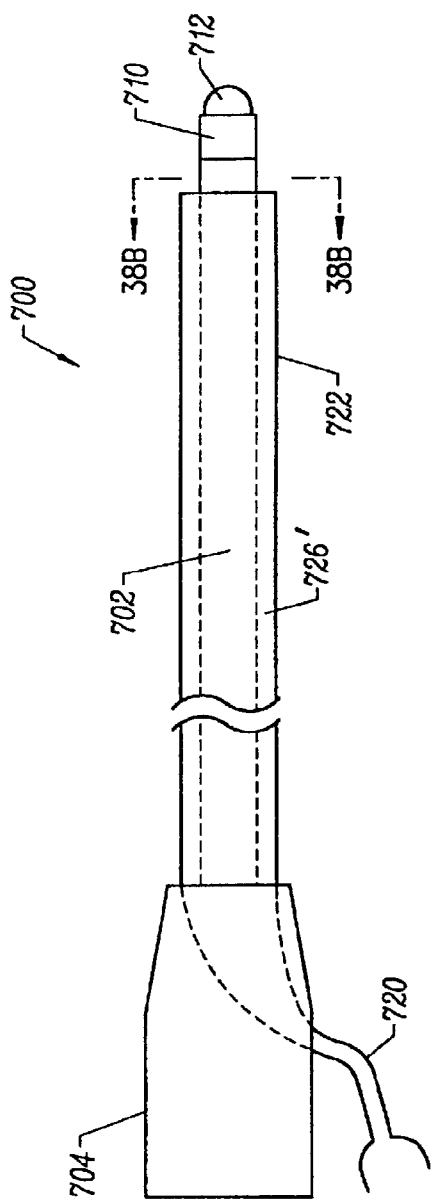
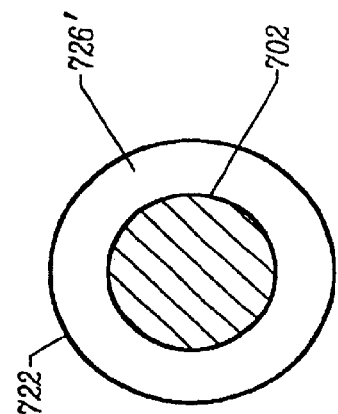
FIG. 38A
FIG. 38B

METHOD FOR HARVESTING GRAFT VESSEL

CROSS-REFERENCES TO RELATED APPLICATIONS

The present invention claims priority from U.S. Provisional Patent Application No. 60/182,751 filed Feb. 16, 2000, and is a continuation-in-part of U.S. patent application Ser. No. 09/162,117, filed Sep. 28, 1998 now U.S. Pat. No. 6,117,109, which is a continuation in part of U.S. patent application Ser. No. 08/977,845, filed Nov. 25, 1997 now U.S. Pat. No. 6,210,402, which is a continuation-in-part of application Ser. No. 08/562,332, filed Nov. 22, 1995 now U.S. Pat. No. 6,024,773, and U.S. patent application Ser. No. 09/041,934, filed Mar. 13, 1998 now U.S. Pat. No. 6,391,025, which is a continuation in part of U.S. patent application Ser. No. 08/990,374, filed Dec. 15, 1997 now U.S. Pat. No. 6,109,268, which is a continuation-in-part of U.S. patent application Ser. No. 08/485,219 (now U.S. Pat. No. 5,697,281), filed on Jun. 7, 1995, which was a continuation-in-part of PCT International Application, U.S. National Phase Serial No. PCT/US94/05168 (now U.S. Pat. No. 5,697,909), filed on May 10, 1994, which was a continuation-in-part of application Ser. No. 08/059,681, filed on May 10, 1993, now abandoned, the complete disclosures of which are incorporated herein by reference for all purposes.

The present invention is also related to commonly assigned copending U.S. Provisional Patent Application No. 60/062,996, filed Oct. 23, 1997, U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, patent application Ser. Nos. 09/109,219, 09/058,571, 08/874,173 and 09/002,315, filed on Jun. 30, 1998, Apr. 10, 1998, Jun. 13, 1997, and Jan. 2, 1998, respectively and U.S. patent application Ser. No. 09/054,323, filed on Apr. 2, 1998, U.S. patent application Ser. No. 09/010,382, filed Jan. 21, 1998, and U.S. patent application Ser. No. 09/032,375, filed Feb. 27, 1998, U.S. patent application Ser. No. 08/977,845, filed on Nov. 25, 1997, Ser. No. 08/942,580, filed on Oct. 2, 1997, U.S. application Ser. No. 08/753,227, filed on Nov. 22, 1996, U.S. application Ser. No. 08/687,792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992, which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention generally relates to electrosurgical systems and methods for severing or dissecting target tissues or organs (e.g., blood vessels). The invention relates more particularly to electrosurgical apparatus and methods for dissecting a tissue or organ via molecular dissociation of tissue components. The present invention further relates to electrosurgical instruments and methods for harvesting blood vessels such as the internal thoracic, radial, epigastric or other free human arteries, and/or the saphenous vein, or the like, for use in coronary artery bypass graft procedures.

A prevalent form of cardiovascular disease is atherosclerosis in which the cardiovascular system leading to the heart is damaged or obstructed as a result of occluding material in the blood stream. Vascular complications produced by atherosclerosis, such as stenosis, aneurysm, rupture or occlusion increase the likelihood of angina, stroke, and heart attacks. In many cases, the obstruction of the blood stream leading to the heart can be treated by a coronary artery bypass graft (CABG) procedure.

In a conventional CABG procedure, the obstruction is bypassed by a vascular conduit established between an arterial blood source and the coronary artery to a location beyond the obstruction. The vascular conduit is typically a non-critical artery or vein harvested from elsewhere in the body. In a procedure known as "free bypass graft", the saphenous vein is harvested from the patient's leg and is used as the vascular conduit. One end of the saphenous vein is anastomosed to the aorta and the other end is anastomosed to the diseased coronary artery at a location past the obstruction. In a procedure known as "in situ bypass graft", an internal mammary artery (IMA) is used as the bypass conduit. In an in situ bypass graft procedure, the surgeon dissects a sufficient length of the artery from its connective tissue, then transects the artery and connects the transected end to the diseased coronary past the obstruction, and leaves the other end of the IMA attached to the arterial supply.

The internal mammary arteries are particularly desirable for use as in situ bypass grafts, as they are conveniently located, have diameters and blood flow volumes that are comparable to those of coronary arteries, and have superior patency rates. Use of the left or right IMA as a bypass graft first involves harvesting the IMA from the inside chest wall.

In conventional CABG procedures, access to the IMA is typically obtained either through a sternotomy or a gross thoracotomy. In the sternotomy or gross thoracotomy, the surgeon typically uses a saw or other cutting instrument to cut the sternum longitudinally to allow two opposing halves of the anterior portion of the rib cage to be spread apart. The opening into the thoracic cavity is created so that the surgeon may directly visualize the heart and thoracic cavity. However, such methods suffer from numerous drawbacks. For example, the longitudinal incision in the sternum often results in bone bleeding, which is difficult to stop. The bone bleeding can produce a high degree of trauma, a larger risk of complications, an extended hospital stay, and a painful recovery period for the patient. Once the surgeon has accessed the thoracic cavity, the conventional method of harvesting the IMA involves the use of scalpels or conventional electrosurgical devices. Conventional electrosurgical instruments and techniques are widely used in surgical procedures because they generally reduce patient bleeding and trauma associated with cutting operations, as compared with mechanical cutting and the like. Conventional electrosurgical procedures may be classified as operating in monopolar or bipolar mode. Monopolar techniques rely on external grounding of the patient, where the surgical device defines only a single electrode pole. Bipolar devices have two electrodes for the application of current between their surfaces. Conventional electrosurgical devices and procedures, however, suffer from a number of disadvantages. For example, conventional electrosurgical cutting devices typically operate by creating a voltage difference between the active electrode and the target tissue, causing an electrical arc to form across the physical gap between the electrode and the tissue. At the point of contact of the electric arcs with the tissue, rapid tissue heating occurs due to high current density between the electrode and the tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue.

Further, monopolar electrosurgical devices generally direct electric current along a defined path from the exposed or active electrode through the patient's body to the return electrode, the latter externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high electrical impedance, large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue.

Bipolar electrosurgical devices have an inherent advantage over monopolar devices because the return current path does not flow through the patient. In bipolar electrosurgical devices, both the active and return electrode are typically exposed so that both electrodes may contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

Thus, there is a need for an electrosurgical apparatus which can be used for the precise removal or modification of tissue at a specific location, wherein a target tissue or organ can be dissected or transected with minimal, or no, collateral tissue damage. The instant invention provides such an apparatus and related methods suitable for dissection, transection, or harvesting of a tissue or organ, such as the IMA, in a minimally invasive procedure.

SUMMARY OF THE INVENTION

The present invention generally provides systems, apparatus, and methods for selectively applying electrical energy to cut, dissect, or transect a tissue or organ of a patient. More specifically, the electrosurgical systems and methods are useful for harvesting and dissecting veins and arteries from the patient's body. Even more particularly, the present invention is useful for the harvesting and dissecting of the IMA or the saphenous vein for a CABG procedure.

In one aspect, the present invention provides a method of creating an incision in a body structure. An electrosurgical probe is positioned adjacent the target tissue so that one or more active electrode(s) are brought into at least partial contact or close proximity with the target tissue. High frequency voltage is then applied between the active electrode(s) and one or more return electrode(s) and the active electrode(s) are moved, translated, reciprocated, or otherwise manipulated to cut through a portion of the tissue. In some embodiments, an electrically conductive fluid, e.g., isotonic saline or conductive gel, is delivered or applied to the target site to substantially surround the active electrode(s) with the fluid. In other embodiments, the active electrode(s) are immersed within the electrically conductive fluid. In both embodiments, the high frequency voltage may be selected to effect a controlled depth of hemostasis of severed blood vessels within the tissue, which greatly improves the surgeon's view of the surgical site.

In one aspect, tissue is cut, dissected, and/or transected by molecular dissociation or disintegration processes. (In contrast, in conventional electrosurgery tissue is cut by rapidly heating the tissue until cellular fluids explode, producing a cutting effect along the pathway of localized heating.) The present invention volumetrically removes the tissue along the cutting pathway in a cool ablation process that minimizes thermal damage to surrounding tissue. In these embodiments, the high frequency voltage applied to the active electrode(s) is sufficient to vaporize the electrically conductive fluid (e.g., gel or saline) between the active electrode(s) and the tissue. Within the vaporized fluid, a plasma is formed and charged particles (e.g., electrons) cause the molecular breakdown or disintegration of the tissue, perhaps to a depth of several cell layers. This molecular dissociation is accompanied by the volumetric removal of the tissue, e.g., along the incision of the tissue. This process can be precisely controlled to effect the volumetric removal of tissue as thin as 10 microns to 150 microns with minimal heating of, or damage to, surrounding or underlying tissue structures. A more complete description of this phenomenon is described in commonly assigned U.S. Pat. No. 5,683,366, the complete disclosure of which is incorporated herein by reference.

In a specific embodiment, the present invention provides a method of accessing a patient's thoracic cavity. The active electrode(s) are positioned in contact or in close proximity to a surface of the sternum. A high frequency voltage is applied between the active electrode(s) and a return electrode. The active electrodes are moved across the sternum to create an incision. In a specific configuration, the sides of the active electrode are slidingly engaged with the sternum as the incision is being made, so as to cause coagulation and hemostasis within the sternum.

In another exemplary embodiment, the present invention provides a method for harvesting the IMA from a patient. The electrosurgical probe is positioned either by direct visualization and access of a sternotomy or indirectly via endoscopic access adjacent the IMA and high frequency electrical energy is applied between one or more active electrode(s) and one or more return electrode(s). The probe is then moved so that the active electrode(s) volumetrically removes connective tissue adjacent to the IMA so that the IMA is free from connective tissue along a portion of its length. In an exemplary embodiment, the probe is positioned adjacent to the IMA, and advanced along the length of the IMA while high frequency electrical energy is applied between the active electrode(s) and a return electrode to remove or cut the connective tissue or other structures surrounding the IMA. The residual heat from the electrical energy may also provides simultaneous hemostasis of severed blood vessels, which increases visualization and improves recovery time for the patient. In addition, the ability to simultaneously cut through tissue on either side of the IMA decreases the length of the procedure, which further improves patient recovery time. After a suitable length of the IMA has been dissected, it may be transected, and anastomosed to a diseased coronary artery using known methods. In some embodiments, an electrically conductive fluid (liquid, gas, or gel) is placed at the target site adjacent to the IMA so as to provide a current flow path between the return electrode and the active electrode.

Apparatus according to the present invention generally include an electrosurgical instrument, such as a probe or catheter, having a shaft of multiple lengths with proximal and distal ends, one or more active electrode(s) at the distal end and one or more connectors coupling the active electrode(s) to a source of high frequency electrical energy. The active electrode(s) are preferably designed for cutting tissue; i.e., they may comprise a variety of configurations including a distal edge, blade, hook, bi-polar grasping and desiccating "scissors or a point. In one embodiment, a plurality of active electrodes are aligned with each other to form a linear electrode array for cutting a path through the tissue. In another exemplary embodiment, the active electrode(s) include a sharp distal point to facilitate the cutting of the target tissue. In one specific configuration, the active electrode is a blade having a sharp distal point and sides. As the sharp distal point incises the tissue, the sides of the blade slidingly contact the incised tissue. The electrical current flows through that portion of the tissue in the vicinity of the active electrode and/or the conductive fluid to the return electrode, such that the target tissue is first severed, and then the severed tissue may be coagulated.

The apparatus can further include a fluid delivery element for delivering electrically conductive fluid to the active electrode(s) and the target site. The fluid delivery element may be located on the probe, e.g., a fluid lumen or tube, or it may be part of a separate instrument. Alternatively, an electrically conductive gel or spray, such as a saline electrolyte or other conductive gel, may be applied the target site. In this embodiment, the apparatus may not have a fluid delivery element. In both embodiments, the electrically conductive fluid preferably provides a current flow path between the active electrode(s) and one or more return electrode(s). In an exemplary embodiment, the return electrode is located on the probe and spaced a sufficient distance from the active electrode(s) to substantially avoid or minimize current shorting therebetween and to shield the return electrode from tissue at the target site.

In a specific configuration, the electrosurgical probe includes an electrically insulating electrode support member having a tissue treatment surface at the distal end of the probe. One or more active electrode(s) are coupled to, or integral with, the electrode support member such that the active electrode(s) are spaced from the return electrode. In one embodiment, the probe includes a plurality of active electrode(s) having distal edges linearly aligned with each other to form a sharp cutting path for cutting tissue. The active electrodes are preferably electrically isolated from each other, and they extend about 0.2 mm to about 10 mm distally from the tissue treatment surface of the electrode support member. In this embodiment, the probe may further include one or more lumens for delivering electrically conductive fluid to one or more openings around the tissue treatment surface of the electrode support member. In an exemplary embodiment, the lumen extends through a fluid tube exterior to the probe shaft that ends proximal to the return electrode.

In another aspect of the invention, the electrode support member comprises a plurality of wafer layers bonded together, e.g., by a glass adhesive or the like. The wafer layers each have conductive strips plated or printed thereon to form the active electrode(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, tungsten, palladium, silver or the like.

In another aspect of the invention, there is provided an electrosurgical probe having a blade-like active electrode affixed to an electrically insulating electrode support on the distal end of a shaft. In a specific configuration, the active electrode is in the form of a substantially flat metal blade having an active edge and first and second blade sides. The return electrode is typically located on the shaft distal end proximal to the electrode support. In use, the active electrode and the return electrode are coupled to opposite poles of a high frequency power supply. The active edge may have a variety of shapes, and is adapted for generating high current densities thereon, and for precisely severing or ablating tissue or an organ in a highly controlled manner via molecular dissociation of tissue components. The first and second blade sides are adapted for engaging with tissue, such as tissue severed by the active edge, and for coagulating tissue engaged therewith.

The probe may be provided in various configurations, for example, according to a particular procedure to be performed. Thus, the electrode support may be arranged terminally or laterally on the probe, and the blade active electrode may be arranged terminally or laterally on the electrode support. The shaft distal end may have a beveled end, a distal curve, and/or a laterally compressed region. Each of these features or elements of the probe may facilitate accessing a tissue or organ targeted for treatment or modification by the probe. In addition, the laterally compressed region may be adapted for accommodating the electrode support.

In another aspect of the invention, there is provided a method of harvesting a tissue or organ using an electrosurgical probe having at least one active electrode disposed on the distal end of the probe. In one embodiment, the active electrode is in the form of a single blade including an active edge and first and second blade sides. In situations where the tissue to be harvested is concealed by an overlying tissue, the tissue to be harvested must first be accessed by incising or removing the overlying tissue. Removal of the overlying tissue may be performed in various ways, including: 1) mechanically, e.g. using a scalpel, rongeur, surgical saw or drill, etc. or a combination thereof; 2) via conventional electrosurgery, e.g., a Bovie; or 3) using an electrosurgical probe of the instant invention adapted for severing tissue in a cool ablation process involving molecular dissociation of tissue components. Once the tissue or organ to be harvested is accessible, the tissue or organ to be harvested may be dissected by juxtaposing the active edge of the blade electrode against the surrounding connective tissue, and applying a high frequency voltage difference between the active and return electrodes sufficient to cause molecular dissociation of connective tissue components. In this way, the connective tissue adjacent to the active electrode is ablated at a temperature in the range of 40° C. to 70° C., with no, or minimal, thermal damage to the tissue to be harvested.

In another aspect, the invention provides a method of harvesting or otherwise providing a graft blood vessel, e.g., for a patient undergoing a CABG procedure. Such a method may involve dissecting a graft vessel, such as the IMA, from connective tissue adjacent to the graft vessel to provide a free portion of the graft vessel. Thereafter, the graft vessel may be severed or transected at one or more selected positions along the length of the free portion of the graft vessel by positioning the active electrode in contact with or close proximity to the selected position of the graft vessel, and applying a high frequency voltage to the active electrode, wherein the graft vessel is transected via localized molecular dissociation of graft vessel components in the vicinity of the active electrode. The transected graft vessel may then be anastomosed to a recipient blood vessel, such as a coronary artery. An incision may be made in the recipient vessel via electrosurgical molecular dissociation of tissue components of the recipient vessel, to provide an opening suitable for accommodating the transected vessel in an end-to-side anastomosis.

For a further understanding of the nature and advantages of the invention, reference should be made to the following description taken in conjunction with the accompanying drawings.

BRIEF DESCRIPTION OF THE DRAWINGS

FIGS. 9A–12A are side views of the Individual wafer layers of the electrode support;

FIGS. 9B–12B axe cross-sectional views of the individual wafer layers;

FIG. 21 is a detailed end view of an electrosurgical probe having an elongate, linear array of active electrodes suitable for use in surgical cutting;

FIG. 22 is a detailed view of a single active electrode having a flattened end at its distal tip;

FIG. 23 is a detailed view of a single active electrode having a pointed end at its distal tip;

FIGS. 38A, and 38B are a side view and an end view, respectively, of an electrosurgical probe having an outer sheath surrounding the probe shaft, according to another embodiment of the invention;

DESCRIPTION OF THE SPECIFIC EMBODIMENTS

Figure 1:
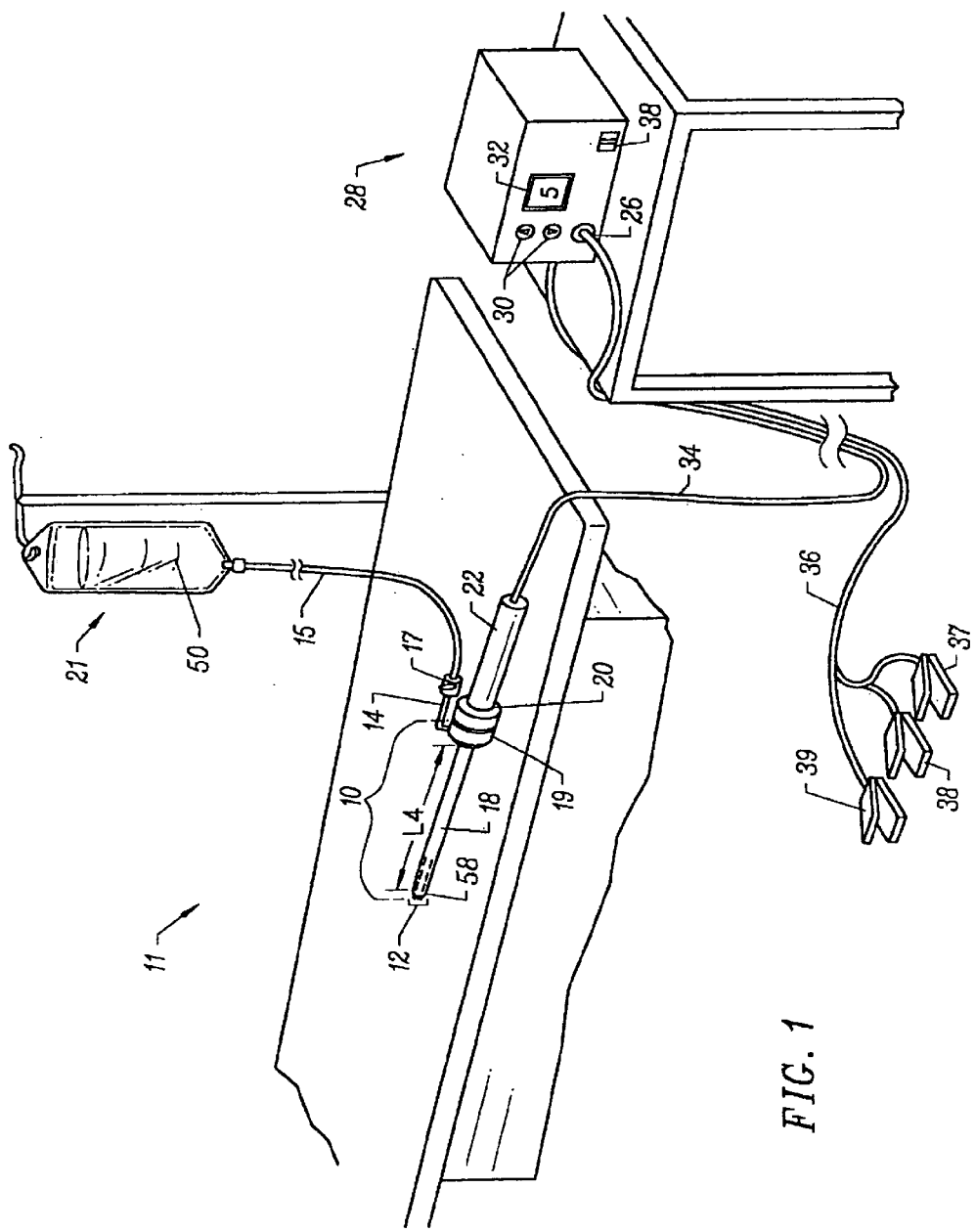
FIG. 1 is a perspective view of an electrosurgical system incorporating a power supply and an electrosurgical probe for tissue ablation, resection, incision, contraction, vessel harvesting, and hemostasis, according to the present invention.

The present invention provides systems and methods for selectively applying electrical energy to a target location within or on a patient's body, particularly for making incisions to access a tissue or organ within a patient's body, to dissect or harvest the tissue or organ from the patient, and to transect or otherwise modify the tissue or organ. In one aspect, the invention provides apparatus and methods for dissecting and harvesting graft blood vessels from a patient.

The present invention is useful, inter alia, in procedures where the target tissue or organ is, or can be, flooded or submerged with an electrically conductive fluid, such as isotonic saline. In addition, tissues which may be treated by the system and method of the present invention further include, but are not limited to, tissues of the heart, chest, knee, shoulder, ankle, hip, elbow, hand or foot; as well as prostate tissue, leiomyomas (fibroids) located within the uterus, gingival tissues and mucosal tissues located in the mouth, tumors, scar tissue, myocardial tissue, collagenous tissue within the eye; together with epidermal and dermal tissues on the surface of the skin. The present invention is also useful for resecting tissue within accessible sites of the body that are suitable for electrode loop resection, such as the resection of prostate tissue, leiomyomas (fibroids) located within the uterus, or other tissue to be removed from the body.

The present invention is also useful for procedures in the head and neck, such as the ear, mouth, throat, pharynx, larynx, esophagus, nasal cavity, and sinuses. These procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for cutting, resection, ablation and/or hemostasis of tissue in procedures for treating snoring and obstructive sleep apnea (e.g., UPPP procedures), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies, myringotomies, or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck region, e.g., the removal of pigmentations, vascular lesions, scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

The present invention is also useful for harvesting blood vessels, such as a blood vessel to be used as a graft vessel during the CABG procedure, e.g., the saphenous vein and the internal mammary artery (IMA). One or more embodiments of the invention may be used as follows: i) to access the blood vessel to be harvested, e.g., by opening the leg to access the saphenous vein, or opening the chest (either via a longitudinal incision of the sternum (median sternotomy) during an open-chest procedure, or during a minimally invasive intercostal (closed-chest) procedure); ii) to dissect the blood vessel to be harvested from the surrounding connective tissue along at least a portion of its length; and iii) to transect the dissected blood vessel at a first position only in the case of a pedicled graft (IMA), or at the first position and at a second position in the case of a free graft (saphenous vein). In each case i) to iii), as well as for other embodiments of the invention, the procedure involves removal of tissue by a cool ablation procedure in which a high frequency voltage is applied to an active electrode in the vicinity of a target tissue, typically in the presence of an electrically conductive fluid. The cool ablation procedure of the invention is described fully elsewhere herein. The electrically conductive fluid may be a bodily fluid such as blood, intracellular fluid of the target tissue, or an extraneous fluid, such as isotonic saline, delivered to the target tissue during the procedure. The present invention is also useful for coagulating blood or blood vessels, for example, to minimize bleeding in the sternum during an open-chest procedure.

Although certain parts of this disclosure are directed specifically to creating incisions for accessing a patient's thoracic cavity and the harvesting and dissection of blood vessels within the body during a CABG procedure, systems and methods of the invention are equally applicable to other procedures involving other organs or tissues of the body, including minimally invasive procedures, open procedures, intravascular procedures, urological procedures, laparascopy, arthroscopy, thoracoscopy, various cardiac procedures, cosmetic surgery, orthopedics, gynecology, otorhinolaryngology, spinal and neurologic procedures, oncology, and the like.

In methods of the present invention, high frequency (RF) electrical energy is usually applied to one or more active electrodes in the presence of an electrically conductive fluid to remove and/or modify target tissue, an organ, or a body structure. Depending on the specific procedure, the present invention may be used to: (1) create incisions in tissue; (2) dissect or harvest tissue; (3) volumetrically remove tissue or cartilage (i.e., ablate or effect molecular dissociation of the tissue); (4) cut, transect, or resect tissue or an organ (e.g., a blood vessel); (5) create perforations or holes within tissue; and/or (6) coagulate blood and severed blood vessels.

In one method of the present invention, the tissue structures are incised by volumetrically removing or ablating tissue along a cutting path. In this procedure, a high frequency voltage difference is applied between one or more active electrode (s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has a relatively high electrical impedance, it minimizes the current flow into the electrically conductive fluid. Within the vaporized fluid a plasma is formed, and charged particles (e.g., electrons) cause the localized molecular dissociation or disintegration of components of the target tissue, to a depth of perhaps several cell layers. This molecular dissociation results in the volumetric removal of tissue from the target site. This ablation process, which typically subjects the target tissue to a temperature in the range of 40° C. to 70° C., can be precisely controlled to effect the removal of tissue to a depth as little as about 10 microns, with little or no thermal or other damage to surrounding tissue. This cold ablation phenomenon has been termed Coblation®.

While not being bound by theory, applicant believes that the principle mechanism of tissue removal in the Coblation® mechanism of the present invention is energetic electrons or ions that have been energized in a plasma adjacent to the active electrode(s). When a liquid is heated sufficiently that atoms vaporize from the liquid at a greater rate than they recondense, a gas is formed. When the gas is heated sufficiently that the atoms collide with each other and electrons are removed from the atoms in the process, an ionized gas or plasma is formed. (A more complete description of plasmas (the so-called "fourth state of matter") can be found in Plasma Physics, by R. J. Goldston and P. H. Rutherford of the Plasma Physics Laboratory of Princeton University (1995), the complete disclosure of which is incorporated herein by reference.) When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating and ionizing a gas by driving an electric current through it, or by transmitting radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; electrical insulators over the electrodes; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose tissue) contains a large amount of lipid material having double bonds, the breakage of which requires an energy level substantially higher than 4 eV to 5 eV. Accordingly, the present invention can be configured such that lipid components of adipose tissue are selectively not ablated. Of course, the present invention may be used to effectively ablate cells of adipose tissue such that the inner fat content of the cells is released in a liquid form. Alternatively, the invention can be configured (e.g., by increasing the voltage or changing the electrode configuration to increase the current density at the electrode tips) such that the double bonds of lipid materials are readily broken leading to molecular dissociation of lipids into low molecular weight condensable gases, generally as described hereinabove. A more complete description of the Coblation® phenomenon can be found in commonly assigned U.S. Pat. No. 5,683,366 and co-pending U.S. patent application Ser. No. 09/032,375, filed Feb. 27, 1998, the complete disclosures of which are incorporated herein by reference.

Methods of the present invention typically involve the application of high frequency (RF) electrical energy one or more active electrodes in the presence of an electrically conductive fluid to remove (i.e., resect, incise, perforate, cut, or ablate) a target tissue, structure, or organ; and/or to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an active electrode sufficient to effect molecular dissociation or disintegration of the tissue; and a coagulation mode, wherein a second, lower voltage is applied to an active electrode (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to both coagulate with the coagulation electrode(s), and to ablate or contract tissue with the active electrode(s). In other embodiments, the power supply is combined with the coagulation probe such that the coagulation electrode is used when the power supply is in the coagulation mode (low voltage), and the active electrode(s) are used when the power supply is in the ablation mode (higher voltage).

In one method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described above. During this process, vessels within the tissue are severed. Smaller vessels may be automatically sealed with the system and method of the present invention. Larger vessels and those with a higher flow rate, such as arterial vessels, may not be automatically sealed in the ablation mode. In these cases, the severed vessels may be sealed by actuating a control (e.g., a foot pedal) to reduce the voltage of the power supply into the coagulation mode. In this mode, the active electrodes may be pressed against the severed vessel to provide sealing and/or coagulation of the vessel. Alternatively, a coagulation electrode located on the same or a different probe may be pressed against the severed vessel. Once the vessel is adequately sealed, the surgeon may activate a control (e.g., another foot pedal) to increase the voltage of the power supply back into the ablation mode.

The present invention is also useful for removing or ablating tissue around nerves, such as spinal, or cranial nerves, e.g., the hypoglossal nerve, the optic nerve, facial nerves, vestibulocochlear nerves and the like. This is particularly advantageous when removing tissue that is located close to nerves. One of the significant drawbacks with the conventional RF devices, scalpels, and lasers is that these devices do not differentiate between the target tissue and the surrounding nerves or bone. Therefore, the surgeon must be extremely careful during these procedures to avoid damage to the nerves within and around the target tissue. In the present invention, the Coblation® process for removing tissue results in no, or extremely small amounts, of collateral tissue damage, as described above. This allows the surgeon to remove tissue close to a nerve without causing collateral damage to the nerve fibers and surrounding tissue.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue that is treated. The system of the present invention measures the electrical properties of the tissue at the tip of the probe with one or more active electrode(s). These electrical properties may include electrical conductivity at one, several, or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode(s) either individually or to the complete array of electrodes, if and when the tissue encountered at the tip or working end of the probe is normal tissue based on the measured electrical properties.

In one embodiment, the current limiting elements are configured such that the active electrodes will shut down or turn off when the electrical impedance reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to target tissue, will continue to conduct electric current to the return electrode. This selective ablation or removal of lower impedance tissue in combination with the Coblation® mechanism of the present invention allows the surgeon to precisely remove tissue around nerves or bone. Applicant has found that the present invention is capable of volumetrically removing tissue closely adjacent to nerves without impairing the function of the nerves, and without significantly damaging the tissue of the epineurium.

The present invention can be also be configured to create an incision in a bone of the patient. For example, the systems of the present invention can be used to create an incision in the sternum for access to the thoracic cavity. Applicant has found that the Coblation® mechanism of the present invention allows the surgeon to precisely create an incision in the sternum while minimizing or preventing bone bleeding. The high frequency voltage is applied between the active electrode(s) and the return electrode(s) to volumetrically remove the bone from a specific site targeted for the incision. As the active electrode(s) are passed through the incision in the bone, the sides of the active electrodes (or a third coagulation electrode) slidingly contact the bone surrounding the incision to provide hemostasis in the bone. A more complete description of such coagulation electrodes can be found in U.S. patent application Ser. No. 09/162,117, filed Sep. 28, 1998, the complete disclosure of which is incorporated herein by reference.

The present invention can also be used to dissect and harvest blood vessels from the patient's body during a CABG procedure. The system of the present invention allows a surgeon to dissect and harvest blood vessels, such as the right or left IMA, the gastroepiploic artery, radial artery or a saphenous vein, while concurrently providing hemostasis at the harvesting site. In some embodiments, a first high frequency voltage, can be delivered in an ablation mode to effect molecular disintegration of connective tissue adjacent to the blood vessel targeted for harvesting; and a second, lower voltage can be delivered to achieve hemostasis of the connective tissue adjacent to the blood vessel. In other embodiments, the targeted blood vessel can be transected at one or more positions along its length, and one or more coagulation electrode(s) can be used to seal the transected blood vessel at the site of transection. The coagulation electrode(s) may be configured such that a single voltage can be applied to the active electrodes to ablate the tissue and to coagulate the blood vessel and target site.

The present invention also provides systems, apparatus, and methods for selectively removing tumors or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team, or viable cancerous cells to other locations within the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the active electrode(s) and one or more return electrode(s) to volumetrically remove at least a portion of the tissue cells in the tumor or lesion by the molecular dissociation of tissue components into non-condensable gases. The high frequency voltage is preferably selected to effect controlled removal of these tissue cells while minimizing substantial tissue necrosis to surrounding or underlying tissue. A more complete description of this phenomenon can be found in copending U.S. patent application Ser. No. 09/109,219, filed Jun. 30, 1998, the complete disclosure of which is incorporated herein by reference.

A current flow path between the active electrode(s) and the return electrode(s) may be generated by submerging the tissue site in an electrically conductive fluid (e.g., within a viscous fluid, such as an electrically conductive gel) or by directing an electrically conductive fluid along a fluid path to the target site (i.e., a liquid, such as isotonic saline, or a gas, such as argon). This latter method is particularly effective in a dry field procedure (i.e., the tissue is not submerged in fluid). The use of a conductive gel allows a slower, more controlled delivery rate of conductive fluid as compared with a liquid or a gas. In addition, the viscous nature of the gel may allow the surgeon to more easily contain the gel around the target site (e.g., as compared with containment of isotonic saline). A more complete description of an exemplary method of directing electrically conductive fluid between the active and return electrodes is described in U.S. Pat. No. 5,697,281, the full disclosure of which is incorporated herein by reference. Alternatively, the body's natural conductive fluids, such as blood, may be sufficient to establish a conductive path between the return electrode(s) and the active electrode(s), and to provide the conditions for establishing a vapor layer, as described above. However, conductive fluid that is introduced into the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the tissue at or adjacent to the target site.

In some embodiments of the invention, an electrosurgical probe includes an electrode support for electrically isolating the active electrode(s) from the return electrode, and a fluid delivery port or outlet for directing an electrically conductive fluid to the target site or to the distal end of the probe. The electrode support and the fluid outlet may be recessed from an outer surface of the instrument to confine the electrically conductive fluid to the region immediately surrounding the electrode support. In addition, a shaft of the instrument may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the tissue at the treatment site throughout the procedure, thereby reducing any thermal damage that might otherwise occur if the vapor layer were extinguished due to a lack of conductive fluid. Provision of the electrically conductive fluid around the target site also helps to maintain the tissue temperature at desired levels.

The electrically conductive fluid should have a threshold conductivity to provide a suitable conductive path between the return electrode and the active electrode(s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

An electrosurgical probe or instrument of the invention typically includes a shaft having a proximal end and a distal end, and one or more active electrode(s) disposed at the shaft distal end. The shaft serves to mechanically support the active electrode(s) and permits the treating physician to manipulate the shaft distal end via a handle attached to the proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually have one or more wires, electrode connectors, leads, or other conductive elements running axially therethrough, to permit connection of the electrode(s) to a connection block located at the proximal end of the instrument. The connection block is adapted for coupling the electrode(s) to the power supply or controller. Typically, the connection block is housed within the handle of the probe.

The shaft may assume various configurations. For minimally-invasive procedures of the heart, the shaft will have a suitable diameter and length for the surgeon to reach the target site (e.g., the left or right IMA). Accordingly, the shaft typically has a length in the range of about 5 cm to 30 cm, and a diameter in the range of about 0.5 mm and 10 mm. Specific shaft designs will be described in detail in connection with the Drawings hereinafter.

The present invention may use a single active electrode or a plurality of electrodes distributed across a contact surface of a probe (e.g., in a linear fashion). In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The active electrodes may be independently current-limited by isolating the terminals from each other and connecting each terminal to a separate power source that is isolated from the other active electrodes. Alternatively, the active electrodes may be connected to each other at either the proximal or distal ends of the probe to form a single wire that couples to a power source.

In one configuration, each individual active electrode is electrically insulated from all other active electrodes within the probe and is connected to a power source which is isolated from each of the other active electrodes in the array, or to circuitry which limits or interrupts current flow to the active electrode when low resistivity material causes a low impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the probe, connectors, cable, power supply or along the conductive path from the power supply to the distal tip of the probe. Alternatively, the resistance and/or capacitance may occur on the surface of the active electrode(s) due to oxide layers which form selected active electrodes (e.g., titanium or a resistive coating on the surface of metal, such as platinum).

The distal end of the probe may comprise many independent active electrodes designed to deliver electrical energy in the vicinity of the distal end. The selective application of electrical energy to the conductive fluid is achieved by connecting each individual active electrode and the return electrode to a power source having independently controlled or current limited channels. The return electrode(s) may comprise a single tubular member of electrically conductive material at the distal end of the probe proximal to the active electrode(s) The same tubular member of electrically conductive material may also serve as a conduit for the supply of the electrically conductive fluid between the active and return electrodes. The application of high frequency voltage between the return electrode(s) and the active electrode(s) results in the generation of high electric field intensities at the distal tip of the active electrode(s), with conduction of high frequency current from each active electrode to the return electrode. The current flow from each active electrode to the return electrode(s) is controlled by either active or passive means, or a combination thereof, to deliver electrical energy to the surrounding conductive fluid while minimizing energy delivery to surrounding (non-target) tissue.

The application of a suitable high frequency voltage between the return electrode(s) and the active electrode(s) for appropriate time intervals effects cutting, removing, ablating, shaping, contracting or otherwise modifying the target tissue. In one embodiment, the tissue volume over which energy is dissipated (i.e., over which a high current density exists) may be precisely controlled, for example, by the use of a multiplicity of small active electrodes whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per active electrode) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$. In one embodiment the probe may include a plurality of relatively small active electrodes disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The portion of the electrode support on which the active electrode(s) are mounted generally defines a tissue treatment surface of the probe. The area of the tissue treatment surface can vary widely, and the tissue treatment surface can assume a variety of geometries, with particular areas and geometries being selected for specific applications. The area of the tissue treatment surface can range from about 0.25 $mm^2$ to 75 $mm^2$, usually being from about 0.5 $mm^2$ to 40 $mm^2$. The geometries of the active electrode(s) can be planar, concave, convex, hemispherical, conical, a linear "in-line" array, or virtually any other regular or irregular shape. Most commonly, the active electrode(s) will be located at the shaft distal end of the electrosurgical probe, frequently having planar, disk-shaped, or hemispherical surfaces for use in reshaping procedures, ablating, cutting, dissecting organs, coagulating, or transecting blood vessels. The active electrode(s) may be arranged terminally or laterally on the electrosurgical probe (e.g., in the manner of a scalpel or a blade). However, it should be clearly understood that the active electrode of the invention does not cut or sever tissue mechanically as for a scalpel blade, but rather by the localized molecular dissociation of tissue components due to application of high frequency electric current to the active electrode. In one embodiment, a distal portion of the shaft may be flattened or compressed laterally (e.g., FIGS. 32A–32C). A probe having a laterally compressed shaft may facilitate access to certain target sites or body structures during various surgical procedures.

In embodiments having a plurality of active electrodes, it should be clearly understood that the invention is not limited to electrically isolated active electrodes. For example, a plurality of active electrodes may be connected to a single lead that extends through the probe shaft and is coupled to a high frequency power supply. Alternatively, the probe may incorporate a single electrode that extends directly through the probe shaft or is connected to a single lead that extends to the power source. The active electrode may have a planar or blade shape, a screwdriver or conical shape, a sharpened point, a ball shape (e.g., for tissue vaporization and desiccation), a hook shape for snaring and desiccating tissue, a twizzle shape (for vaporization and needle-like cutting), a spring shape (for rapid tissue debulking and desiccation), a twisted metal shape, an annular or solid tube shape, or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode, or the like.

In one embodiment, the probe comprises a single blade active electrode that extends from an insulating support member, spacer, or electrode support, e.g., a ceramic or silicone rubber spacer located at the distal end of the probe. The insulating support member may be a tubular structure or a laterally compressed structure that separates the blade active electrode from a tubular or annular return electrode positioned proximal to the insulating member and the active electrode. The blade electrode may include a distal cutting edge and sides which are configured to coagulate the tissue as the blade electrode advances through the tissue. In yet another embodiment, the catheter or probe includes a single active electrode that can be rotated relative to the rest of the catheter body, or the entire catheter may be rotated relative to the electrode lead(s). The single active electrode can be positioned adjacent the abnormal tissue and energized and rotated as appropriate to remove or modify the target tissue.

The active electrode(s) are preferably supported within or by an insulating support member positioned near the distal end of the instrument shaft. The return electrode may be located on the instrument shaft, on another instrument, or on the external surface of the patient (i.e., a dispersive pad). For certain procedures, the close proximity of nerves and other sensitive tissue makes a bipolar design more preferable because this minimizes the current flow through non-target tissue and surrounding nerves. Accordingly, the return electrode is preferably either integrated with the instrument body, or located on another instrument. The proximal end of the probe typically includes the appropriate electrical connections for coupling the return electrode(s) and the active electrode(s) to a high frequency power supply, such as an electrosurgical generator.

One exemplary power supply of the present invention delivers a high frequency current selectable to generate average power levels ranging from several milliwatts to tens of watts per electrode, depending on the volume of target tissue being treated, and/or the maximum allowed temperature selected for the instrument tip. The power supply allows the user to select the voltage level according to the specific requirements of a particular otologic procedure, neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power supply having a higher operating frequency, e.g., 300 kHz to 500 kHz may be used in certain procedures in which stray low frequency currents may be problematic. A description of one suitable power supply can be found in patent applications Ser. Nos. 09/058,571 and 09/058,336, filed Apr. 10, 1998, the complete disclosure of both applications are incorporated herein by reference for all purposes.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. The RMS (root mean square) voltage applied will usually be in the range from about 5 volts to 1000 volts, preferably being in the range from about 10 volts to 500 volts depending on the active electrode size, the operating frequency, and the operation mode of the particular procedure or desired effect on the tissue (e.g., contraction, coagulation, cutting or ablation). Typically, the peak-to-peak voltage for ablation or cutting will be in the range of 10 volts to 2000 volts and preferably in the range of 200 volts to 1800 volts, and more preferably in the range of about 300 volts to 1500 volts, often in the range of about 500 volts to 900 volts peak to peak (again, depending on the electrode size, the operating frequency and the operation mode). Lower peak-to-peak voltages will be used for tissue coagulation or collagen contraction and will typically be in the range from 50 to 1500, preferably 100 to 1000, and more preferably 120 to 600 volts peak-to-peak.

The voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The power supply may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, copending U.S. application Ser. No. 09/058,336, filed Apr. 10, 1998, the complete disclosure of which is incorporated herein by reference.

The power supply may also be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from the active electrode into the low resistance medium (e.g., saline irrigant or blood).

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, purulent fluid, the gaseous products of ablation, or the like. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, co-pending patent application Ser. No. 09/010,382, filed Jan. 21, 1998, the complete disclosure of which is incorporated herein by reference.

During a surgical procedure, the distal end of the instrument and the active electrode(s) may be maintained at a small distance away from the target tissue surface. This small spacing allows for the continuous flow of electrically conductive fluid into the interface between the active electrode(s) and the target tissue surface. The continuous flow of the electrically conductive fluid helps to ensure that the thin vapor layer will remain between the active electrode(s) and the tissue surface. In addition, dynamic movement of the active electrode(s) over the tissue site allows the electrically conductive fluid to cool the tissue underlying and surrounding the target tissue to minimize thermal damage to this surrounding and underlying tissue. Accordingly, the electrically conductive fluid may be cooled to facilitate the cooling of the tissue. Typically, the active electrode(s) will be about 0.02 mm to 2 mm from the target tissue and preferably about 0.05 mm to 0.5 mm during the ablation process. One method of maintaining this space is to move, translate and/or rotate the probe transversely relative to the tissue, i.e., for the operator to use a light brushing motion, to maintain a thin vaporized layer or region between the active electrode and the tissue. Of course, if coagulation or collagen shrinkage of a deeper region of tissue is necessary (e.g., for sealing a bleeding vessel embedded within the tissue), it may be desirable to press the active electrode(s) against the tissue to effect joulean heating therein.

Referring to FIG. 1, an exemplary electrosurgical system 11 for cutting, ablating, resecting, or otherwise modifying tissue will now be described in detail. Electrosurgical system 11 generally comprises an electrosurgical handpiece or probe 10 connected to a power supply 28 for providing high frequency voltage to a target site, and a fluid source 21 for supplying electrically conductive fluid 50 to probe 10. In addition, electrosurgical system 11 may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 211 (see FIG. 2) in the probe 10 for aspirating the target site.

As shown, probe 10 generally includes a proximal handle 19 and an elongate shaft 18 having one or more active electrodes 58 at its distal end. A connecting cable 34 has a connector 26 for electrically coupling the active electrodes 58 to power supply 28. In embodiments having a plurality of active electrodes, active electrodes 58 are electrically isolated from each other and the terminal of each active electrode 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site.

Power supply 28 has an operator controllable voltage level adjustment 30 to change the applied voltage level, which is observable at a voltage level display 32. Power supply 28 also includes first, second, and third foot pedals 37, 38, 39 and a cable 36 which is removably coupled to power supply 28. The foot pedals 37, 38, 39 allow the surgeon to remotely adjust the energy level applied to active electrode(s) 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the ablation mode. In the ablation mode, a sufficient voltage is applied to the active electrodes to establish the requisite conditions for molecular dissociation of the tissue (i.e., vaporizing a portion of the electrically conductive fluid, ionizing the vapor layer and accelerating charged particles against the tissue). As discussed above, the requisite voltage level for ablation will vary depending on the number, size, shape and spacing of the electrodes, the distance in which the electrodes extend from the support member, etc. When the surgeon is using the power supply in the ablation mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient means for controlling the power supply while manipulating the probe during a surgical procedure.

In the coagulation mode, the power supply 28 applies a low enough voltage to the active electrode(s) (or the coagulation electrode) to avoid vaporization of the electrically conductive fluid and subsequent molecular dissociation of the tissue. The surgeon may automatically toggle the power supply between the ablation and coagulation modes by alternately stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in Provisional Patent Application No. 60/062,997, filed Oct. 23, 1997, previously incorporated herein by reference.

Figure 2:
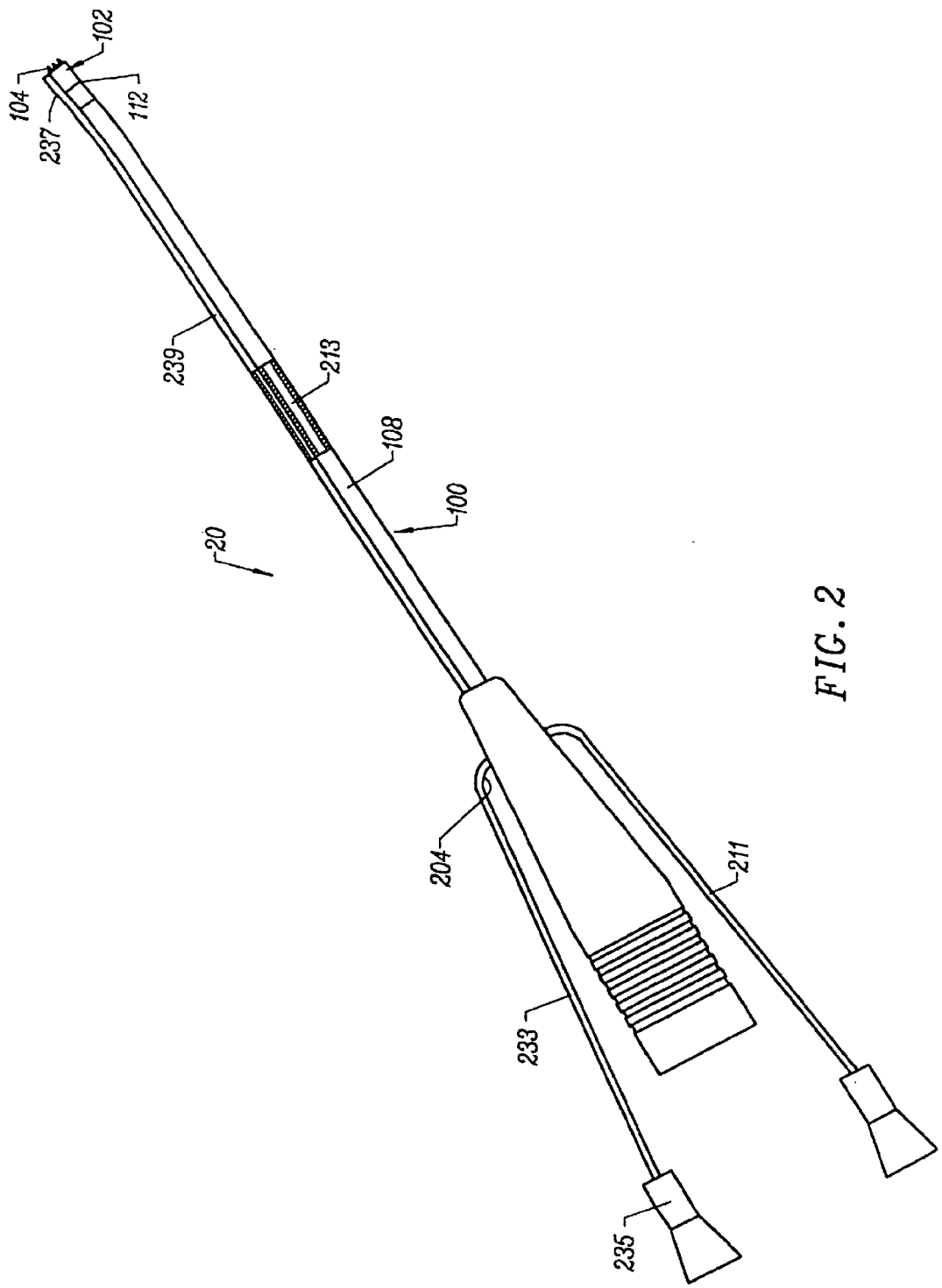
FIG. 2 is a side view of an electrosurgical probe according to the present invention.

FIG. 2 shows an electrosurgical probe 20 according to one embodiment of the invention. Probe 20 may be used in conjunction with a system similar or analogous to system 11 (FIG. 1). As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 may comprise a plastic material that is easily molded into the shape shown in FIG. 3, or shaft 100 may comprise an electrically conductive material, usually a metal, such as tungsten, stainless steel alloys, platinum or its alloys, titanium or its alloys, molybdenum or its alloys, and nickel or its alloys. In the latter case (i.e., shaft 100 is electrically conductive), probe 20 includes an electrically insulating jacket 108, which is typically formed as one or more electrically insulating sheaths or coatings, such as polytetrafluoroethylene, polyimide, and the like. The provision of electrically insulating jacket 108 over shaft 100 prevents direct electrical contact between the metal shaft and any adjacent body structure or the surgeon. Such direct electrical contact between a body structure (e.g., heart, bone, nerves, skin, or other blood vessels) and an exposed electrode could result in unwanted heating and necrosis of the structure at the point of contact.

Handle 204 typically comprises a plastic material that is easily molded into a suitable shape for handling by the surgeon. Handle 204 defines an inner cavity (not shown) that houses an electrical connections unit 250 (FIG. 5), and provides a suitable interface for coupling probe 20 to power supply 28 via an electrical connecting cable. Electrode support member 102 extends from the distal end of shaft 100 (usually about 1 mm to 20 mm), and provides support for an active electrode or a plurality of electrically isolated active electrodes 104. In the specific configuration shown in FIG. 2, probe 20 includes a plurality of active electrodes. As shown in FIG. 2, a fluid tube 233 extends through an opening in handle 204, and includes a connector 235 for connection to a fluid supply source for supplying electrically conductive fluid to the target site. Fluid tube 233 is coupled to a distal fluid tube 239 that extends along the outer surface of shaft 100 to an opening 237 at the distal end of the probe 20, as will be discussed in detail below. Of course, the invention is not limited to this configuration. For example, fluid tube 233 may extend through a single lumen (not shown) in shaft 100, it may be coupled to a plurality of lumens (also not shown) that extend through shaft 100 to a plurality of openings at its distal end, or the fluid tube may be completely independent of shaft 100. Probe 20 may also include a valve or equivalent structure for controlling the flow rate of the electrically conductive fluid to the target site.

Figure 3:
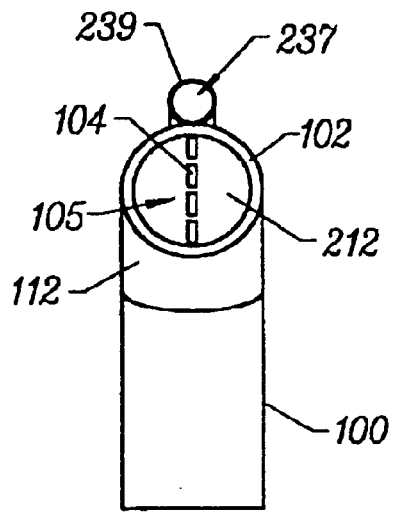
FIG. 3 is an end view of the distal portion of the probe of FIG. 2.
Figure 4:
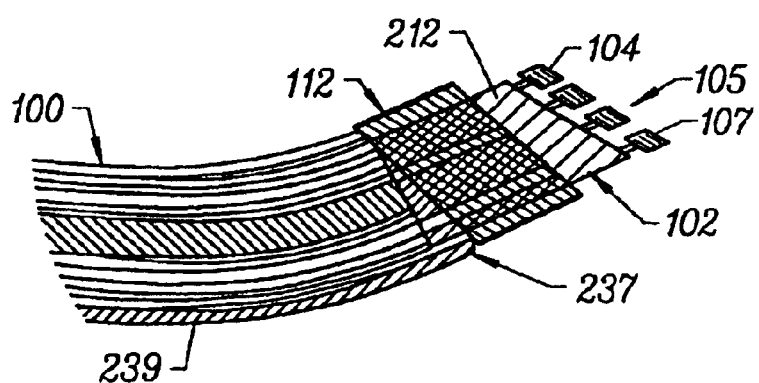
FIG. 4 is a cross sectional view of the distal portion of the electrosurgical probe of FIG. 2.

As shown in FIGS. 3 and 4, electrode support member 102 has a substantially planar tissue treatment surface 212 and comprises a suitable insulating material (e.g., a ceramic or glass material, such as alumina, zirconia and the like) which could be formed at the time of manufacture in a flat, hemispherical or other shape according to the requirements of a particular procedure. The preferred support member material is alumina (Kyocera Industrial Ceramics Corporation, Elkgrove, Ill.), because of its high thermal conductivity, good electrically insulative properties, high flexural modulus, resistance to carbon tracking, biocompatibility, and high melting point. Electrode support member 102 is adhesively joined to a tubular support member (not shown) that extends most or all of the distance between support member 102 and the proximal end of probe 20. The tubular member preferably comprises an electrically insulating material, such as an epoxy or silicone-based material.

In a preferred construction technique, active electrodes 104 extend through pre-formed openings in the support member 102 so that they protrude above tissue treatment surface 212 by the desired distance. The electrodes are then bonded to the tissue treatment surface 212 of support member 102, typically by an inorganic sealing material. The sealing material is selected to provide effective electrical insulation, and good adhesion to both support member 102 and active electrodes 104. In one embodiment, active electrodes 104 comprise an electrically conducting, corrosion resistant metal, such as platinum or titanium. The sealing material additionally should have a compatible thermal expansion coefficient and a melting point well below that of platinum or titanium and alumina or zirconia, typically being a glass or glass ceramic.

In the embodiment shown in FIGS. 2–5, probe 20 includes a return electrode 112 for completing the current path between active electrodes 104 and a high frequency power supply 28 (see FIG. 1). As shown, return electrode 112 preferably comprises an annular conductive band coupled to the distal end of shaft 100 at a location proximal to tissue treatment surface 212 of electrode support member 102, typically about 0.5 mm to 10 mm proximal to surface 212, and more preferably about 1 mm to 10 mm proximal to surface 212. Return electrode 112 is coupled to a connector 258 that extends to the proximal end of probe 20, where it is suitably connected to power supply 28 (FIGS. 1 and 2).

As shown in FIG. 2, return electrode 112 is not directly connected to active electrodes 104. To complete this current path so that active electrodes 104 are electrically connected to return electrode 112, electrically conductive fluid (e.g., isotonic saline) is caused to flow therebetween. In the representative embodiment, the electrically conductive fluid is delivered through an external fluid tube 239 to opening 237, as described above (FIGS. 2 and 4). Alternatively, the fluid may be continuously delivered by a fluid delivery element (not shown) that is separate from probe 20.

In alternative embodiments, the fluid path may be formed in probe 20 by, for example, an inner lumen or an annular gap between the return electrode and a tubular support member within shaft 100 (not shown). This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in U.S. Pat. No. 5,697,281, filed on Jun. 7, 1995, the complete disclosure of which is incorporated herein by reference.

Referring to FIGS. 3 and 4, the electrically isolated active electrodes 104 are preferably spaced from each other and aligned to form a linear array 105 of electrodes for cutting a substantially linear incision in the tissue. The tissue treatment surface and individual active electrodes 104 will usually have dimensions within the ranges set forth above. Active electrodes 104 preferably have a distal edge 107 to increase the electric field intensities around terminals 104, and to facilitate cutting of tissue. Thus, active electrodes 104 have a screwdriver shape in the representative embodiment of FIGS. 2–4. In one representative embodiment, the tissue treatment surface 212 has a circular cross-sectional shape with a diameter in the range of about 1 mm to 30 mm, usually about 2 mm to 20 mm. The individual active electrodes 104 preferably extend outward from tissue treatment surface 212 by a distance of about 0.1 mm to 8 mm, usually about 1 mm to 4 mm. Applicant has found that this configuration increases the high electric field intensities and associated current densities around active electrodes 104 to facilitate the ablation of tissue as described in detail above.

Probe 20 may include a suction or aspiration lumen 213 (see FIG. 2) within shaft 100 and a suction tube 211 (FIG. 2) for aspirating tissue, fluids and/or gases from the target site. In this embodiment, the electrically conductive fluid generally flows from opening 237 of fluid tube 239 radially inward and then back through one or more openings (not shown) in support member 102. Aspirating the electrically conductive fluid during surgery allows the surgeon to see the target site, and it prevents the fluid from flowing into the patient's body (e.g., the thoracic cavity). This aspiration should be controlled, however, so that the conductive fluid maintains a conductive path between the active electrode(s) and the return electrode. In some embodiments, the probe 20 will also include one or more aspiration electrode(s) (not shown) coupled to the aspiration lumen for inhibiting clogging during aspiration of tissue fragments from the surgical site. A more complete description of these embodiments can be found in commonly assigned U.S. patent application Ser. No. 09/010,382, filed Jan. 21, 1998, the complete disclosure of which is incorporated herein by reference for all purposes.

Figure 5:
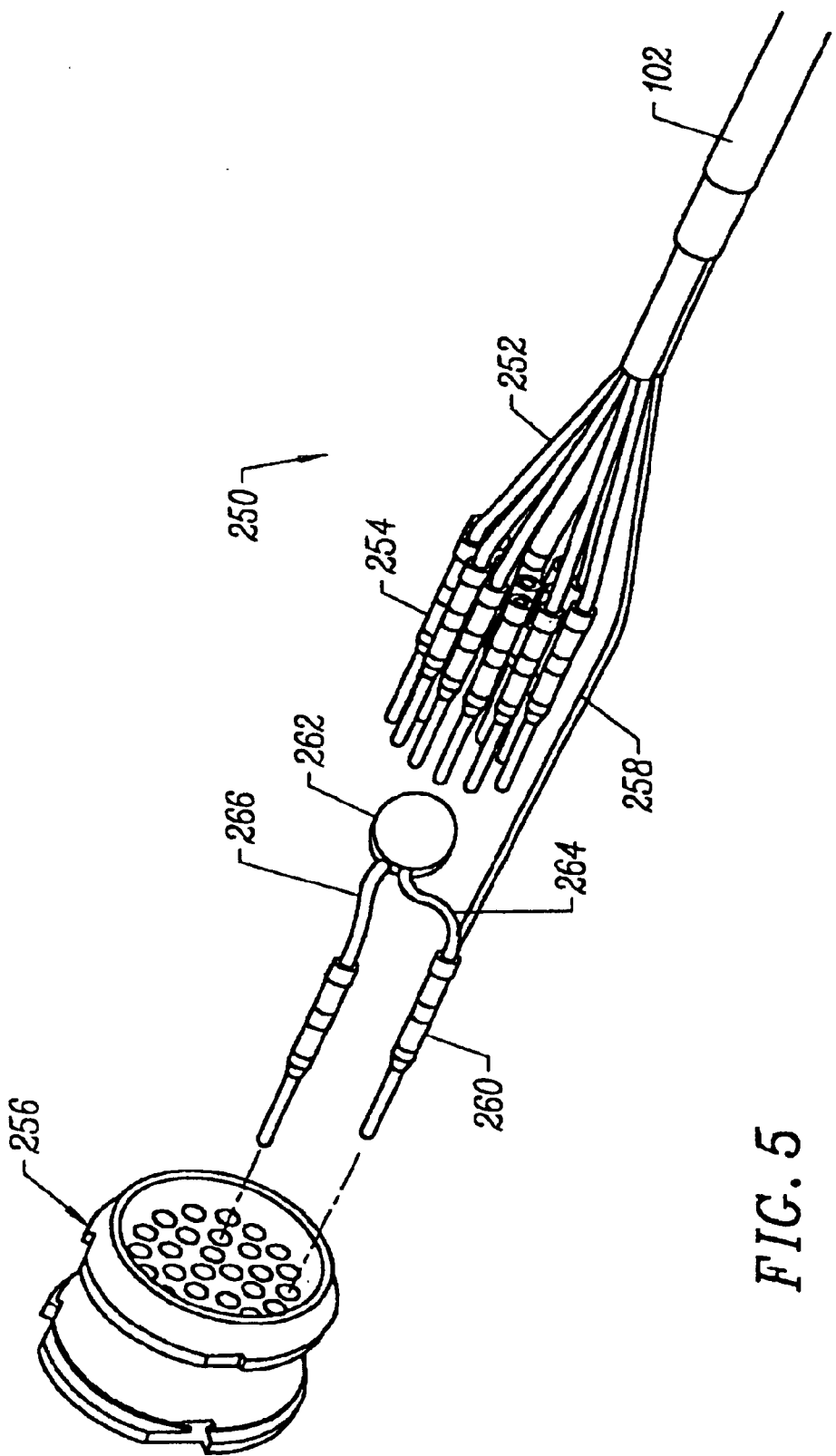
FIG. 5 is an exploded view of a proximal portion of the electrosurgical probe.

FIG. 5 illustrates the electrical connections 250 within handle 204 for coupling active electrodes 104 and return electrode 112 to the power supply 28. As shown, a plurality of wires 252 extend through shaft 100 to couple electrodes 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, probe 20 further includes an identification element that is characteristic of the particular electrode assembly so that the same power supply 28 can be used for different electrosurgical operations. In one embodiment, for example, probe 20 includes a voltage reduction element or a voltage reduction circuit for reducing the voltage applied between the active electrodes 104 and the return electrode 112. The voltage reduction element serves to reduce the voltage applied by the power supply so that the voltage between the active electrodes and the return electrode is low enough to avoid excessive power dissipation into the electrically conductive medium and/or the tissue at the target site. The voltage reduction element primarily allows the electrosurgical probe 10/20 to be compatible with a range of different power supplies that are adapted to apply higher voltages for ablation or vaporization of tissue (e.g., various power supplies or generators manufactured by ArthroCare Corporation, Sunnyvale, Calif.). For contraction of tissue, for example, the voltage reduction element will serve to reduce a voltage of about 100 to 135 volts rms (which corresponds to a setting of 1 on the ArthroCare Model 970 and 980 (i.e., 2000) Generators) to about 45 to 60 volts rms, which is a suitable voltage for contraction of tissue without ablation (e.g., molecular dissociation) of the tissue.

Again with reference to FIG. 5, n the representative embodiment the voltage reduction element is a dropping capacitor 262 which has a first leg 264 coupled to the return electrode wire 258 and a second leg 266 coupled to connector block 256. Of course, the capacitor may be located in other places within the system, such as in, or distributed along the length of, the cable, the power supply, the connector, etc. In addition, it will be recognized that other voltage reduction elements, such as diodes, transistors, inductors, resistors, capacitors or combinations thereof, may be used in conjunction with the present invention. For example, probe 20 may include a coded resistor (not shown) that is constructed to lower the voltage applied between return electrode 112 and active electrodes 104 to a suitable level for contraction of tissue. In addition, electrical circuits may be employed for this purpose.

Alternatively or additionally, the cable 22 that couples the power supply 28 to probe 10/20 may be used as a voltage reduction element. The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor.

Further, it should be noted that various electrosurgical probes of the present invention can be used with a particular power supply that is adapted to apply a voltage within a selected range for a certain procedure or treatment. In which case, a voltage reduction element or circuitry may not be necessary nor desired.

Figure 6:
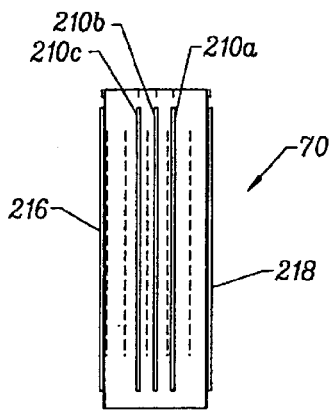
FIG. 6 is an end view of an exemplary electrode support comprising a multi-layer wafer with plated conductors for electrodes.
Figures 7, 8:
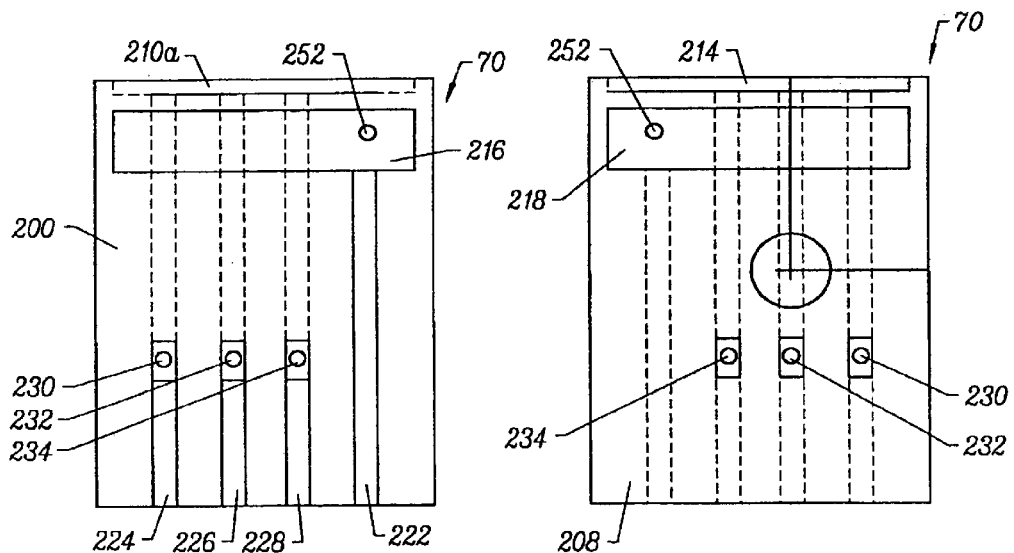
FIGS. 7 and 8 are side views of the electrode support of FIG. 7.

With reference to FIGS. 6–8, electrode support member 70 according to one embodiment includes a multi-layer substrate comprising a suitable high temperature, electrically insulating material, such as ceramic. The multi-layer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise tungsten, and they are co-fired together with the wafer layers to form an integral package. The conductive strips are coupled to external wire connectors by holes or vias that are drilled through the ceramic layers, and plated or otherwise covered with conductive material. A more complete description of such support members 370 can be found in U.S. patent application Ser. No. 08/977,845, filed Nov. 25, 1997, the entire disclosure of which is incorporated herein by reference.

Figure 9A:
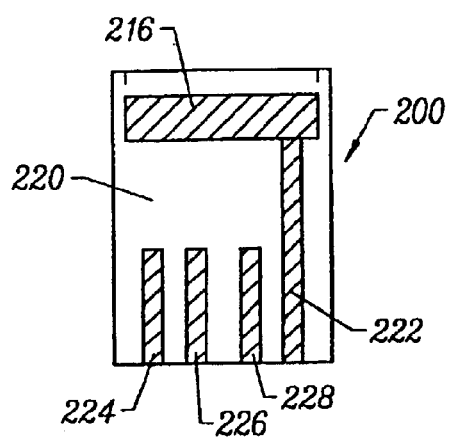
Figure 9B:
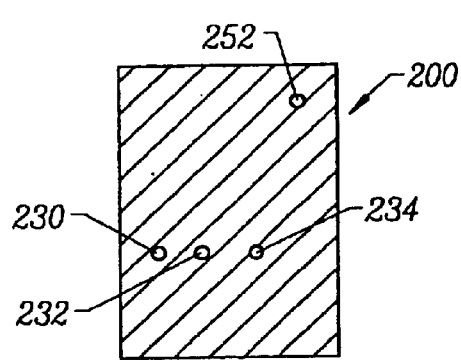

In the representative embodiment, support member 70 comprises five ceramic layers 200, 202, 204, 206, 208 (see FIGS. 6–10), three gold plated active electrodes 210a, 210b, 210c and first and second gold plated return electrodes 216, 218. As shown in FIGS. 9A and 9B, a first ceramic layer 200, which is one of the outer layers of support 70, includes first gold plated return electrode 216 on a lateral surface 220 of layer 200. First ceramic layer 200 further includes a gold conductive strip 222 extending from return electrode 216 to the proximal end of layer 200 for coupling to a lead wire (not shown), and three gold conductive lines 224, 226, 228 extending from a mid-portion of layer 200 to its proximal end. Conductive strips 224, 226, 228 are each coupled to one of the active electrodes 210a, 210b, 210c by conductive holes or vias 230, 232, 234, respectively. As shown, all three vias 230, 232, 234 extend through wafer layer 200.

Figure 10A:
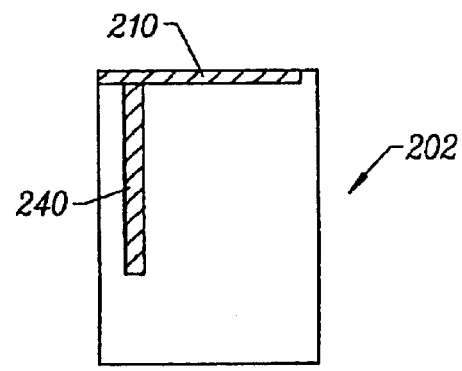
Figure 10B:
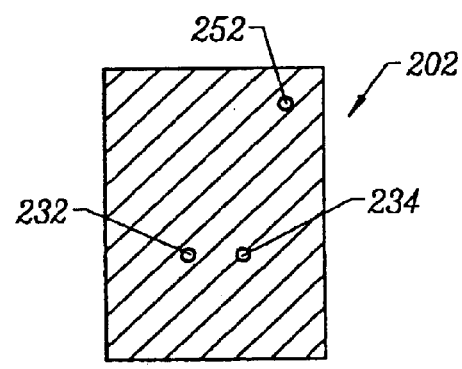
Figure 13:
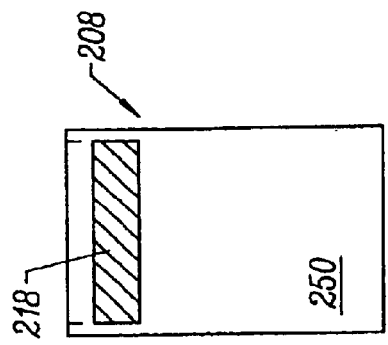
FIG. 13 is a side view of an individual wafer layer.
Figure 12A:
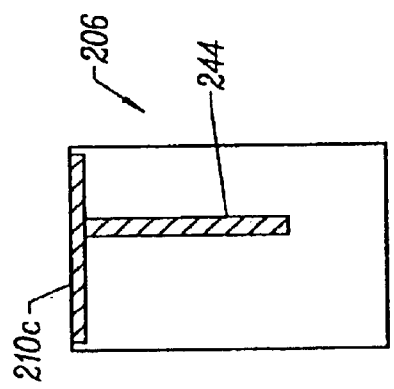
Figure 12B:
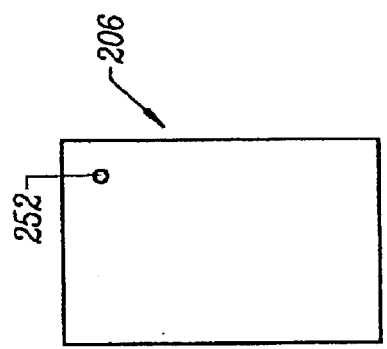
Figure 11A:
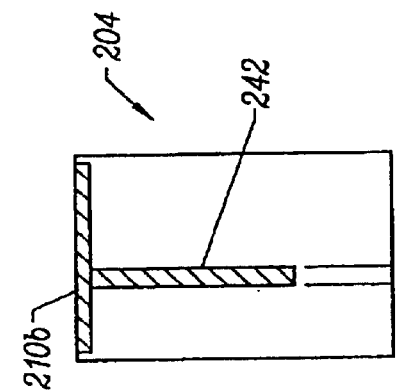
Figure 11B:
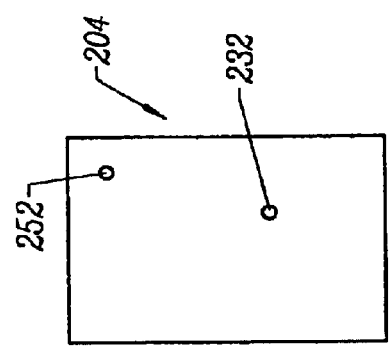

Referring to FIGS. 10A and 10B, a second wafer layer 202 is bonded between first outer wafer layer 200 and a middle wafer layer 204 (See FIGS. 11A and 11B). As shown, first active electrode 210a is attached to the distal surface of second wafer layer 202, and a conductive strip 240 extends to via 230 to couple active electrode 210a to a lead wire. Similarly, wafer layers 204 and 206 (FIGS. 11A, 11B, 12A, and 12B) each have an active electrode 210b, 210c plated to their distal surfaces, and a conductive strip 242, 244, respectively, extending to one of the vias 232, 234, respectively. Note that the vias only extend as far as necessary through the ceramic layers. As shown in FIG. 13, a second outer wafer layer 208 has a second return electrode 218 plated to the lateral surface 250 of layer 208. The second return electrode 218 is coupled directly to the first return electrode 216 through a via 252 extending through the entire ceramic substrate.

Figure 14:
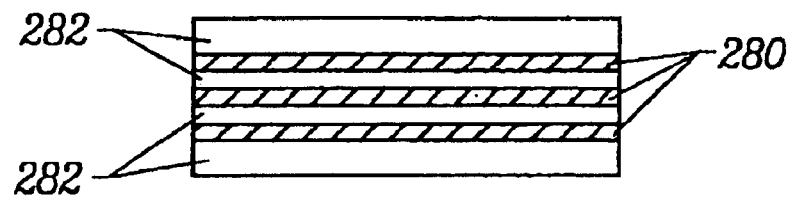
FIGS. 14 and 15 illustrate an alternative multi-layer waftr design according to the present invention.
Figure 15:
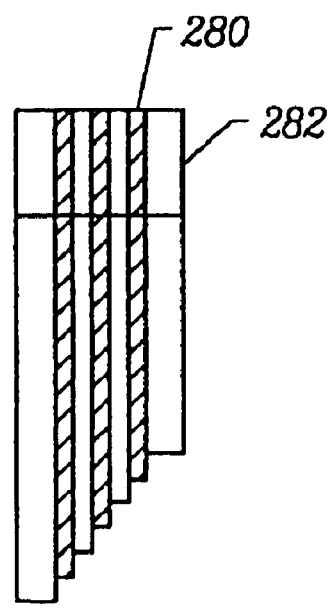

Of course, it will be recognized that a variety of different types of single layer and multi-layer wafers may be constructed according to the present invention. For example, FIGS. 14 and 15 illustrate an alternative embodiment of the multi-layer ceramic wafer, wherein the active electrodes comprise planar strips 280 that are plated or otherwise bonded between the ceramic wafer layers 282. Each of the planar strips 280 has a different length, as shown in FIG. 15, so that the active electrodes can be electrically isolated from each other, and coupled to lead wires by vias (not shown).

Figure 16:
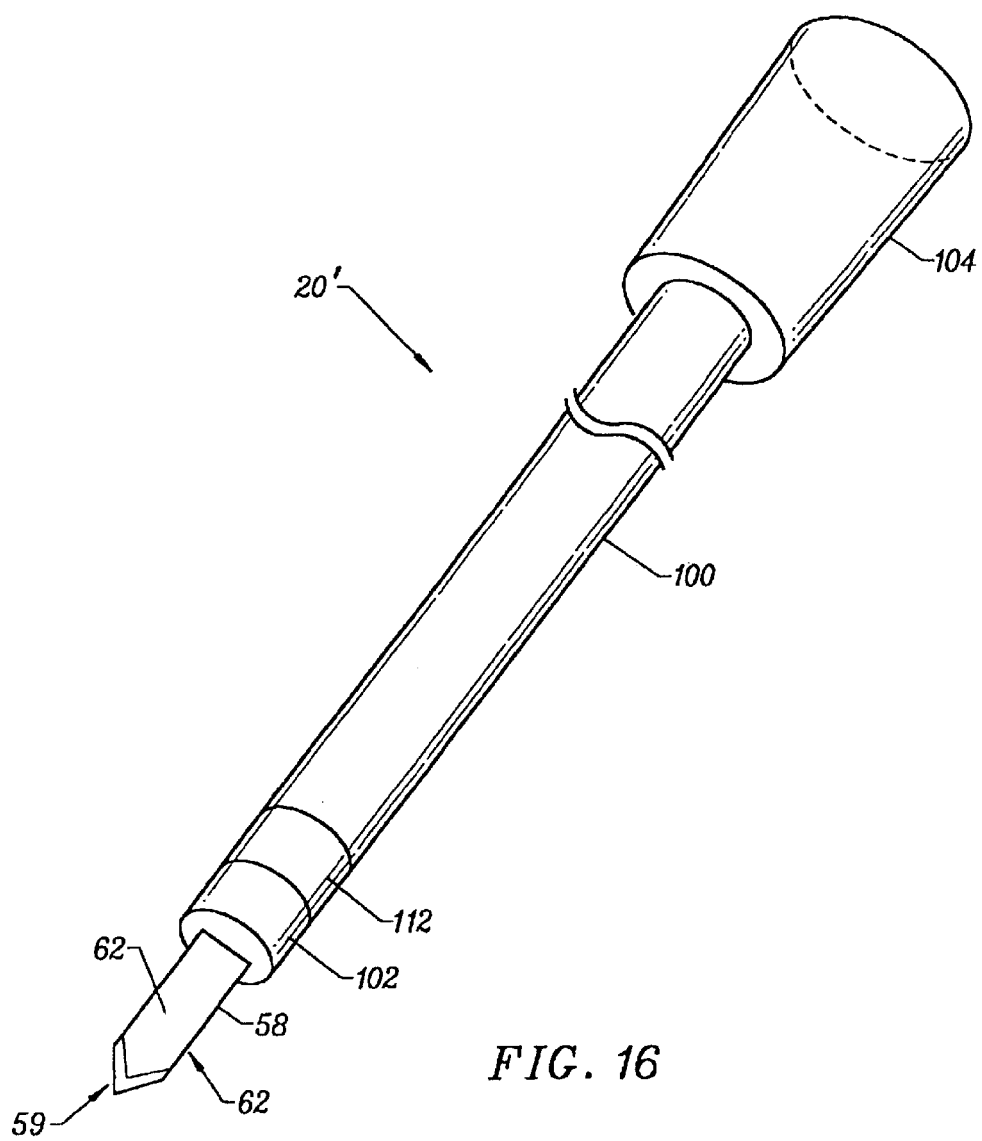
FIG. 16 is a perspective view of an electrosurgical probe having an elongated, blade-like active electrode.

FIG. 16 illustrates an electrosurgical probe 20' according to another embodiment of the present invention. Probe 20' generally includes handle 104 attached to shaft 100, and has a single, thin, elongated active blade electrode 58. Active electrode 58 is mechanically and electrically separated from return electrode 112 by a support structure 102. The active blade electrode 58 has a sharp distal edge 59 which helps facilitate the cutting process, and sides 62 which contact the tissue (e.g., bone) as the blade electrode 58 passes through the tissue or body structure. By contacting the sides of the blade electrode 58 directly with the tissue or body structure, the electrical power supplied to electrode 58 by power supply 28 can provide hemostasis to the body structure during the cutting process. Optionally, probe 20' can further include one or more coagulation electrode(s) (not shown) configured to seal a severed vessel, bone, or other tissue that is being incised. Such coagulation electrode(s) may be configured such that a single voltage can be applied to coagulate with the coagulation electrode(s) while ablating tissue with the active electrode(s). According to one aspect of the invention, probe 20' is particularly useful for creating an incision in a patient's chest. For example, in an open CABG procedure, a gross thoracotomy or median sternotomy is first performed in which the sternum is sectioned longitudinally so as to allow the chest to be opened for access to the thoracic cavity. Active electrodes 58 include distal edge 59 suitable for sectioning the sternum, and sides 62 suitable for arresting bone bleeding within the incised sternum. Sides 62 are configured to slidably engage the sternum as active electrode 58 is moved with respect to the sternum. Return electrode 112 is spaced proximally from active electrode 58 such that the electrical current is drawn away from the surrounding tissue. Alternatively, the return electrode 112 may be a dispersive pad located on the external surface of the patient's body. By minimizing bleeding of the sternum during an open-chest procedure, the patient's recovery time can be substantially shortened and patient suffering is alleviated.

Figure 17A:
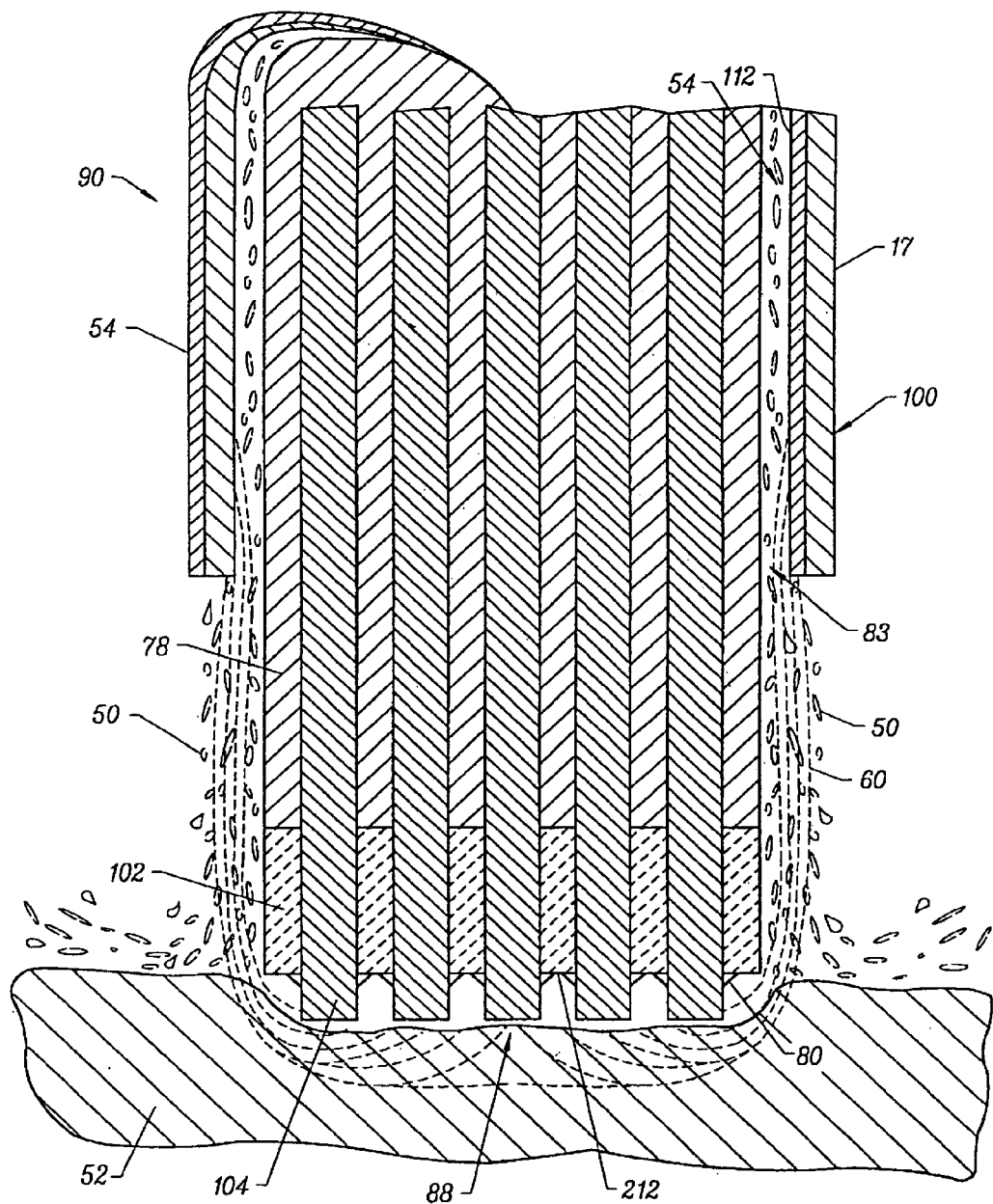
FIGS. 17A-17C are cross-sectional views of the distal portions of three different embodiments of an electrosurgical probe according to the present invention.
Figure 17B:
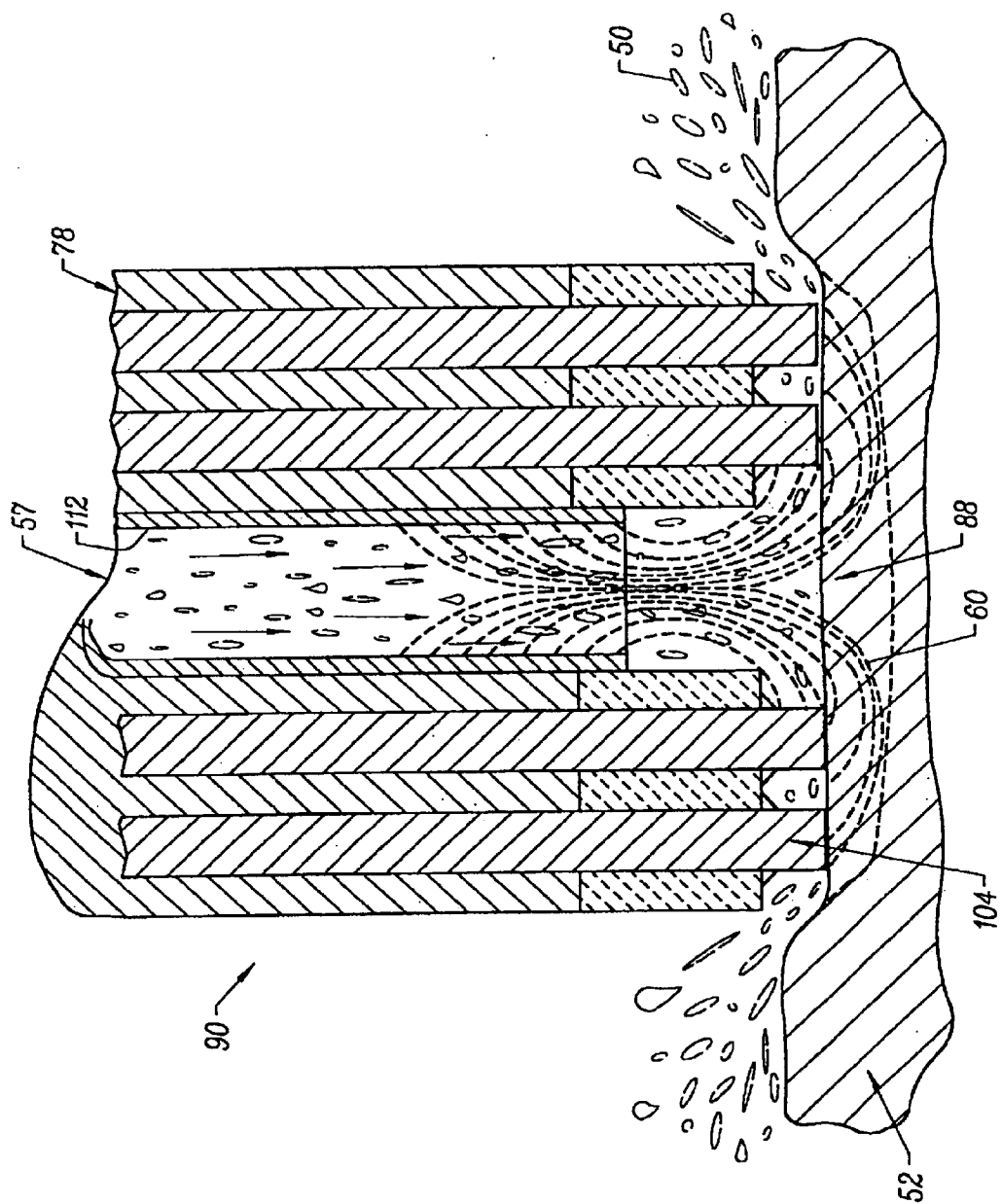
Figure 17C:
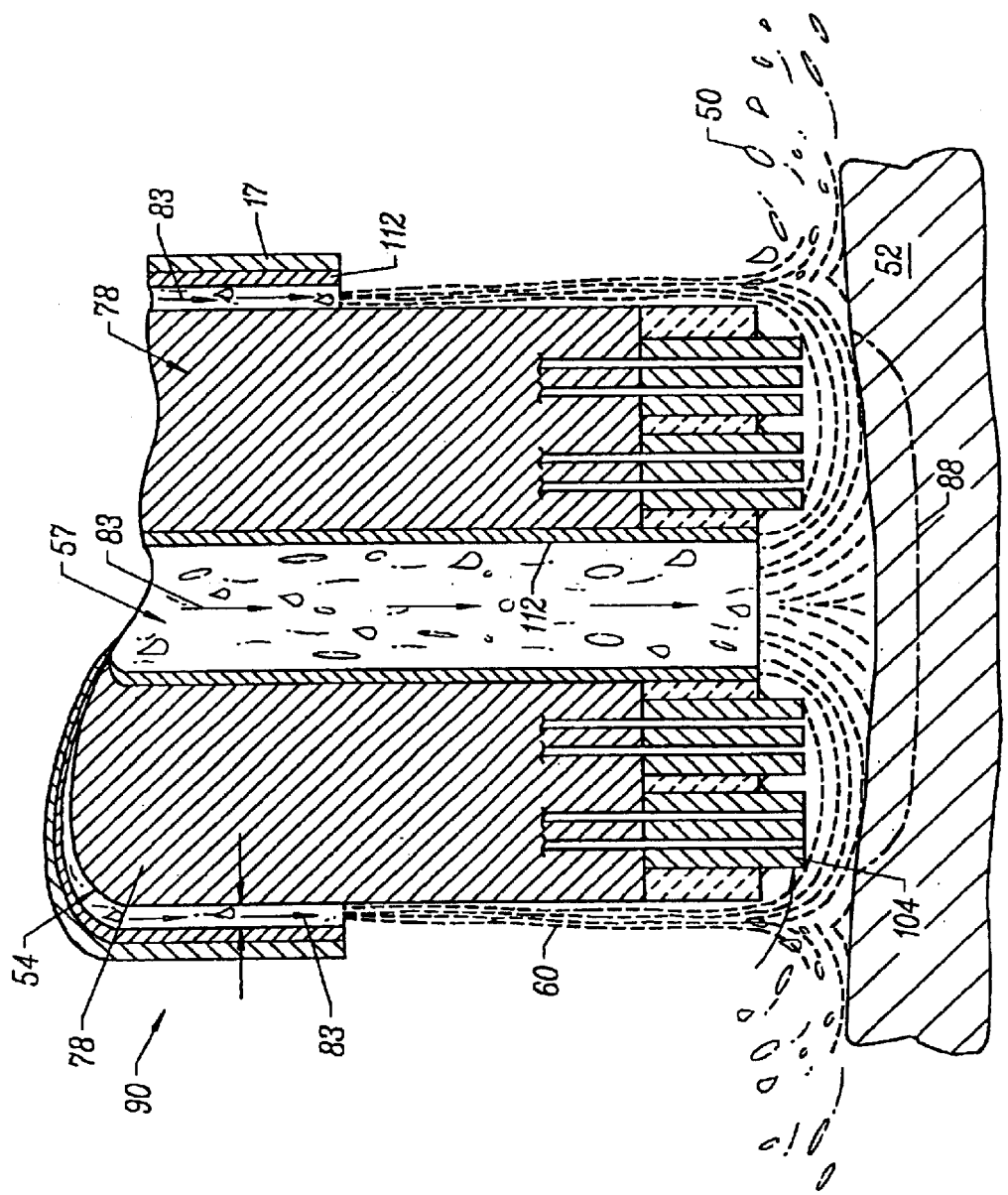

FIGS. 17A–17C schematically illustrate the distal portion of three different embodiments of a probe 90 according to the present invention. As shown in FIG. 17A, active electrodes 104 are anchored in a support 102 of suitable insulating material (e.g., ceramic or glass material, such as alumina, zirconia and the like) which could be formed at the time of manufacture in a flat, hemispherical or other shape according to the requirements of a particular procedure. In one embodiment, the support material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support 102 is adhesively joined to a tubular support member 78 that extends most or all of the distance between matrix 102 and the proximal end of probe 90. Tubular member 78 preferably comprises an electrically insulating material, such as an epoxy or silicone-based material.

According to one construction technique, active electrodes 104 extend through pre-formed openings in the support 102 so that they protrude above tissue treatment surface 212 by the desired distance. The electrodes are then bonded to the tissue treatment surface 212 of support 102, typically by an inorganic sealing material 80. Sealing material 80 is selected to provide effective electrical insulation, and good adhesion to both the support 102 and the platinum or titanium active electrodes. Sealing material 80 additionally should have a compatible thermal expansion coefficient, and a melting point well below that of platinum or titanium and alumina or zirconia, typically being a glass or glass ceramic.

In the embodiment shown in FIG. 17A, return electrode 112 comprises an annular member positioned around the exterior of shaft 100 of probe 90. Return electrode 112 may fully or partially circumscribe tubular member 78 to form an annular gap 54 therebetween for flow of electrically conductive liquid 50 therethrough, as discussed below. Gap 54 preferably has a width in the range of 0.25 mm to 4 mm. Alternatively, probe 90 may include a plurality of longitudinal ribs between tubular member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 17, which is typically formed as one or more electrically insulative sheaths or coatings, such as polytetrafluoroethylene, polyimide, and the like. The provision of the electrically insulative jacket 17 over return electrode 112 prevents direct electrical contact between return electrode 112 and any adjacent body structure. Such direct electrical contact between a body structure (e.g., the heart) and an exposed electrode member 112 could result in unwanted heating and necrosis of the structure at the point of contact.

As shown in FIG. 17A, return electrode 112 is not directly connected to active electrodes 104. To complete a current path so that active electrodes 104 are electrically connected to return electrode 112, electrically conductive liquid 50 (e.g., isotonic saline) is caused to flow along fluid path(s) 83. Fluid path 83 is formed by annular gap 54 between outer return electrode 112 and tubular support member 78. The electrically conductive liquid 50 flowing through fluid path 83 provides a pathway for electrical current flow between active electrodes 104 and return electrode 112, as illustrated by the current flux lines 60 in FIG. 17A. When a voltage difference is applied between active electrodes 104 and return electrode 112, high electric field intensities will be generated at the distal tips of active electrodes 104 with current flow from electrodes 104 through the target tissue to the return electrode, the high electric field intensities causing ablation of tissue 52 in zone 88.

FIG. 17B illustrates another alternative embodiment of electrosurgical probe 90 which has a return electrode 112 positioned within tubular member 78. Return electrode 112 may comprise a tubular member defining an inner lumen 57 for allowing electrically conductive liquid 50 (e.g., isotonic saline) to flow therethrough in electrical contact with return electrode 112. In this embodiment, a voltage difference is applied between active electrodes 104 and return electrode 112 resulting in electrical current flow through the electrically conductive liquid 50 as shown by current flux lines 60. As a result of the applied voltage difference and concomitant high electric field intensities at the tips of active electrodes 104, tissue 52 becomes ablated or transected in zone 88.

FIG. 17C illustrates another embodiment of probe 90 that is a combination of the embodiments in FIGS. 17A and 17B. As shown, this probe includes both an inner lumen 57 and an outer gap or plurality of outer lumens 54 for flow of electrically conductive fluid. In this embodiment, the return electrode 112 may be positioned within tubular member 78 as in FIG. 17B, outside of tubular member 78 as in FIG. 17A, or in both locations.

Figure 18:
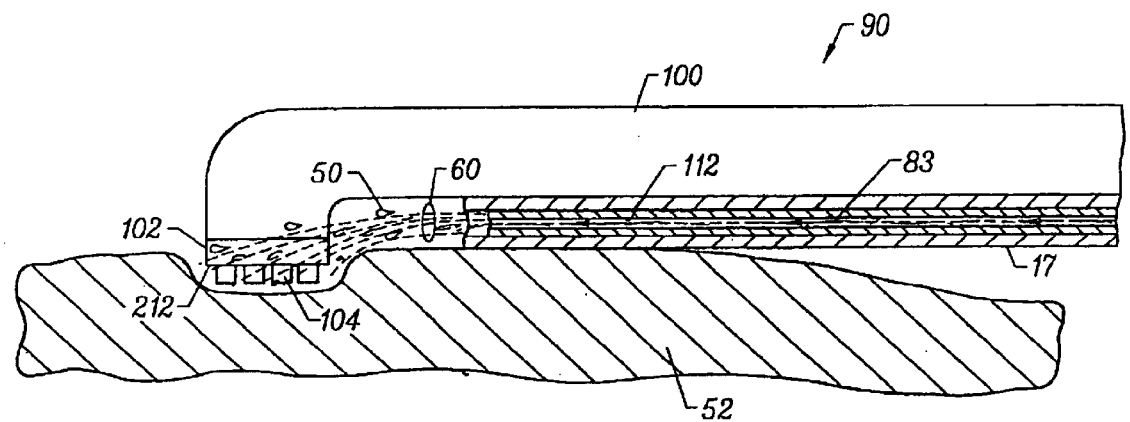
FIG. 18 illustrates an electrosurgical probe with a 90° distal bend and a lateral fluid lumen.

FIG. 18 illustrates another embodiment of probe 90 where the distal portion of shaft 100 is bent so that active electrodes extend transversely to the shaft. Preferably, the distal portion of shaft 100 is perpendicular to the rest of the shaft so that tissue treatment surface 212 is generally parallel to the shaft axis. In this embodiment, return electrode 112 is mounted to the outer surface of shaft 100 and is covered with an electrically insulating jacket 17. The electrically conductive fluid 50 flows along flow path 83 through return electrode 112 and exits the distal end of electrode 112 at a point proximal of tissue treatment surface 212. The fluid is directed exterior of shaft to surface 212 to create a return current path from active electrodes 104, through the fluid 50, to return electrode 112, as shown by current flux lines 60.

Figure 19:
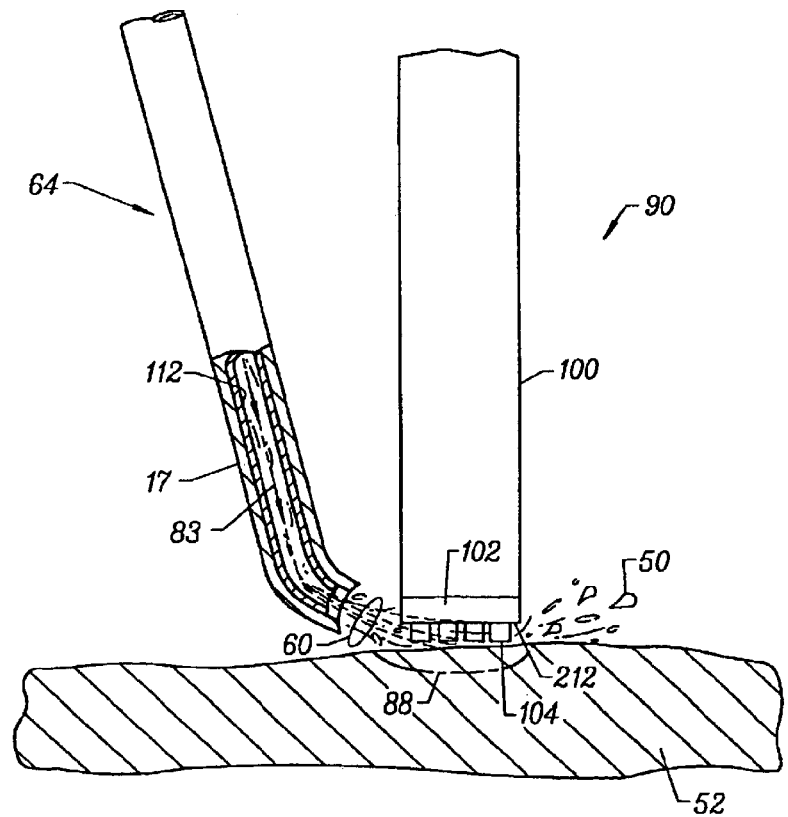
FIG. 19 iliustrates an electrosurgical system with a separate fluid delivery instrument according to the present invention.

FIG. 19 illustrates another embodiment of the invention where electrosurgical system 11 further includes a liquid supply instrument 64 for supplying electrically conductive fluid 50 between active electrodes 104 and a return electrode 112'. Liquid supply instrument 64 comprises an inner tubular member or return electrode 112' surrounded by an electrically insulating jacket 17. Return electrode 112' defines an inner passage 83 for flow of fluid 50. As shown in FIG. 19, the distal portion of instrument 64 is preferably bent so that liquid 50 is discharged at an angle with respect to instrument 64. This allows the surgical team to position liquid supply instrument 64 adjacent tissue treatment surface 212 with the proximal portion of supply instrument 64 oriented at a similar angle to probe 90.

Figure 20A:
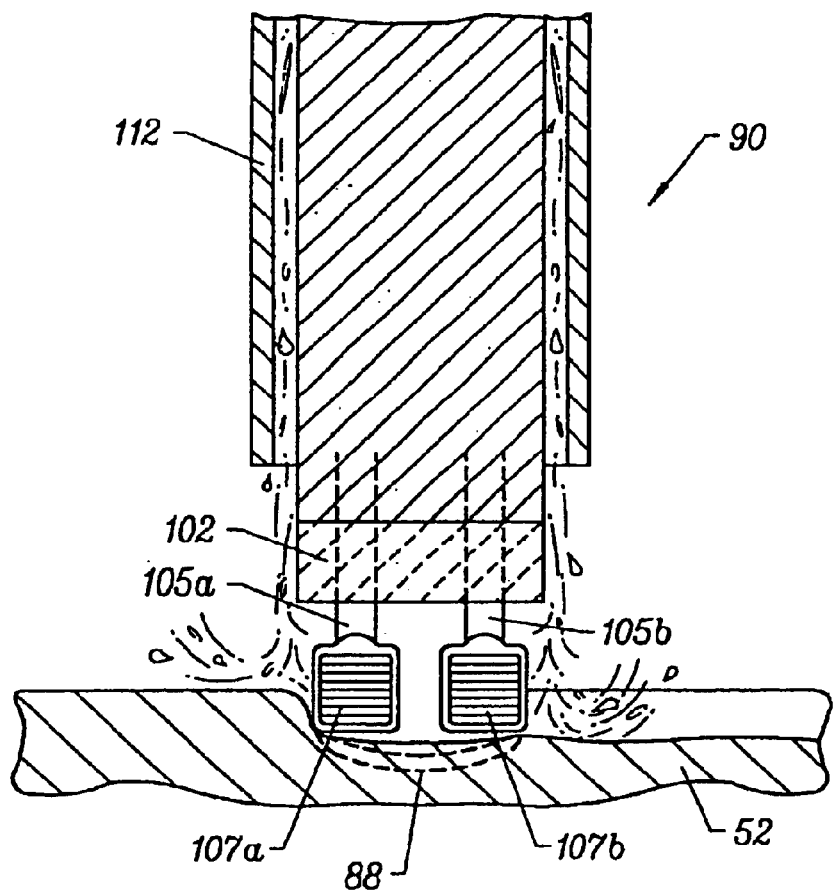
FIGS. 20A and 20B are cross-sectional and end views, respectively, of yet another electrosurgical probe incorporating flattened active electrodes.
Figure 20B:
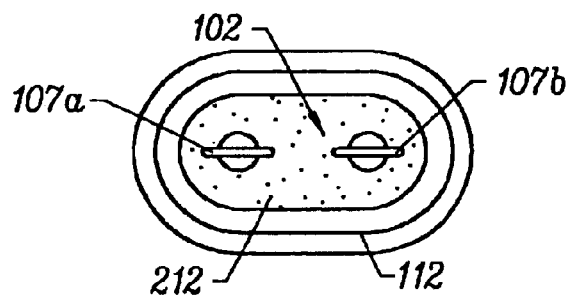

The present invention is not limited to an electrode array disposed on a relatively planar surface at the distal tip of probe 90, as described above. Referring to FIGS. 20A and 20B, an alternative probe 90 includes a pair of electrodes 105a, 105b mounted to the distal end of shaft 100. Electrodes 105a, 105b are electrically connected to a power supply, as described above, and preferably have tips 107a, 107b having a screwdriver shape. The screwdriver shape provides a greater amount of "edges" to electrodes 105a, 105b, to increase the electric field intensity and current density at tips 107a, 107b, thereby improving the cutting ability as well as the ability to provide hemostasis of the incised tissue.

FIG. 21 illustrates yet another embodiment designed for cutting of body tissue, organs, or structures. In this embodiment, the active electrodes 104 are arranged in a linear or columnar array of one of more closely spaced columns so that as the electrodes 104 are moved along the longer axis (denoted by arrow 160 in FIG. 21), the current flux lines are narrowly confined at the tip of the active electrodes 104 and result in a cutting effect in the body structure being treated. As before, the current flux lines 60 emanating from the active electrodes 104 pass through the electrically conductive liquid to the return electrode structure 112 located proximal to the probe tip.

Referring now to FIGS. 22 and 23, alternative geometries are shown for the active electrodes 104. These alternative electrode geometries allow the electrical current densities emanating from the active electrodes 104 to be concentrated to achieve an increased ablation rate and/or a more concentrated ablation effect due to the fact that sharper edges (i.e., regions of smaller radii of curvature) result in higher current densities. FIG. 22 illustrates a flattened extension of a round wire active electrode 104 which results in higher current densities at the edges 180. Another example is shown in FIG. 23 in which the active electrode 104 is formed into a cone shaped point 182 resulting in higher current densities at the tip of the cone.

Figure 24:
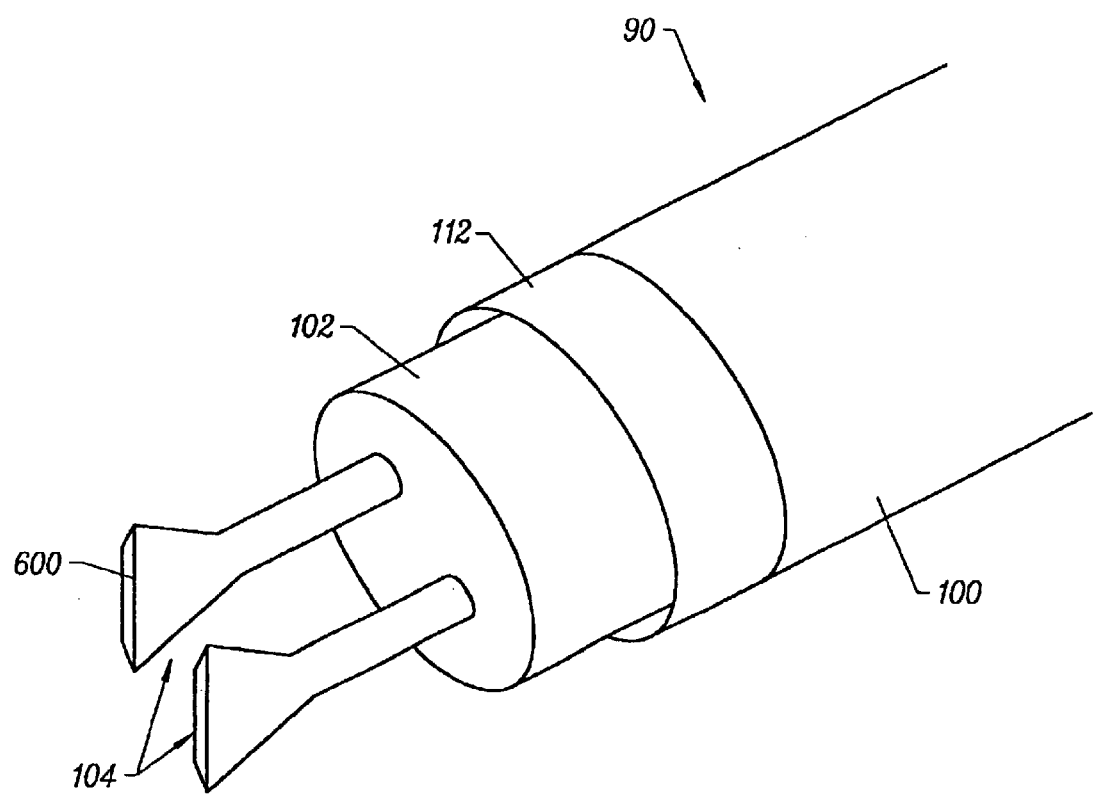
FIG. 24 is a perspective view of the distal portion of another electrosurgical probe according to the present invention.

Another embodiment of the electrosurgical probe is illustrated in FIG. 24. The electrosurgical probe 90 comprises a shaft 100 and at least two active electrodes 104 extending from a support 102 at the distal end of the shaft. The active electrodes 104 preferably define a distal edge 600 for making an incision in tissue. The edges 600 of the active electrodes 104 are substantially parallel with each other and usually spaced a distance of about 4 mm to 15 mm apart, preferably about 8 mm to 10 mm apart. The edges 600 extend from the distal end of support 102 by a distance of about 0.5 mm to 10 mm, preferably about 2 mm to 5 mm. In the exemplary embodiment, probe 90 will include a return electrode 112 spaced proximally from the active electrodes 104. In an alternative embodiment (not shown), one of the active electrodes 104 may function as a return electrode, or the return electrode may be a dispersive pad located on an external surface of the patient's body.

Figure 25:
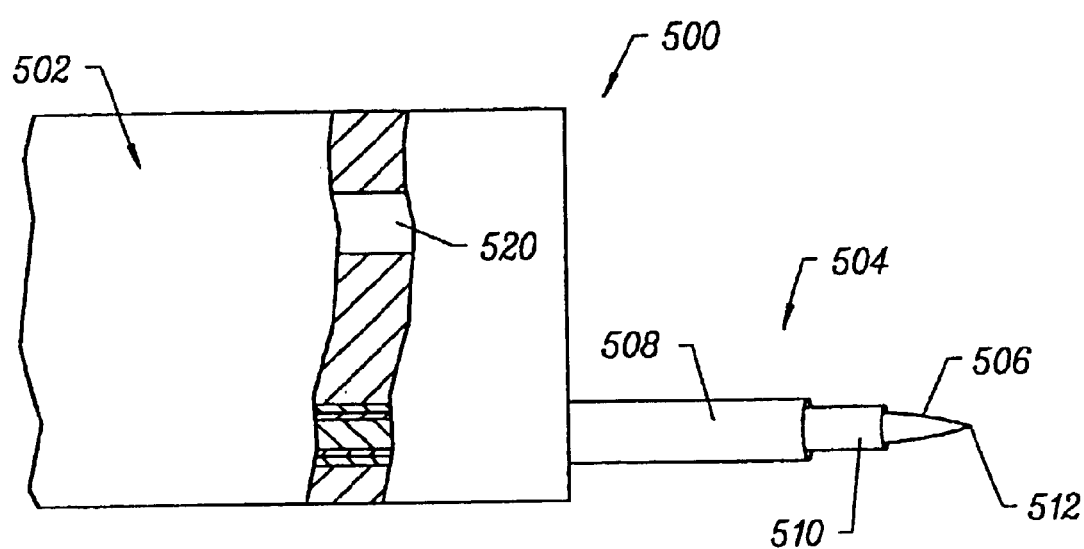
FIG. 25 illustrates another esnbodinient of the probe of the present invention, specifically designed for creating incisions in external skin surfaces.

FIG. 25 illustrates a distal portion of an electrosurgical probe 500 according to another embodiment of the present invention The embodiment of FIG. 25 is particularly useful for cutting or creating incisions in tissue structures. Probe 500 comprises a support member 502 coupled to a shaft or disposable tip (not shown) as described in previous embodiments. Support member 502 preferably comprises an inorganic electrically insulating material, such as ceramic, glass or glass-ceramic. In this embodiment, however, support member 502 may comprise an organic material, such as plastic, because the active electrode 506 and return electrode 508 are both spaced away from support member 502. Thus, the high intensity electric fields may be far enough away from support member 502 so as to allow an organic material.

An electrode assembly 504 extends from a distal end of support member 502, preferably by a distance of about 2 mm to 20 mm. Electrode assembly 504 comprises a single, active electrode 506 and a return electrode sleeve 508 spaced proximally from active electrode 506 by an insulation member 510, which preferably comprises an inorganic material, such as ceramic, glass or glass-ceramic. As shown, active electrode 506 preferably tapers to a sharp distal end 512 to facilitate the cutting or incising of tissue. In the exemplary embodiment, active electrode 506 has a proximal diameter of about 0.2 to 20 mm and a distal diameter of less than about 0.2 mm. Return electrode 508 is spaced from active electrode 506 a sufficient distance to prevent shorting or arcing therebetween at sufficient voltages to allow the volumetric removal of tissue. In the representative embodiment, the distal exposed portion of return electrode 508 is spaced about 0.5 to about 5 mm from the proximal exposed portion of active electrode 506. Of course, it will be recognized that the present invention is not limited to the particular dimensions and configuration of the electrode assembly 504 described herein, and a variety of different configurations may be envisioned depending on the surgical application.

As shown, probe 500 includes a fluid lumen 520 passing through support member 502 to a distal opening (not shown) at the distal end of support member 502. Fluid lumen 520 is coupled to a supply of electrically conductive fluid, such as isotonic saline, or other suitable conductive fluid for delivery of such fluid to the target site. In the exemplary embodiment, probe 500 is designed such that lumen 520 will be positioned above electrode assembly 504 during use such that the conductive fluid exiting the distal opening of lumen 520 will naturally pass over return electrode 508 and active electrode 506 thereby creating a current path therebetween. In addition, the conductive fluid will be sufficient to cover the active electrode 506 such that the conditions for plasma formation can be met, as described in detail above.

Figure 26:
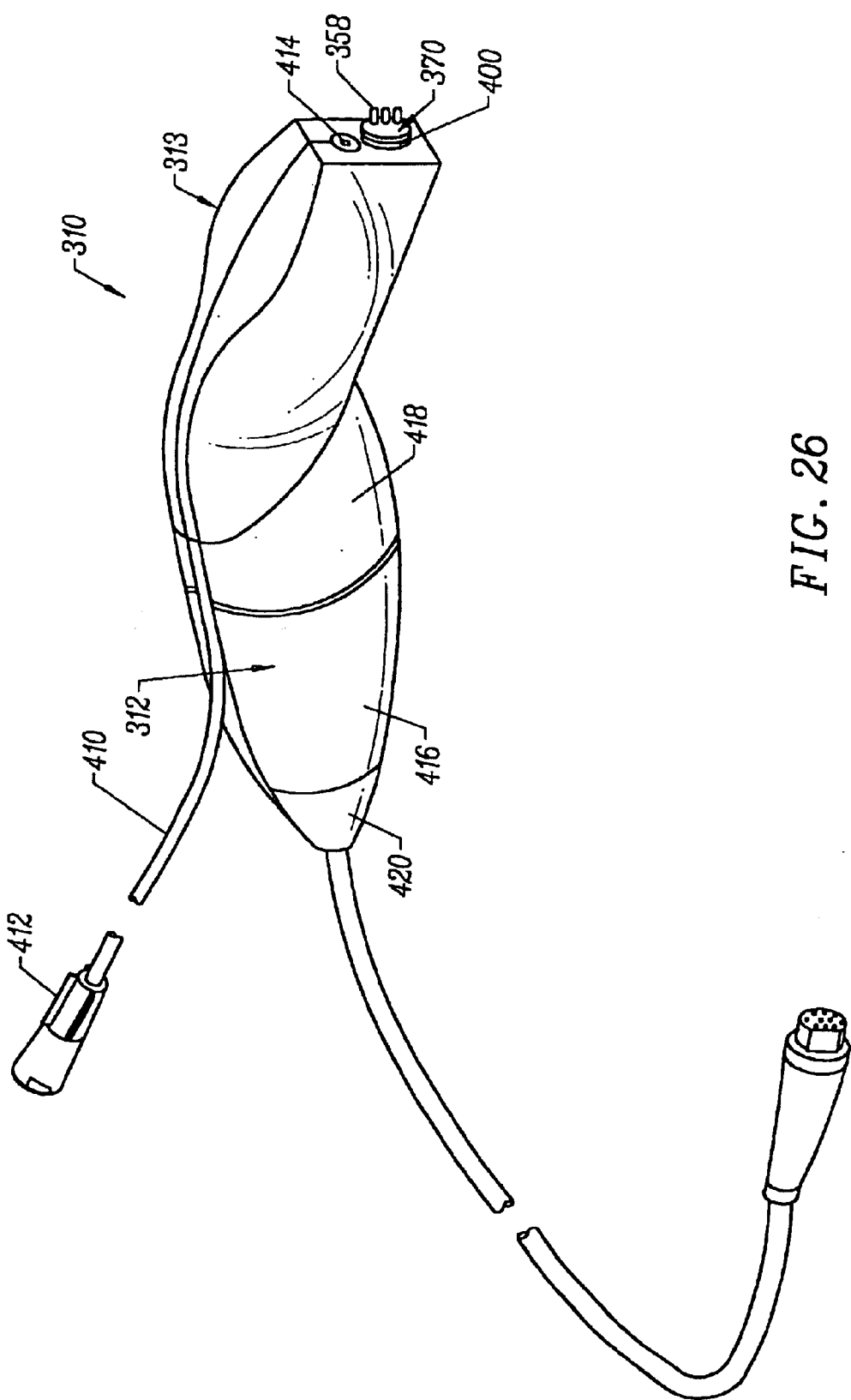
FIG. 26 is a perspective view of another embodiment of an electrosurgical probe for use in dermatology procedures.
Figure 27A:
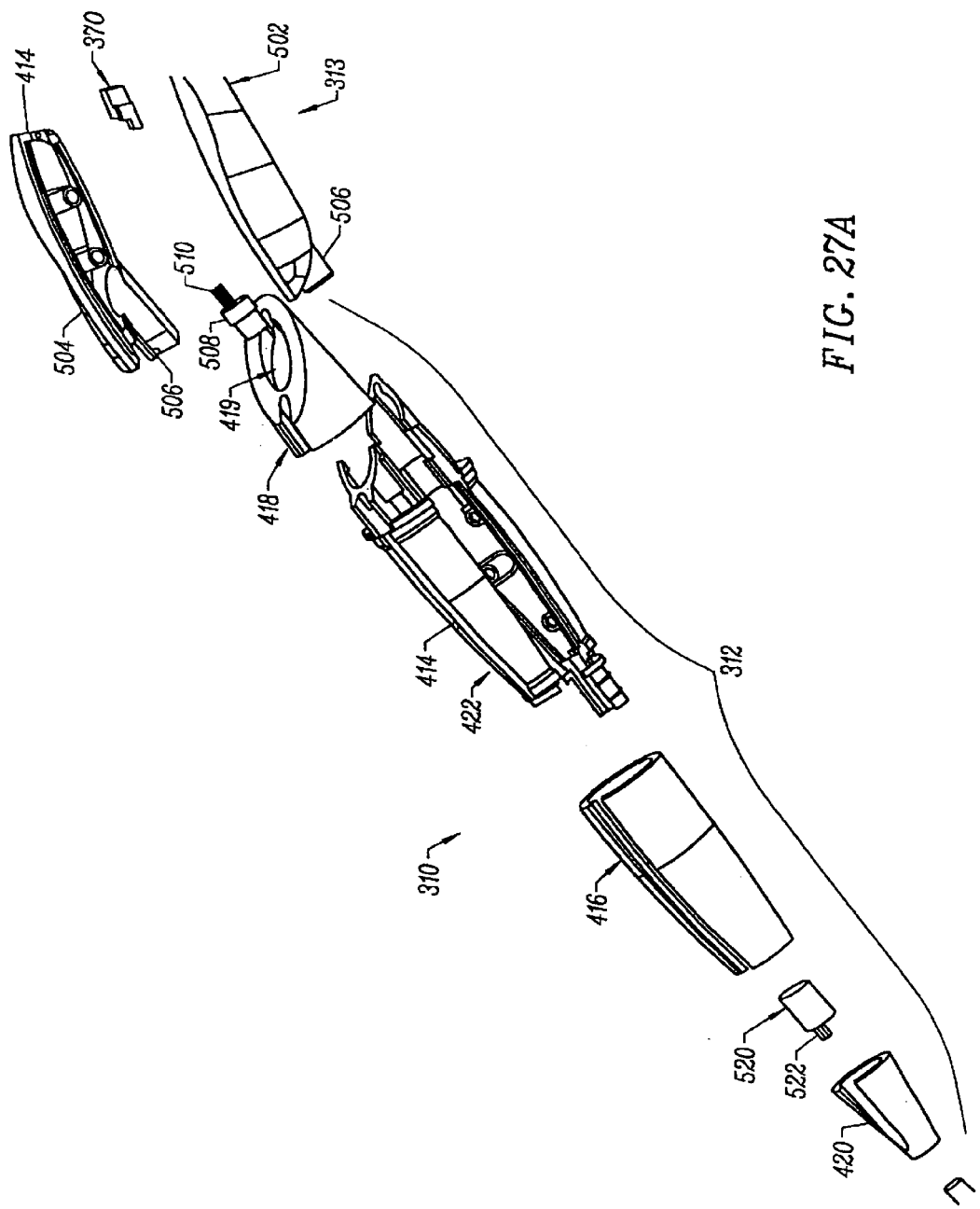
FIGS. 27A–27C are exploded, isomctric views of the probe of FIG. 26.
Figure 27B:
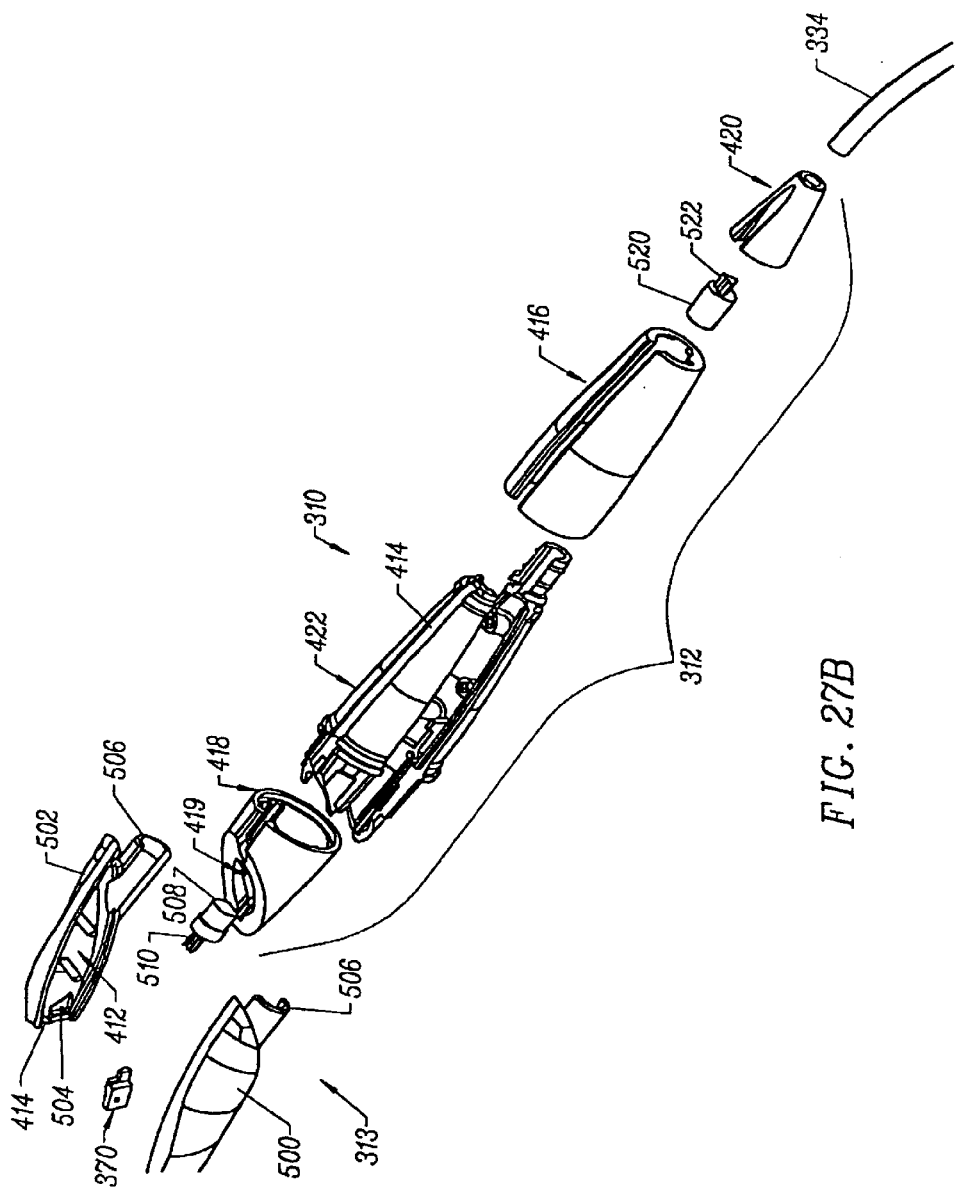

FIGS. 26, and 27A–C illustrate another exemplary electrosurgical probe 310 for cutting, incising, or removing tissue structures. Probe 310 comprises a shaft or disposable tip 313 removably coupled to a proximal handle 312, and an electrically insulating electrode support member 370 extending from tip 313 for supporting a plurality of active electrodes 358. Tip 313 and handle 312 typically comprise a plastic material that is easily molded into a suitable shape for handling by the surgeon. As shown in FIGS. 27A and 27B, handle 312 defines an inner cavity 372 that houses the electrical connections 374, and provides a suitable interface for connection to electrical connecting cable 34 (see FIG. 1). In the exemplary embodiment, handle 312 is constructed of a steam autoclavable plastic or metal (e.g., polyethylether ketone, or a stable metal alloy containing aluminum and/or zinc) so that it can be re-used by sterilizing handle 312 between surgical procedures. High service temperature materials are preferred, such as a silicone cable jacket and a poly-ether-imide handpiece or ULTEM® that can withstand repeated exposure to high temperatures.

Figure 27C:
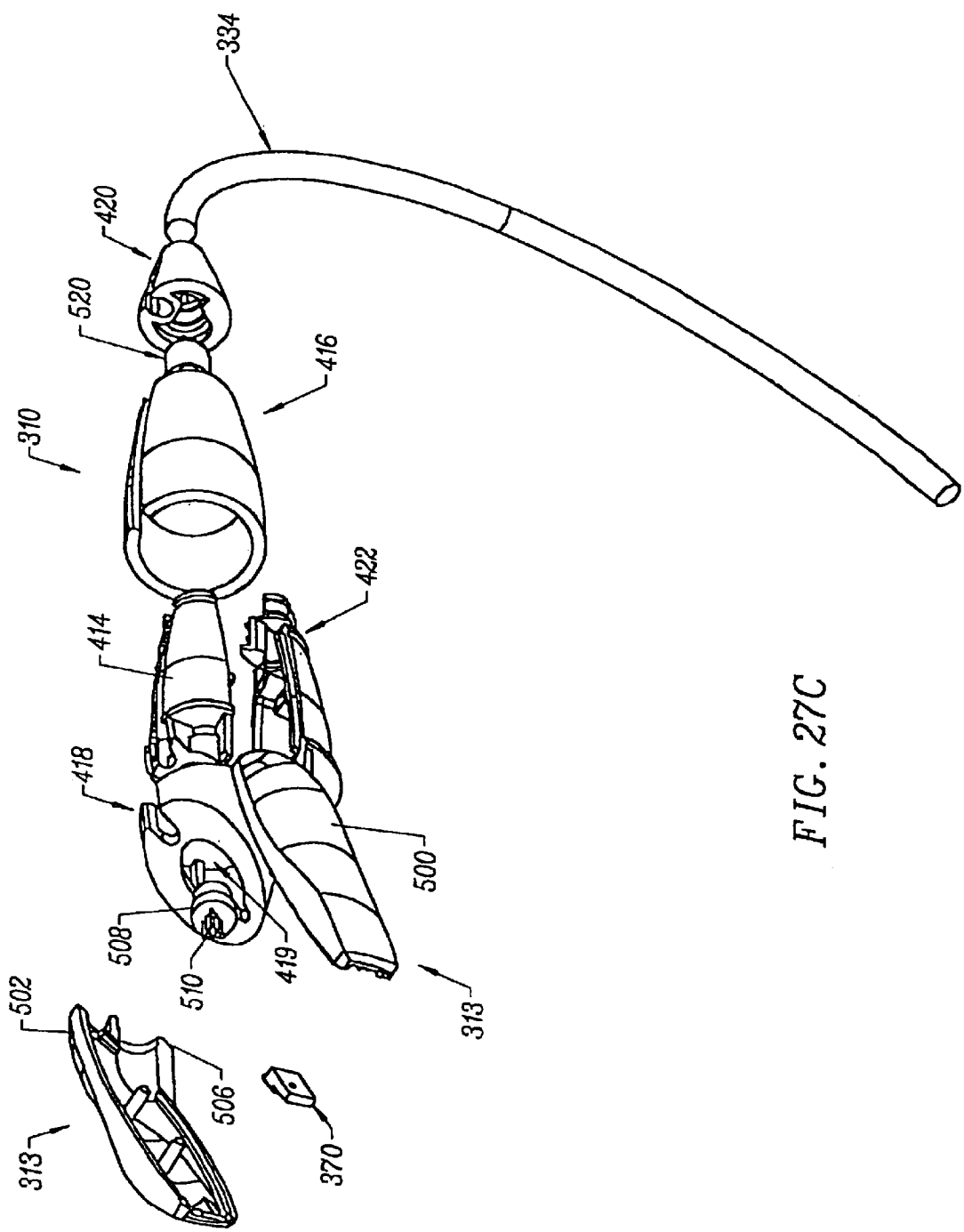

Referring to FIGS. 27A–27C, tip 313 preferably comprises first and second housing halves 500, 502 that snap fit together, and form a recess 404 therebetween for holding electrode support member 370 within the tip 313. Electrode support member 370 extends from the distal end of tip 313, usually by about 0.5 mm to 20 mm, and provides support for a plurality of electrically isolated active electrodes 358 and one or more return electrodes 400. Alternatively, electrode support member 370 may be recessed from the distal end of tip 313 to help confine the electrically conductive fluid around the active electrodes 358 during the surgical procedure, as discussed above. Electrode support member 370 has a substantially planar tissue treatment surface 380 that is usually disposed at an angle of about 10 to 90 degrees relative to the longitudinal axis of handle 312 to facilitate handling by the surgeon. In the exemplary embodiment, this function is accomplished by orienting tip 313 at an acute angle relative to the longitudinal axis of handle 312.

In the embodiment shown in FIGS. 26–27C, probe 310 includes a single annular return electrode 400 for completing the current path between active electrodes 358 and power supply 28 (see FIG. 1). As shown, return electrode 400 preferably has a fluid contact surface slightly proximal to tissue treatment surface 380, typically by about 0.1 mm to 2 mm, and preferably by about 0.2 mm to 1 mm. Return electrode 400 is coupled to a connector 404 that extends to the proximal end of handle 313, where it is suitably connected to power supply 28 (FIG. 1).

Referring again to FIGS. 27A–27C, tip 313 further includes a proximal hub 506 for supporting a male electrical connector 508 that holds a plurality of wires 510 each coupled to one of the active electrodes 358 or to return electrode 400 on support member 370. A female connector 520 housed within handle 312 is removably coupled to male connector 508, and a plurality of wires 522 extend from female connector 520 through a strain relief 524 to cable 334. Both sets of wires 510, 522 are insulated to prevent shorting in the event of fluid ingress into the probe 310. This design allows for removable connection of the electrodes in tip 313 with the connector 520 within handle 312 so that the handle can be re-used with different tips 313. Probe 310 will preferably also include an identification element, such as a coded resistor (not shown), for programming a particular voltage output range and mode of operation for the power supply. This allows the power supply to be employed with a variety of different probes for a variety of different applications.

In the representative embodiment, probe 310 includes a fluid tube 410 (FIG. 26) for delivering electrically conductive fluid to the target site. Fluid tube 410 is sized to extend through a groove 414 in handle 313 and through an inner cavity 412 in tip 312 to a distal opening 414 (FIG. 26) located adjacent electrode support member 370. Tube 410 extends all the way through inner cavity 412 to opening 414 to eliminate any possible fluid ingress into cavity 412. Fluid tube 410 includes a proximal connector for coupling to an electrically conductive fluid source 321.

Probe 310 will also include a valve or equivalent structure for controlling the flow rate of the electrically conductive fluid to the target site. In the representative embodiment shown in FIGS. 27A–27C, handle 312 comprises a main body 422 coupled between distal hub 418 and strain relief 420, and a rotatable sleeve 416 around main body 422. Distal hub 418 has an opening 419 for receiving proximal hub 506 of tip 313 for removably coupling the tip 313 to the handle 312. Sleeve 416 is rotatably coupled to strain relief 420 and distal hub 418 to provide a valve structure for fluid tube 410. As shown in FIG. 27A, fluid tube 410 extends through groove 414 from strain relief 420, through main body 422 and distal hub 420 to tip 313. Rotation of sleeve 416 will impede, and eventually obstruct, the flow of fluid through tube 410. Of course, this fluid control may be provided by a variety of other input and valve devices, such as switches, buttons, etc.

In alternative embodiments, the fluid path may be directly formed in probe 310 by, for example, a central inner lumen or an annular gap (not shown) within the handle and the tip. This inner lumen may be formed near the perimeter of the probe 310 such that the electrically conductive fluid tends to flow radially inward towards the target site, or it may be formed towards the center of probe 310 so that the fluid flows radially outward. In addition, the electrically conductive fluid may be delivered from a fluid delivery element (not shown) that is separate from probe 310. In arthroscopic surgery, for example, the body cavity will be flooded with isotonic saline and the probe 310 will be introduced into this flooded cavity. Electrically conductive fluid will be continually resupplied to maintain the conduction path between return electrode 400 and active electrodes 358 A more complete description of alternative electrosurgical probes incorporating one or more fluid lumen(s) can be found in commonly assigned, application Ser. No. 08/485,219, filed on Jun. 7, 1995, the complete disclosure of which is incorporated herein by reference.

Referring now to FIG. 26, electrically isolated active electrodes 358 are spaced apart over tissue treatment surface 380 of electrode support member 370, preferably in a linear array. In the representative embodiment, three active electrodes 358, each having a substantially conical shape, are arranged in a linear array extending distally from surface 380. Active electrodes 358 will usually extend a distance of about 0.5 mm to 20 mm from tissue treatment surface 380, preferably about 1 mm to 5 mm. Applicant has found that this configuration increases the electric field intensities and associated current densities at the distal edges of active electrodes 358, which increases the rate of tissue cutting. In the representative embodiment, the tissue treatment surface 380 has a circular cross-sectional shape with a diameter in the range of about 0.5 mm to 20 mm (preferably about 2 mm to 10 mm). The individual active electrodes 358 preferably taper outward as shown, or they may form a distal edge, such as the electrodes shown in FIGS. 3 and 24.

Figure 28:
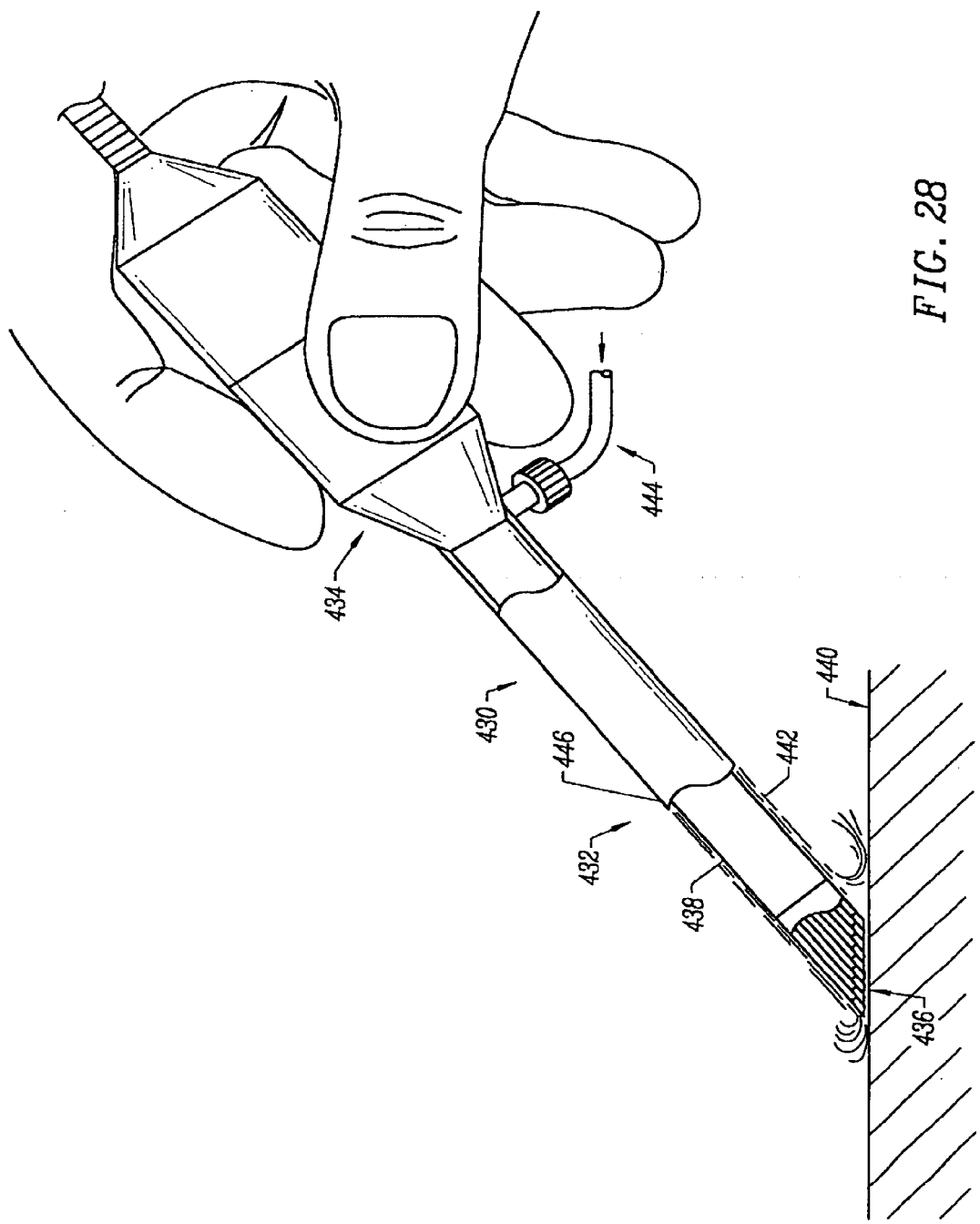
FIG. 28 is a cross-sectional view of another alternative electrosurgical probe.

Probe 430 of FIG. 28 includes a shaft 432 coupled to a proximal handle 434 for holding and controlling shaft 432. Probe 430 includes an active electrode array 436 at the distal tip of shaft 432, an annular return electrode 438 extending through shaft 432 and proximally recessed from the active electrode array 436, and an annular lumen 442 between return electrode 438 and an outer insulating sheath 446. Probe 430 further includes a liquid supply conduit 444 attached to handle 434 and in fluid communication with lumen 442, and a source of electrically conductive fluid (not shown) for delivering the fluid past return electrode 438 to the target site on the tissue 440. Electrode array 436 is preferably flush with the distal end of shaft 432 or distally extended from the distal end by a small distance (on the order of 0.005 inches) so as to minimize the depth of ablation. Preferably, the distal end of shaft 432 is beveled to improve access and control of probe 430 while treating the target tissue.

Figure 29:
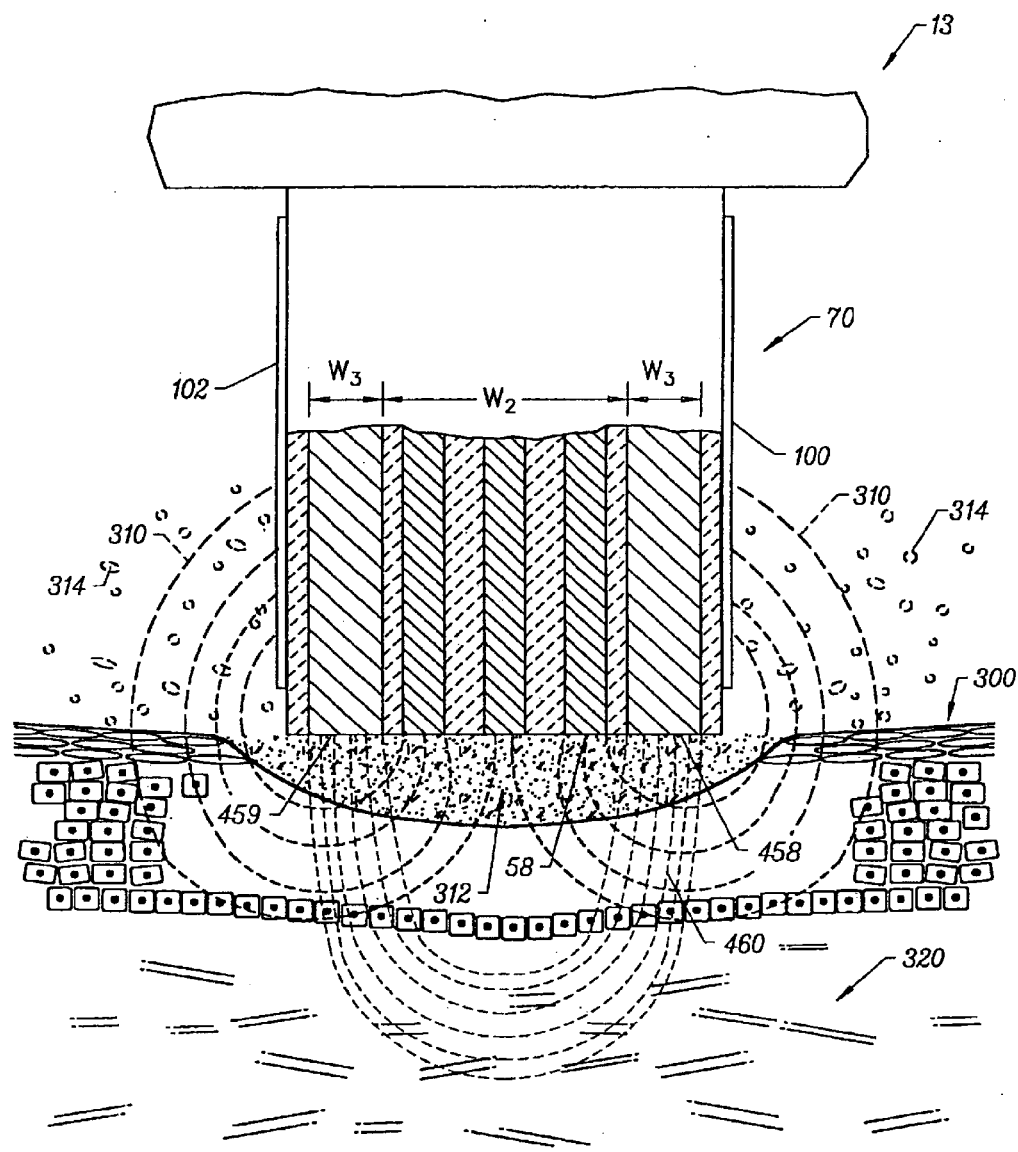
FIG. 29 illustrates another embodiment of the electrosurgical probe of the present invention, incorporating additional active electrodes.

Yet another embodiment of the present invention is shown in FIG. 29. Auxiliary active electrodes 458, 459 are positioned at the distal tip 70 of the probe. Auxiliary active electrodes 458, 459 may be the same size as ablation active electrodes 58, or larger as shown in FIG. 29. One operating arrangement is to connect auxiliary active electrodes 458, 459 to two poles of a high frequency power supply to form a bipolar circuit allowing current to flow between the terminals of auxiliary active electrodes 458, 459 as shown by current flux lines 460. Auxiliary active electrodes 458, 459 are electrically isolated from ablation electrodes 58. By proper selection of the inter-electrode spacing, $W_2$, and electrode width, $W_3$, and the frequency of the applied voltage, the current flux lines 460 can be caused to flow below the target layer as described above.

The voltage will preferably be sufficient to establish high electric field intensities between the active electrode array 436 and the target tissue 440 to thereby induce molecular breakdown or disintegration of several cell layers of the target tissue. As described above, a sufficient voltage will be applied to develop a thin layer of vapor within the electrically conductive fluid and to ionize the vaporized layer or region between the active electrode(s) and the target tissue. Energy in the form of charged particles are discharged from the vapor layer to ablate the target tissue, thereby minimizing necrosis of surrounding tissue and underlying cell layers.

Figure 30:
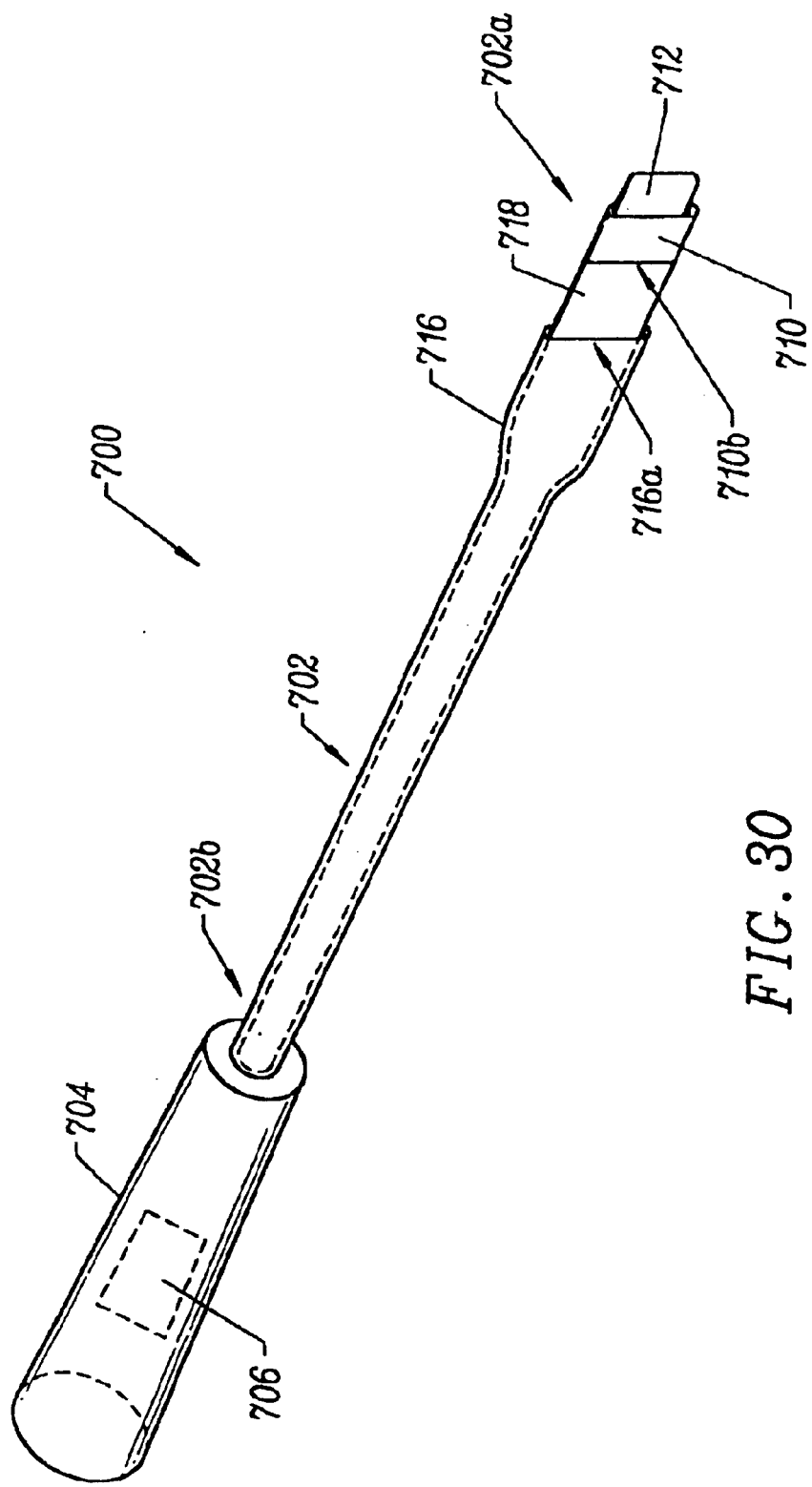
FIG. 30 is a perspective view of an electrosurgical probe having a blade electrode.

With reference to FIG. 30, there is shown in perspective view an electrosurgical probe 700, according to another embodiment of the invention. Probe 700 includes a shaft 702 having a shaft distal end portion 702a and a shaft proximal end portion 702b. Shaft 702 is affixed at its proximal end 702b to a handle 704. Shaft 702 typically comprises an electrically conductive material, usually a metal, such as tungsten, stainless steel, platinum or its alloys, titanium or its alloys, molybdenum or its alloys, nickel or its alloys. An electrically insulating electrode support 710 is disposed at shaft distal end 702a. An active electrode 712 is disposed on electrode support 710. Active electrode 712 comprises a blade electrode (e.g., FIGS. 31A, 31B). An electrically insulating sleeve 716 covers a portion of shaft 702, and terminates at sleeve distal end 716a to define an exposed portion of shaft 702 extending between electrode support proximal end 710b and sleeve distal end 716a. This exposed portion of shaft 702 defines a return electrode 718 on shaft distal end portion 702a. (In an alternative embodiment, the return electrode may take the form of an annular band of an electrically conductive material, e.g., a platinum alloy, disposed on the exterior of the shaft distal end.) A cavity within handle 704 accommodates a connection block 706 which is connected to active electrode 712 and return electrode 718 via electrode leads (not shown). Connection block 706 provides a convenient mechanism for coupling active electrode 712 and return electrode 718 to opposite poles of a power supply (e.g., power supply 28, FIG. 1).

Figure 31A:
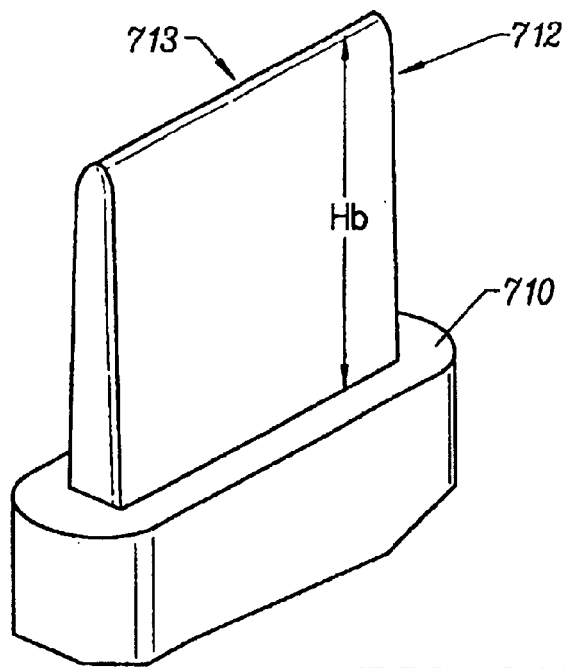
FIG. 31A is a perspective view.

FIG. 31A is a perspective view of an active electrode 712 of probe 700, according to one embodiment of the invention. Active electrode 712 is in the form of a single blade electrode which extends from electrode support 710 to a distance, $H_b$. The distance $H_b$ may vary, for example, according to the intended applications of probe 700, and the value of $H_b$ is at least to some extent a matter of design choice. Typically, for a broad array of electrosurgical procedures, the distance $H_b$ is in the range of from about 0.02 mm to about 5 mm. Active electrode 712 includes an active edge 713 which is adapted for generating high current densities thereat upon application of a high frequency voltage from the power supply between active electrode 712 and return electrode 718. In this way, active edge 713 can efficiently effect localized ablation of tissues via molecular dissociation of tissue components which contact, or are in close proximity to, active edge 713. A process for ablation of tissues via molecular dissociation of tissue components has been described hereinabove.

Figure 31B:
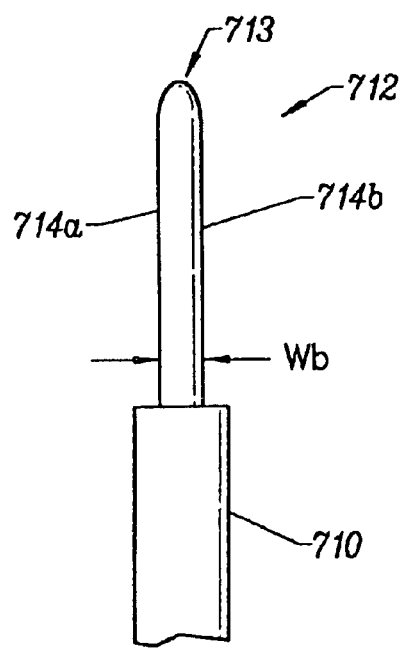
FIG. 31B is a lateral view, of a blade electrode, according to one embodiment of the invention.

As best seen in FIG. 31B, the blade-like active electrode 712 further includes first and second blade sides, 714a, 714b, respectively. First and second blade sides 714a, 714b are separated by a maximum distance, $W_b$. The distance $W_b$ is typically in the range of from about 0.1 mm to about 2.5 mm. In the embodiment of FIG. 31B, first and second blade sides 714a, 714b are substantially parallel to each other. Each of first and second blade sides 714a, 714b are adapted for engaging tissue severed, ablated, or otherwise modified by active edge 713, and for coagulating tissue engaged by first blade side 714a and/or second blade side 714b. In this way, active electrode 712 can precisely and effectively sever, ablate, or otherwise modify a target tissue with active edge 713 to form a first-modified tissue, and at the same time, or shortly thereafter, further modify the first-modified tissue by means of first and second blade sides 714a, 714b. For example, active edge 713 can make an incision in a target tissue via localized molecular dissociation of target tissue components, while first and second blade sides 714a, 714b can effect hemostasis in the severed tissue.

Figure 32A:
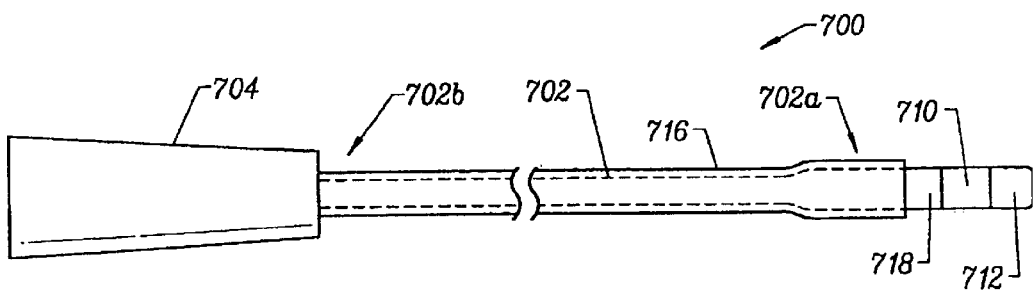
FIGS. 32A, 32B, and 32C are a side view, a plan view, and an end view, respectively, of an electrosurgical probe having a blade electrode.
Figure 32B:
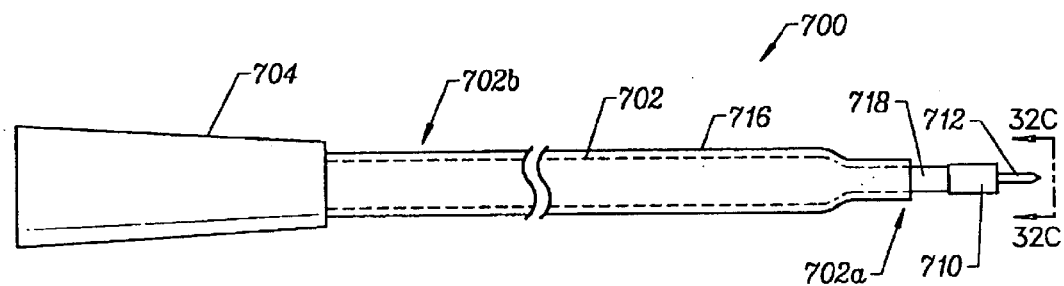
Figure 32C:
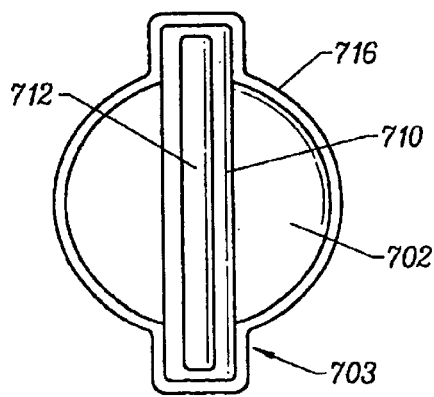

FIGS. 32A, 32B, and 32C are a side view, a plan view, and an end view, respectively, of electrosurgical probe 700 having a blade-like active electrode 712, according to one embodiment of the invention. In the embodiment of FIGS. 32A–C, electrode support 710 is disposed at the terminus of shaft 702, and active electrode 712 is affixed to support distal end 710a (e.g., FIG. 33A). However, other arrangements for electrode support 710 and active electrode 712 are within the scope of the invention (e.g., FIGS. 34A–C, 35A–C). Active electrode 712 is in the form of a substantially flat metal blade. Active electrode 712 is shown as being substantially rectangular as seen from the side (FIG. 32A). However, various other shapes for active electrode 712 are within the scope of the invention (e.g., FIGS. 33C–E). FIG. 32C is an end view of probe 700 as seen along the lines 32C–32C of FIG. 32B, showing a laterally compressed region 703 of shaft 702. Laterally compressed region 703 may be adapted for housing electrode support 710. Laterally compressed region 703 may also facilitate manipulation of shaft distal end portion 702a of probe 700 during various surgical procedures, particularly in situations where accessibility of a target tissue is restricted.

Figure 33A:
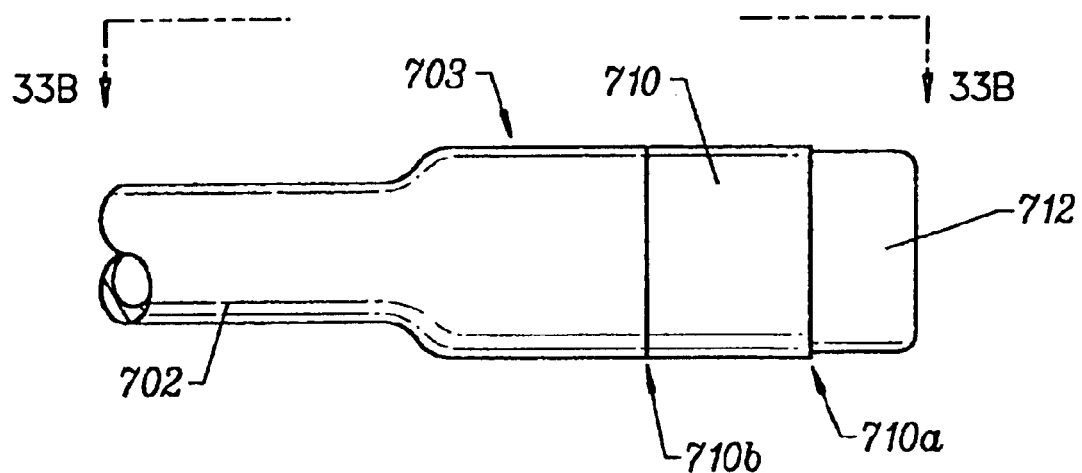
FIGS. 33A and 33B are a side view and a plan view, respectively, of the distal end of an electrosurgical probe having a terminal blade electrode, according to one embodiment of the invention.
Figure 33B:
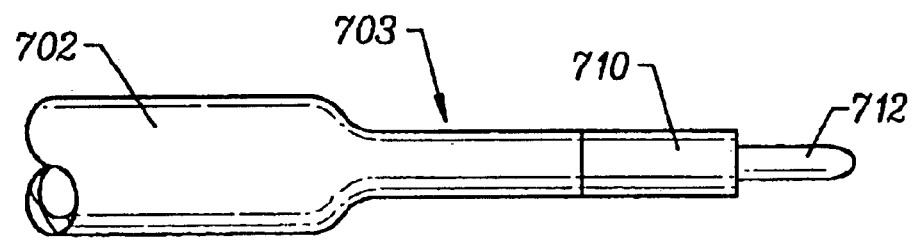

FIGS. 33A and 33B are a side view and a plan view, respectively, of the distal end of probe 700, showing details of shaft distal end portion 702a and terminally disposed blade active electrode 712, according to one embodiment of the invention. Blade electrode 712 is substantially rectangular in shape as seen from the side (FIG. 33A). The distal end of shaft 702 includes laterally compressed region 703. As seen from the side (FIG. 33A), laterally compressed region 703 appears wider than more proximal portions of shaft 702. FIG. 33B is a plan view of probe 700 as seen along the lines 33B–33B of FIG. 33A, in which laterally compressed region 703 appears narrower than more proximal portions of shaft 702. Electrode support 710 is mounted to the distal end of laterally compressed region 703. Typically, electrode support 710 comprises a durable, electrically insulating, refractory material having a certain amount of flexibility. For example, electrode support 710 may comprise a material such as a silicone rubber, a polyimide, a fluoropolymer, a ceramic, or a glass.

Figure 33C:
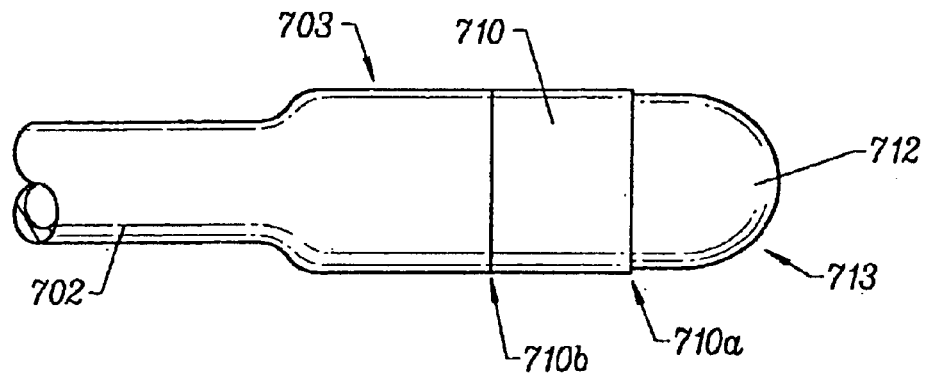
FIGS. 33C–33E each show a side view of the distal end of an electrosurgical probe having a terminal blade electrode, according to three different embodiments of the invention.
Figure 33D:
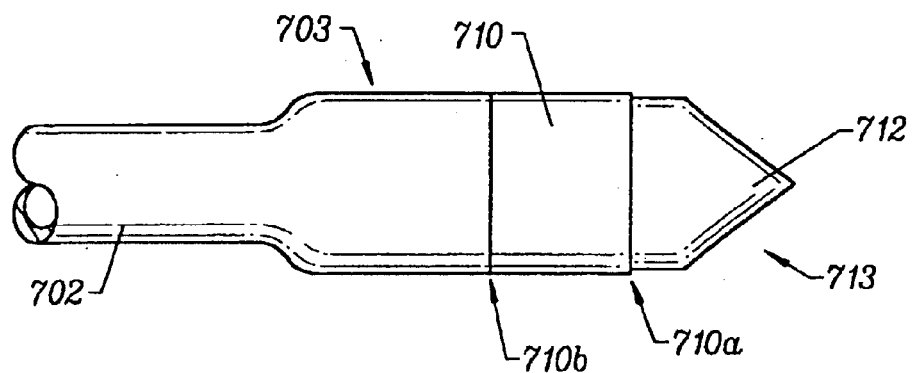
Figure 33E:
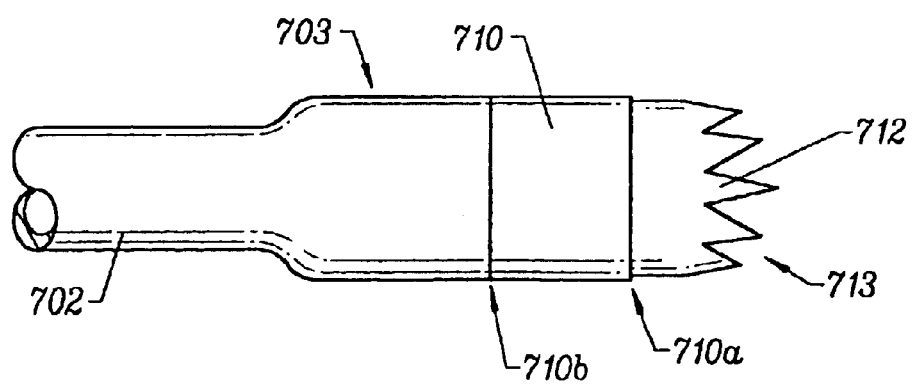

FIGS. 33C–33E each show a side view of the distal end of probe 700 having a terminal blade active electrode 712, according to three different embodiments of the invention. Electrode support 710 is mounted terminally on shaft 702, and includes a support distal end 710a and a support proximal end 710b. In the embodiment of FIG. 33C, active edge 713 of active electrode 712 is arcuate, convex, or substantially semi-circular in shape. In the embodiment of FIG. 33D, active electrode 712 has a pointed active edge 713, while in the embodiment of FIG. 33E, the active edge 713 of active electrode 712 is serrated.

Figure 34A:
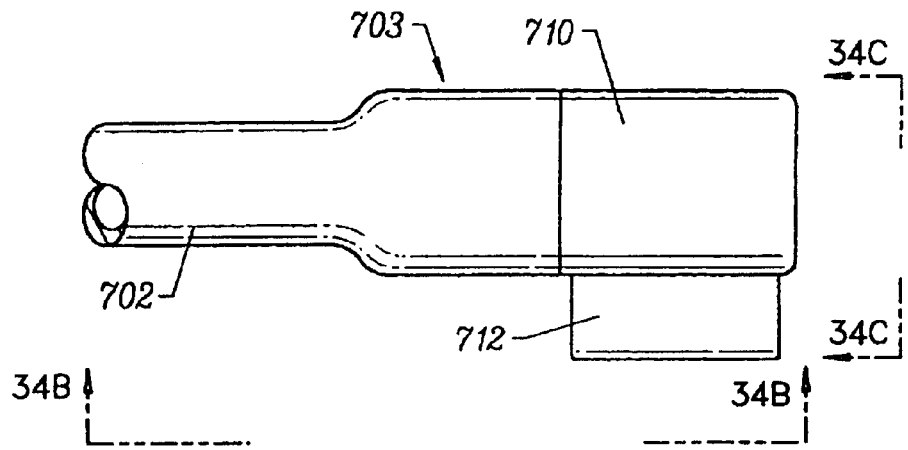
FIGS. 34A, 34B, and 34C are a side view, a plan view, and an end view, respectively, of an electrosurgical probe having a terminal electrode support and a lateral blade electrode, according to another embodiment of the invention.
Figure 34B:
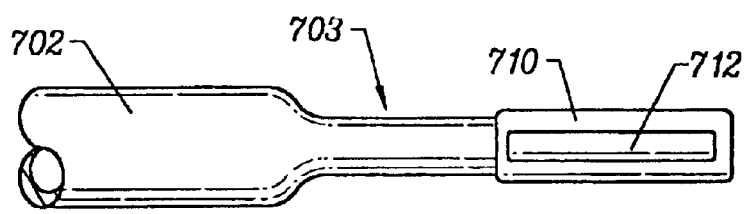
Figure 34C:
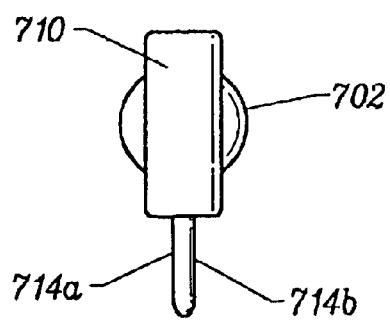

FIG. 34A shows in side view an electrosurgical probe 700 having electrode support 710 mounted terminally on shaft 702 and blade active electrode 712 disposed laterally on electrode support 710, according to another embodiment of the invention. FIG. 34B is a plan view of probe 700 taken along the lines 34B–34B of FIG. 34A. FIG. 34C is an end view taken along the lines 34C–34C of FIG. 34A. In the embodiments of FIGS. 34A–C, electrode 712 is in the form a substantially flat, metal blade having first and second blade sides 714a, 714b, substantially parallel to each other. First and second blade sides 714a, 714b are adapted for engaging and coagulating severed or modified tissue, as described hereinabove.

Figure 35A:
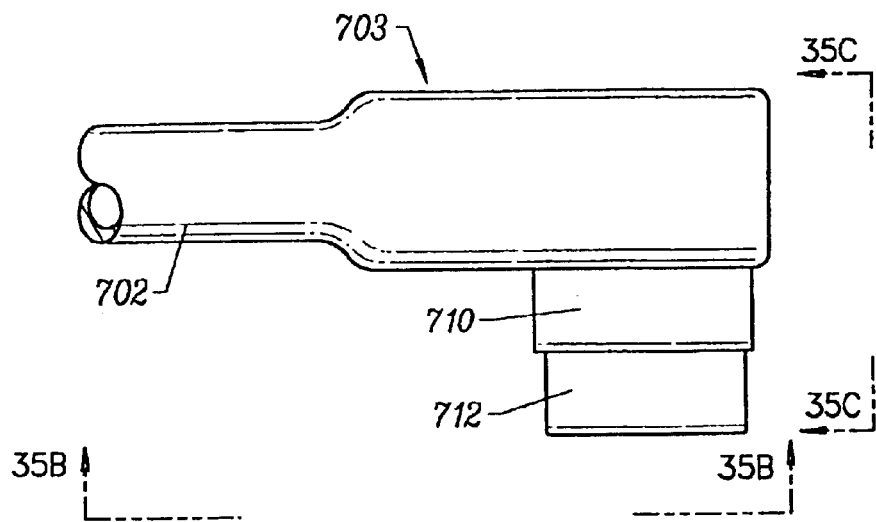
FIGS. 35A, 35B, and 35C are a side view, a plan view, and an end view, respectively, of an electrosurgical probe having a lateral electrode support and a lateral blade electrode, according to another embodiment of the invention.
Figure 35B:
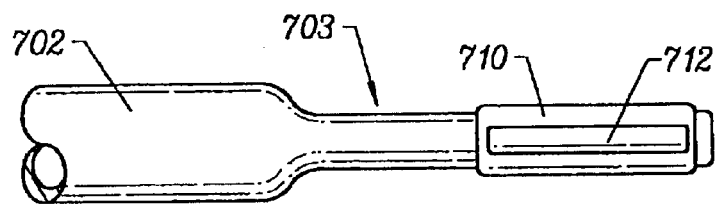
Figure 35C:
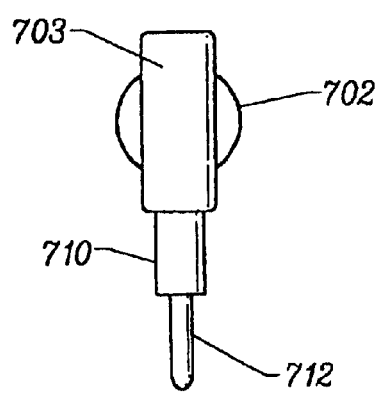

FIG. 35A shows in side view an electrosurgical probe 700 having electrode support 710 mounted laterally on the distal end of shaft 702, according to another embodiment of the invention. Blade active electrode 712 is mounted laterally on electrode support 710. FIG. 35B is a plan view of probe 700 taken along the lines 35B–35B of FIG. 35A. FIG. 35C is an end view taken along the lines 35C–35C of FIG. 35A. Active electrode 712 is in the form a substantially flat, metal blade having first and second blade sides 714a, 714b, substantially parallel to each other. Electrode support 710 is mounted laterally on laterally compressed region 703 of shaft 702.

Figure 36A:
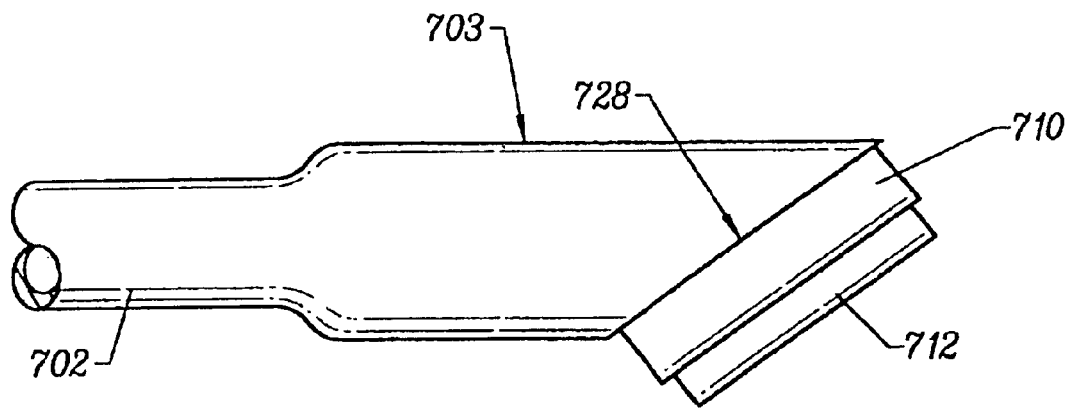
FIGS. 36A and 36B each show a side view of the distal end of an electrosurgical probe having a blade electrode, according to two different embodiments of the invention.
Figure 36B:
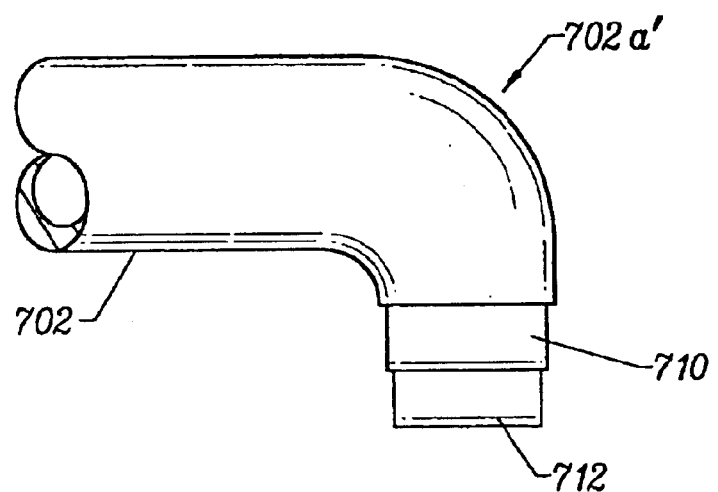

FIG. 36A shows a side view of the distal end of an electrosurgical probe 700, wherein shaft 702 includes a beveled end 728 to which electrode support 710 is mounted. Blade active electrode 712 is disposed on electrode support 710. The arrangement of electrode support 710 and electrode 712 on beveled end 728 may facilitate access of shaft distal end portion 702a in general, and of electrode 712 in particular, to a target tissue during various surgical procedures, particularly in situations where accessibility is restricted. FIG. 36B shows a side view of the distal end of an electrosurgical probe 700, according to another embodiment of the invention. Shaft 702 includes a curved distal end 702a'. Electrode support 710 is mounted on distal end 702a', and blade active electrode 712 is affixed to electrode support 710. Curved distal end 702a' facilitates access of electrode 712 to a target tissue during various surgical procedures.

Although in the embodiments of FIGS. 34A–C, FIGS. 35A–C, and FIGS. 36A–B, active electrode 712 is shown as being substantially rectangular, this representation should not be construed as limiting these embodiments to a rectangular active electrode 712. Indeed, each of the embodiments of FIGS. 34A–C, 35A–C, and 36A–B may have an active electrode 712 in a broad range of shapes, including those represented in FIGS. 33C–E.

Figure 37A:
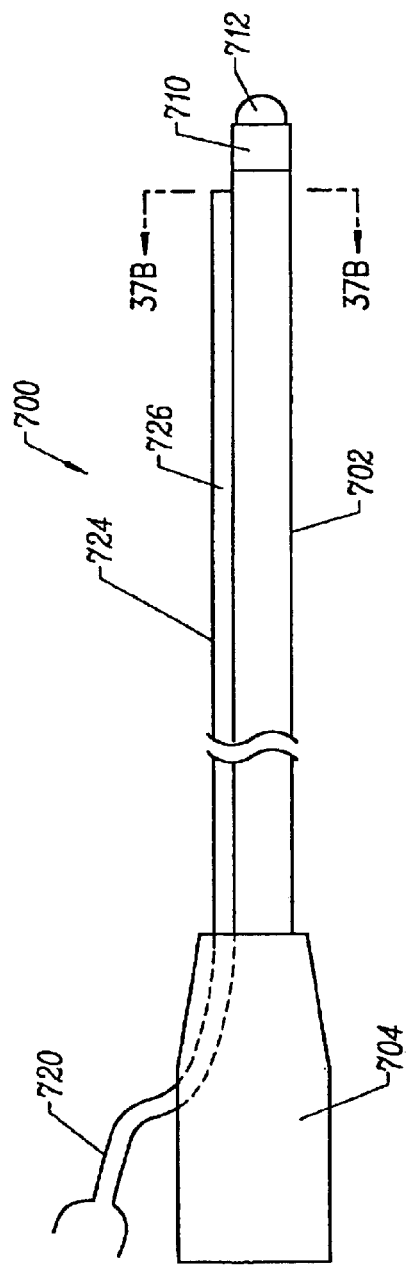
FIGS. 37A, and 37B are a side view and an end view, respectively, of an electrosurgical probe having a lumen external to the probe shaft, according to one embodiment of the invention.
Figure 37B:
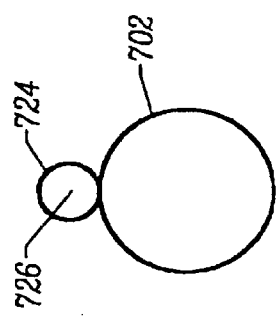

FIG. 37A shows in side view an electrosurgical probe 700 having an exterior tube 724 arranged on shaft 702 and coupled at its proximal end to a connection tube 720 at handle 704. Exterior tube 724 may comprise a plastic tube of suitable length commensurate with the size of probe 700. Exterior tube 724 defines a lumen 726, and typically terminates at shaft distal end 702a at a location somewhat proximal to electrode support 710. In some embodiments, probe 700 may include two or more exterior tubes 724, each exterior tube 724 having lumen 726. Each lumen 726 may serve as a conduit for an aspiration stream, or as a conduit for delivery of an electrically conductive fluid to the shaft distal end, generally as described hereinabove. FIG. 37B is an end view of probe 700 taken along the lines 37B–37B of FIG. 37A, showing exterior tube 724 and lumen 726 in relation to shaft 702. The diameter of exterior tube 724 is, at least to some extent, a matter of design choice. Exterior tube 724 may comprise a substantially rigid or somewhat flexible plastic tube comprising polyethylene, a polyimide, a fluoropolymer, and the like.

FIG. 38A shows, in side view, an electrosurgical probe 700 having an outer sheath 722 surrounding the exterior of a portion of shaft 702, according to another embodiment of the invention. Outer sheath 722 is coupled at its proximal end to a connection tube 720 at handle 704. Outer sheath 722 may comprise a plastic tube of suitable length and having a diameter larger than that of shaft 702. Together with the exterior of shaft 702, outer sheath 722 defines a lumen 726' in the form of an annular void. Typically, outer sheath 722 terminates at shaft distal end 702a at a location proximal to electrode support 710. Lumen 726' typically serves as a conduit for delivery of an electrically conductive fluid to the shaft distal end. FIG. 38B is an end view of probe 700 taken along the lines 38B–38B of FIG. 38A, showing outer sheath 722 and lumen 726' in relation to shaft 702. The diameter of outer sheath 722 is, at least to some extent, a matter of design choice. Outer sheath 722 may comprise a substantially rigid or somewhat flexible plastic tube comprising polyethylene, a polyimide, and the like.

Figure 39A:
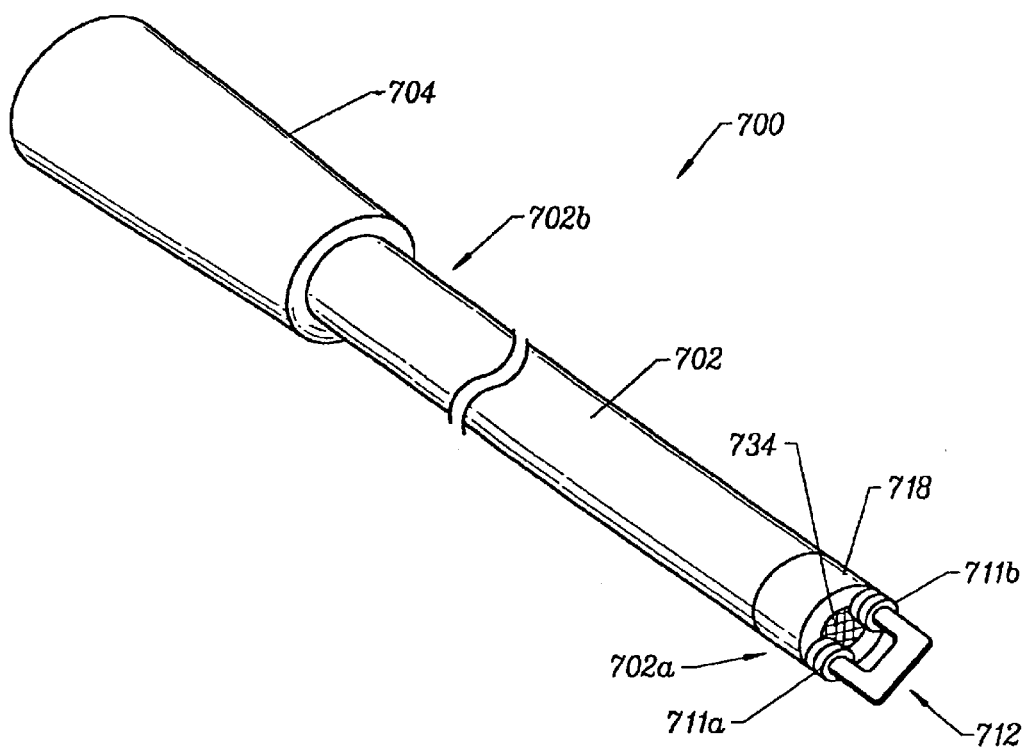
FIGS. 39A and 39B schematically represent a procedure for incising and coagulating tissue with an electrosurgical probe having a blade electrode, according to one embodiment of the invention.
Figure 39B:
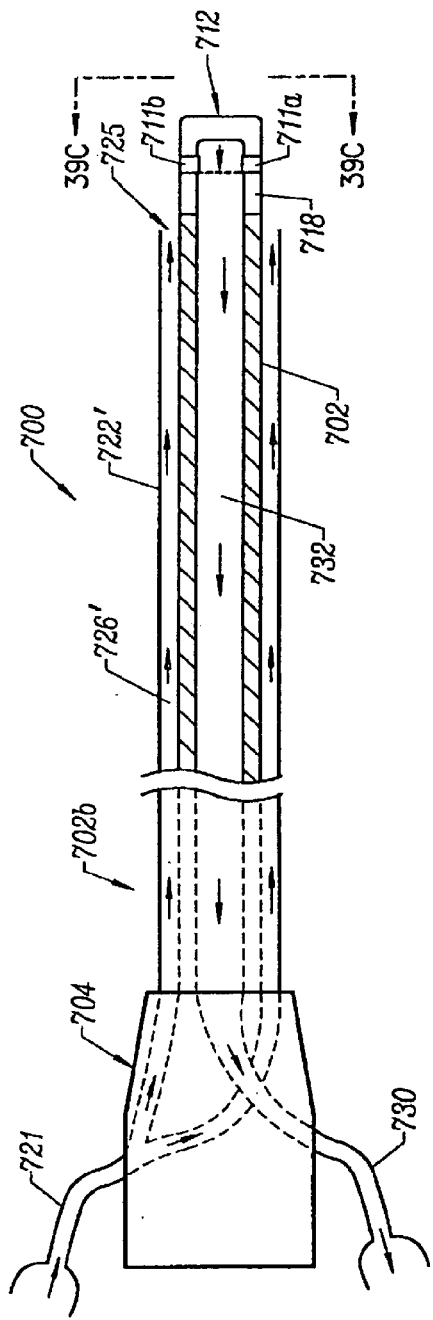
Figure 39D:
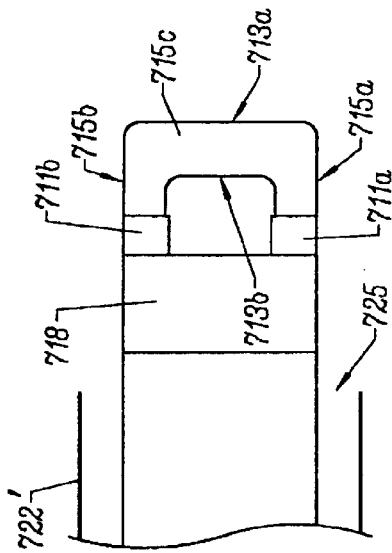
Figure 39C:
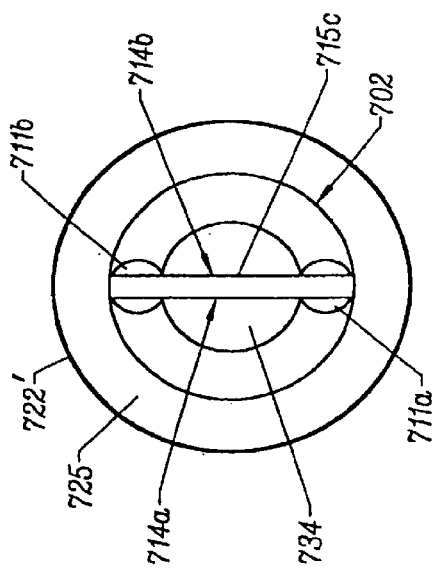

FIGS. 39A–B schematically represent a process during treatment of a patient with electrosurgical probe 700. Blade active electrode 712 is affixed to support 710 on shaft 702. Blade active electrode 712 includes active edge 713 and first and second blade sides, 714a, 714b (e.g., FIGS. 31A–B). Referring to FIG. 39A, active edge 713 forms an incision, I, in a target tissue, T, via localized molecular dissociation of tissue components upon application of a high frequency voltage between active electrode 712 and return electrode 718. (The localized molecular dissociation may be facilitated by the delivery of a suitable quantity of an electrically conductive fluid (e.g. isotonic saline) to form a current flow path between active electrode 712 and return electrode 718.) With reference to FIG. 39B, as the incision I is deepened within tissue T, first and second blade sides, 714a, 714b engage severed tissue in regions indicated by the arrows labeled E. In this way, the severed tissue is coagulated by first and second blade sides, 714a, 714b, thereby effecting hemostasis at the point of incision of the tissue.

Figure 40A:
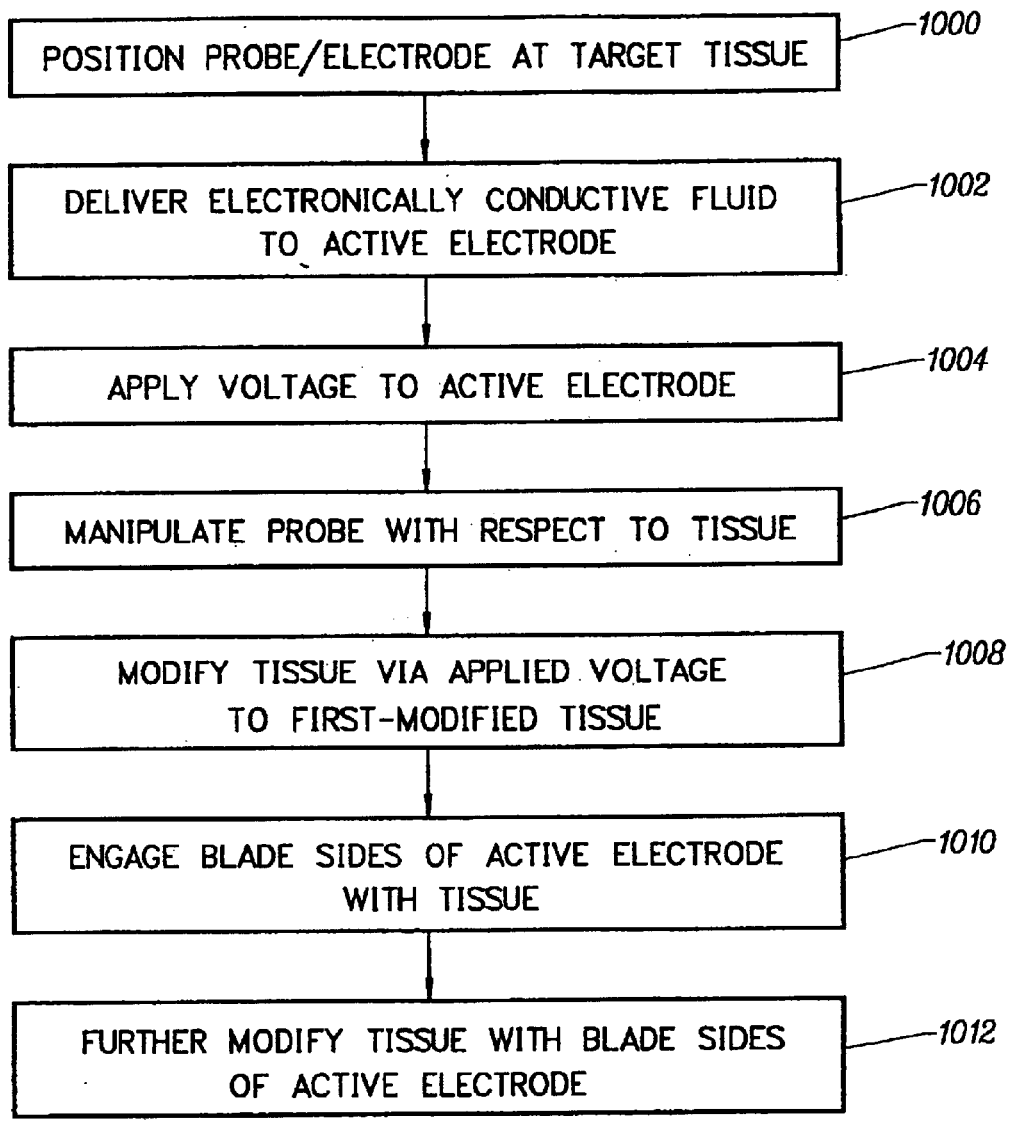
FIG. 40A schematically represents a number of steps involved in a method of treating a patient with an electrosurgical probe having a blade electrode, according to one embodiment of the invention.

FIG. 40A schematically represents a number of steps involved in a method of treating a patient with an electrosurgical probe, wherein step 1000 involves positioning the distal end of the probe adjacent to target tissue such that an active electrode of the probe is in contact with or in close proximity to the target tissue. In one embodiment, the active electrode is spaced a short distance from the target tissue, as described hereinabove. In embodiments involving use of a probe having a blade active electrode, step 1000 typically involves positioning the probe such that the active edge of the active electrode makes contact with, or is in close proximity to, the target tissue.

Step 1002 involves delivering an electrically conductive fluid to the distal end of the probe in the vicinity of the active electrode and the return electrode, such that the electrically conductive fluid forms a current flow path between the active electrode and the return electrode. The electrically conductive fluid may be delivered via an exterior tube disposed on the outside of the shaft (e.g., FIGS. 37A, 37B), or an outer sheath external to the shaft and forming an annular fluid delivery lumen (e.g., FIGS. 38A, 38B). Alternatively, an electrically conductive fluid, such as a gel, may be placed between the active electrode and the return electrode prior to step 1000. The electrically conductive fluid may be a liquid, a gel, or a gas. Apart from providing an efficient current flow path between the active and return electrodes, a clear, colorless electrically conductive liquid, such as isotonic saline, exhibits the added advantage of increasing the visibility of the surgeon at the target site. However, in situations where there is an abundance of electrically conductive body fluids (e.g., blood) already present at the target site, step 1002 may optionally be omitted.

Step 1004 involves applying a high frequency voltage difference between the active electrode and the return electrode sufficient to ablate or otherwise modify the target tissue via localized molecular dissociation of target tissue components. By delivering an appropriate high frequency voltage to a suitably configured probe, the target tissue can be incised, dissected, transected, contracted, or otherwise modified. In addition, the modified tissue can also be coagulated (e.g., FIG. 39A). The frequency of the applied voltage will generally be within the ranges cited hereinabove. For example, the frequency will typically range from about 5 kHz to 20 MHz, usually from about 30 kHz to 2.5 MHz, and often between about 100 kHz and 200 kHz. The root mean square (RMS) voltage that is applied in step 1004 is generally in the range of from about 5 volts to 1000 volts RMS, more typically being in the range of from about 10 volts to 500 volts RMS. The actual voltage applied may depend on a number of factors, including the size of the active electrode, the operating frequency, and the particular procedure or desired type of modification of the tissue (incision, contraction, etc.), as described hereinabove.

Step 1006 involves manipulating the probe with respect to the tissue at the target site. For example, the probe may be manipulated such that the active electrode reciprocates with respect to the target tissue, such that the target tissue is severed, incised, or transected at the point of movement of the active edge by a process involving molecular dissociation of tissue components. In one embodiment, step 1006 involves reciprocating the active edge of a blade active electrode in a direction parallel to a surface of the target tissue. During at least a portion of step 1006, one or more parts of the active electrode, e.g., an active edge, may be engaged against the target tissue. Typically, step 1006 is performed concurrently with step 1004. Step 1002 may be performed at any stage during the procedure, and the rate of delivery of the electrically conductive fluid may be regulated by a suitable mechanism, such as a valve.

Step 1008 involves modifying the target tissue as a result of the high frequency voltage applied in step 1004. The target tissue may be modified in a variety of different ways, as referred to hereinabove. The type of tissue modification achieved depends, inter alia, on the voltage parameters of step 1004; the shape, size, and composition of the active electrode; and the manner in which the probe is manipulated by the surgeon in step 1006. At relatively high voltage levels, tissue components typically undergo localized molecular dissociation, whereby the target tissue can be dissected, incised, transected, etc. At a lower voltage, or at a lower current density on the active electrode surface, the target tissue can be contracted (e.g., by shrinkage of collagen fibers in the tissue), or a blood vessel can be coagulated. For example, in step 1010, first and second blade sides of the active electrode may be engaged against a region of the target tissue which has been modified as a result of localized molecular dissociation of tissue components in step 1008. In one embodiment, the first and second blade sides are substantially flat metal plates having lower current densities than the active edge. In this manner, the lower current densities of the first and second blade sides cause coagulation of the previously modified (e.g., severed) target tissue (step 1012).

Figure 40B:
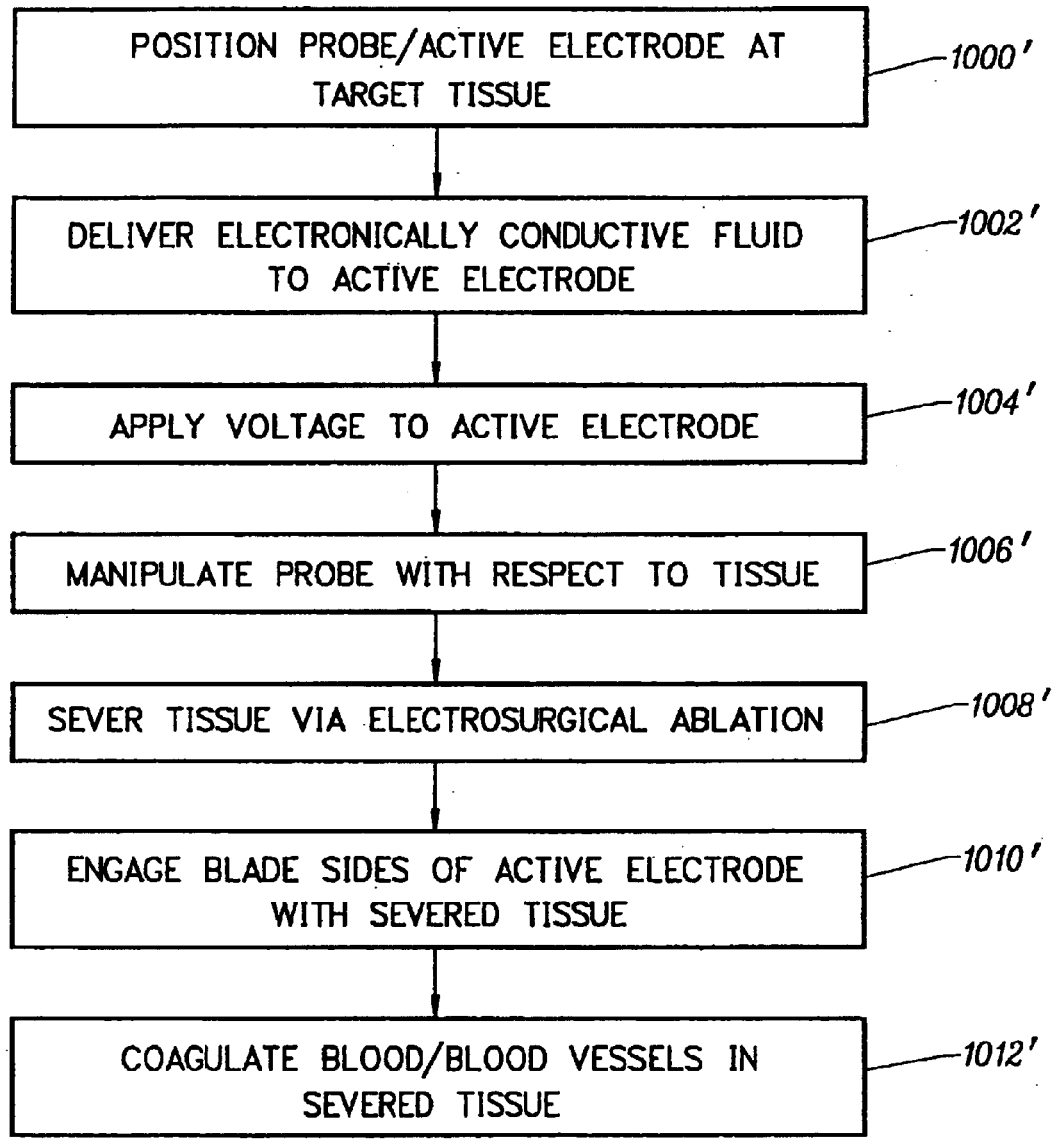
FIG. 40B schematically represents a number of steps involved in a method of concurrently severing and coagulating tissue, according to one embodiment of the invention.

FIG. 40B schematically represents a number of steps involved in a method of severing tissue with an electrosurgical probe via a process involving molecular dissociation of tissue components, and of coagulating the severed tissue with the same electrosurgical probe during a single procedure, according to another aspect of the invention. In one embodiment, the electrosurgical probe comprises a single blade active electrode in the form of a substantially flat metal blade having an active edge adapted for electrosurgically severing the tissue, and first and second blade sides adapted for effecting hemostasis of the severed tissue. Steps 1000' through 1006' are substantially the same or analogous to steps 1000 through 1006, as described hereinabove with reference to FIG. 40A. Step 1008' involves severing the target tissue via localized molecular dissociation of tissue components due to high current densities generated at the position of the active edge upon execution of step 1004'. Step 1010' involves engaging the first and second blade sides against the tissue severed in step 1008', whereby blood/blood vessels in the severed tissue are coagulated as a result of the relatively low current densities on the first and second blade sides (step 1012').

Figure 41:
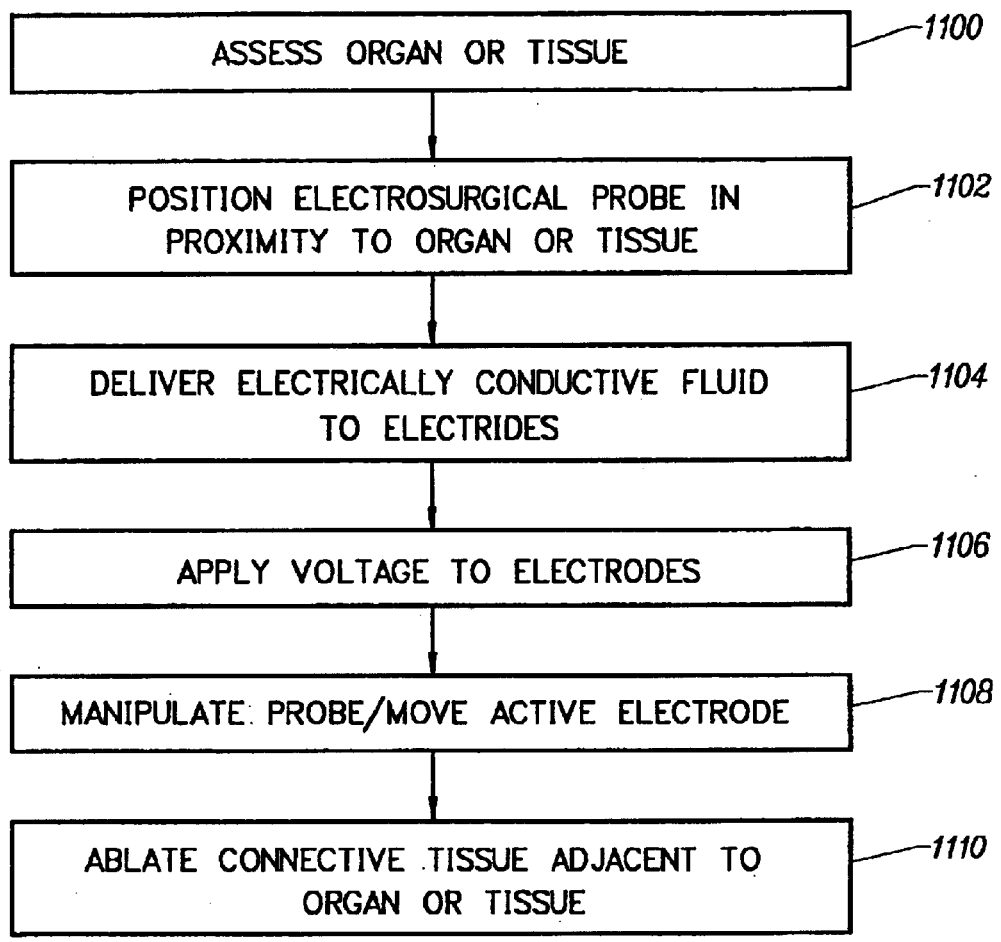
FIG. 41 schematically represents a number of steps involved in a method of dissecting a tissue or organ of a patient with an electrosurgical probe, according to another embodiment of the invention.

FIG. 41 schematically represents a number of steps involved in a method of dissecting a tissue or organ of a patient with an electrosurgical probe, according to one embodiment of the invention, wherein step 1100 involves accessing an organ or tissue. Typically, accessing an organ or tissue in step 1100 involves removing or incising at least a portion of an overlying tissue which conceals the organ or tissue to be dissected. As an example, in a minimally invasive intercostal procedure, an internal mammary artery may be accessed by making an electrosurgical incision through the intercostal space. An introducer device (e.g., a hollow needle or a cannula) may be inserted in the incision. The distal end of an electrosurgical probe may be passed through the introducer device to allow the probe distal end to be brought in close proximity to the internal mammary artery. Forming an incision in the intercostal space may be performed generally according to methods described hereinabove, e.g., with reference to FIG. 40A or 40B. In another example, in an open chest procedure involving a median sternotomy, the internal mammary artery may be accessed after first making a longitudinal incision through the sternum. Incising the sternum in step 1100 may be performed generally according to methods described with reference to FIG. 40A or 40B.

Step 1102 involves positioning the distal end of the electrosurgical probe, and in particular the active electrode, in at least close proximity to connective tissue adjacent to the tissue or organ to be dissected. As an example, the connective tissue may be soft tissue, such as adipose tissue, or relatively hard tissue such as cartilage or bone. In one embodiment, the active electrode comprises a blade active electrode having an active edge. Optional step 1104 involves delivering an electrically conductive fluid to the distal end of the probe such that the electrically conductive fluid forms a current flow path between the active electrode and a return electrode, generally as described for step 1002, supra. Step 1106 involves applying a high frequency voltage between the active electrode and the return electrode, generally as described for step 1004, supra.

Depending on the type of procedure, e.g., the nature of the tissue or organ to be dissected, optional step 1108 may be performed, in which the probe is manipulated such that the active electrode is moved with respect to the connective tissue adjacent to the tissue or organ to be dissected. Step 1110 involves electrosurgically ablating, via molecular dissociation of connective tissue components, at least a portion of the connective tissue adjacent to the tissue or organ to be dissected. As an example, connective tissue adjacent to the internal mammary artery may be dissected by a process involving molecular dissociation of connective tissue components, in either an open-chest or a minimally invasive procedure, such that the IMA is substantially free from connective tissue over a portion of its distal length or completely if needed as a free graft. Subsequently, such a portion of the IMA may be used to provide a graft vessel during a CABG procedure, the latter well known in the art.

Figure 42:
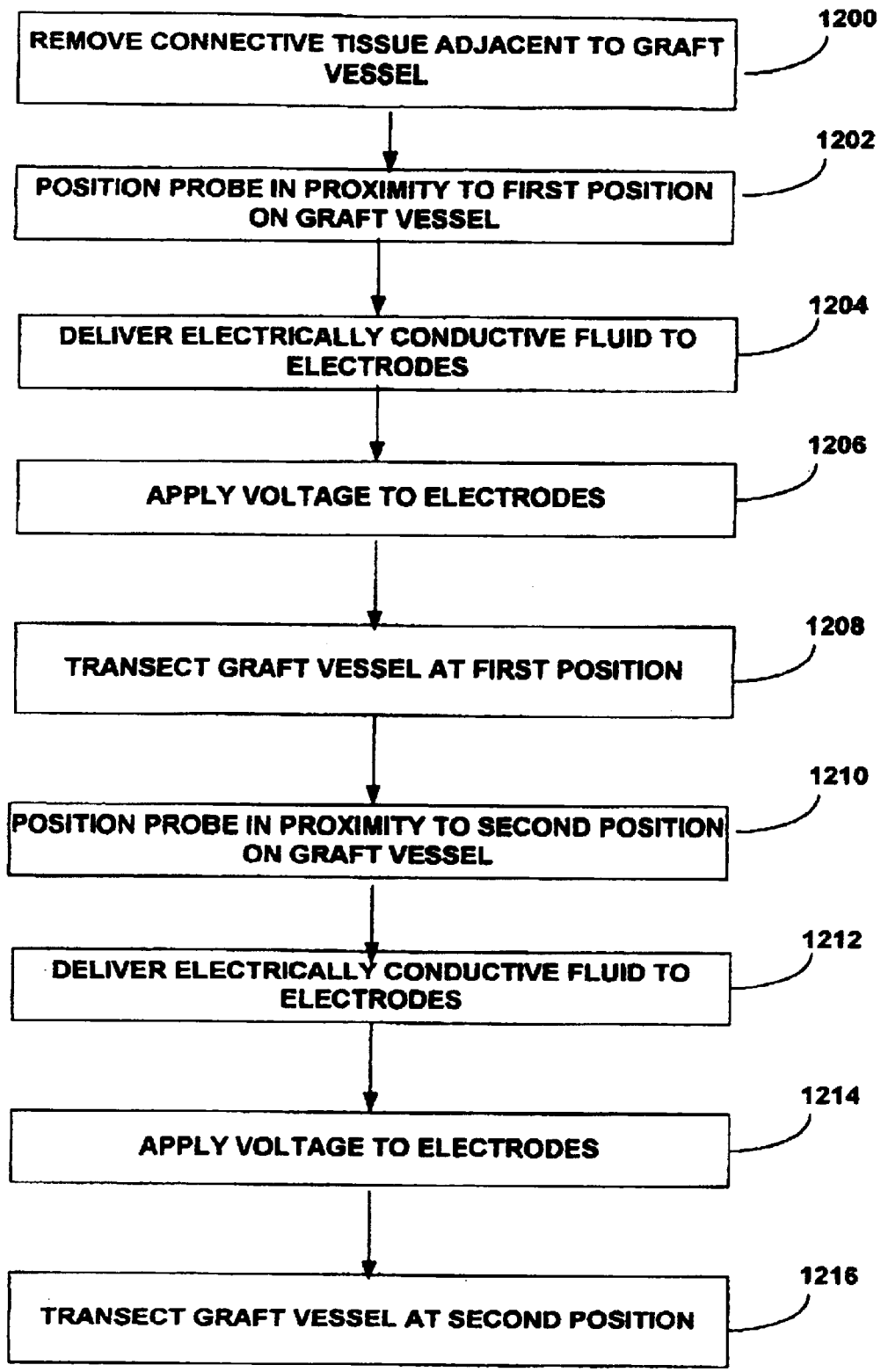
FIG. 42 schematically represents a number of steps involved in a method of providing a graft blood vessel for a patient, according to a further embodiment of the invention.
Figure 43:
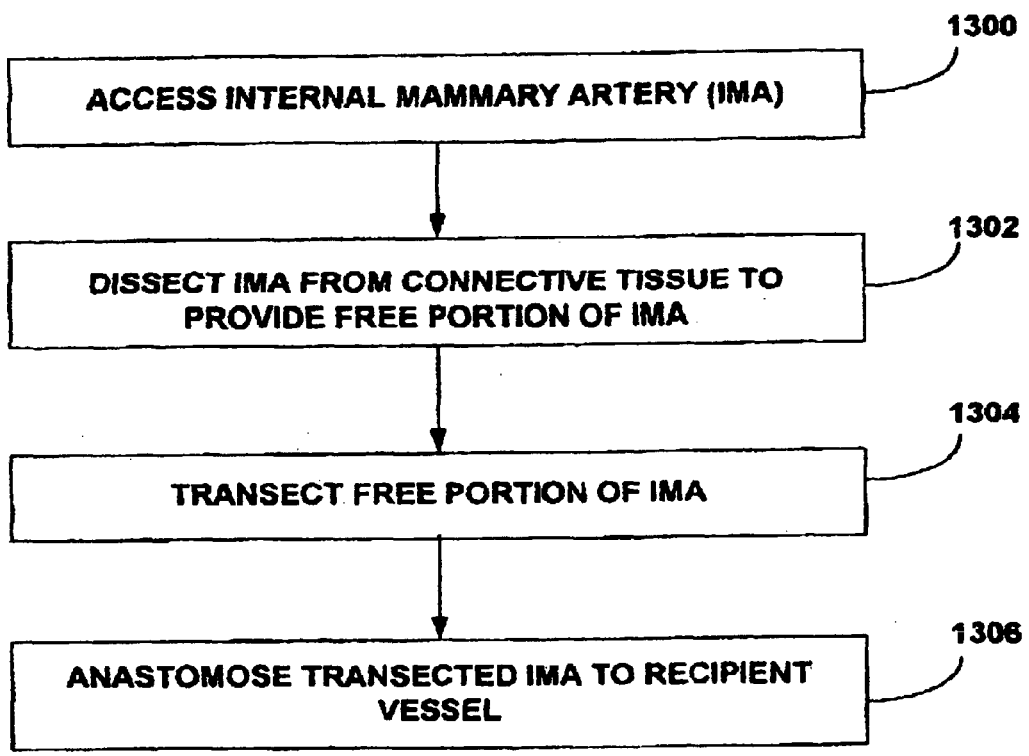
FIG. 43 schematically represents a number of steps involved in a method of harvesting an internal mammary artery of a patient, according to a further embodiment of the invention.

FIG. 42 schematically represents a number of steps involved in a method of providing a graft blood vessel for a patient, according to the invention, wherein step 1200 involves removing at least a portion of the connective tissue adjacent to a graft vessel. As an example, the graft vessel may be the saphenous vein (of the leg) or the left or right IMA. In one embodiment, step 1200 may be performed generally according to steps 1100 through 1110 outlined hereinabove with reference to FIG. 41. Step 1202 involves positioning the distal end of an electrosurgical probe such that at least one active electrode is in contact with, or close proximity to, the graft vessel at a first position at which the graft vessel is to be transected. As an example, an introducer device (e.g., a hollow needle or a cannula) may be inserted through an incision in an intercostal space, and the distal end of the electrosurgical probe may be passed through the introducer device to allow the probe distal end to be brought in close proximity to an IMA at the first position targeted for transection. In one embodiment, the at least one active electrode comprises a blade electrode having an active edge and first and second blade sides. Step 1204 involves delivering an electrically conductive fluid to the distal end of the probe such that a current flow path is provided between the active electrode and the return electrode, generally as for step 1002 (FIG. 40A). Step 1206 involves applying a high frequency voltage difference between the active and return electrodes, generally as for step 1004, supra. Typically, step 1206 results in the generation of high current densities in the vicinity of certain portions of the active electrode(s), sufficient to cause localized ablation of graft vessel tissue via molecular dissociation of tissue components at the first position, whereby the graft vessel is transected at the first position (step 1208). Optionally, during step 1206 the probe may be manipulated such that the active electrode is moved with respect to the graft vessel at the first position. Transection of the graft vessel at the first position provides a pedicled graft, e.g., an IMA graft suitable for use in a single anastomosis CABG procedure.f a free graft is required during a procedure, the graft vessel (e.g., the saphenous vein) may be transected at a second position according to steps 1210 through 1216, wherein step 1210 involves positioning the distal end of the probe such that the active electrode is in contact with, or close proximity to, the graft vessel at the second position at which the graft vessel is to be transected. Step 1212 involves delivering an electrically conductive fluid to the distal end of the probe, essentially as for step 1204. Step 1214 involves applying a high frequency voltage between the active electrode and the return electrode. The applied voltage is sufficient to transect the graft vessel at the second position (step 1216) via molecular dissociation of tissue components. The free graft thus provided may be conveniently used in a double anastomosis CABG procedure. FIG. 43 schematically represents a number of steps involved in a method of harvesting an internal mammary artery of a patient, according to another embodiment of the invention, wherein step 1300 involves accessing an IMA. The IMA may be accessed and harvested either in an open procedure (median sternotomy) or in a minimally invasive (intercostal) procedure, as described hereinabove. In either case, overlying tissue, e.g., the sternum or the intercostal space may be removed by an electrosurgical process involving molecular dissociation of tissue components, e.g., as described with reference to FIG. 401B. Step 1302 involves dissecting the IMA from connective tissue which at least partially surrounds the IMA, to provide a free portion of the IMA. For example, step 1302 may be performed essentially as described for steps 1102 through 1110 with reference to FIG. 41. Step 1304 involves transecting the IMA to provide a pedicled graft of the IMA suitable for use in a single anastomosis CABG procedure. As an example, the IMA may be transected essentially as described for steps 1202 through 1208 with reference to FIG. 42. By positioning a tip or edge of the active electrode in at least close proximity to the IMA while avoiding contact between the IMA and one or more sides of the active electrode, the IMA may be transected without coagulating the IMA. Step 1306 involves anastomosing the IMA graft provided in step 1304 to a recipient blood vessel, such as a coronary artery. Typically, step 1306 involves an end-to-side anastomosis in which the transected end of the free portion of the IMA is anastomosed to a side of a coronary artery. In one embodiment, the free IMA graft vessel is anastomosed to the side of the ascending aorta. Step 1306 may involve forming an incision or opening in the wall of the recipient vessel, via electrosurgical molecular dissociation of tissue components of the recipient vessel, wherein the incision or opening is suitable for accommodating the transected end of the IMA. Such an incision may be formed, with minimal or no collateral tissue damage, by application of a suitable high frequency voltage to a bipolar electrosurgical probe in the presence of an electrically conductive fluid. Details for the precise and controlled removal of tissue via electrosurgical molecular dissociation, according to the instant invention, are provided hereinabove.

It is to be understood that the methods described hereinabove for dissecting, transecting, and harvesting tissues and organs, such as graft blood vessels, are by no means limited to apparatus having a blade-like active electrode; various electrosurgical probes having a range of electrode configurations and adapted for cool ablation of tissue via molecular dissociation of tissue components may be used in such procedures. Thus, while the exemplary embodiments of the present invention have been described in detail, by way of example and for clarity of understanding, a variety of changes, adaptations, and modifications will be apparent to those of skill in the art. Therefore, the scope of the present invention is limited solely by the appended claims.

What is claimed is:

1. A method of providing a graft vessel for a patient, comprising:
   a) dissecting the graft vessel from connective tissue adjacent to the graft vessel to provide a free portion of the graft vessel;
   b) positioning an active electrode of an electrosurgical probe in at least close proximity to a first position of the free portion of the graft vessel; and thereafter
   c) upon application of a high frequency voltage between the active electrode and a return electrode, transecting the graft vessel at the first position via localized molecular dissociation of graft vessel components.

2. The method of claim 1, further comprising:

d) positioning the active electrode of the electrosurgical probe in at least close proximity to a second position of the free portion of the graft vessel; and thereafter e) upon application of a high frequency voltage between the active electrode and the return electrode, transecting the graft vessel at the second position via localized molecular dissociation of the graft vessel components.

3. The method of claim 2, further comprising:

f) prior or concurrently to said steps c) or e), delivering an electrically conductive fluid to the active electrode such that the electrically conductive fluid provides a current flow path between the active electrode and the return electrode.

4. The method of claim 2, wherein transecting the graft vessel at the first position or the second position comprises moving the active electrode with respect to the graft vessel.

5. The method of claim 1, further comprising:

g) prior to said step a), accessing at least a portion of the graft vessel by removing at least a portion of an overlying tissue which overlies the graft vessel.

6. The method of claim 5, wherein said step g) comprises:

h) positioning the active electrode in at least close proximity to the overlying tissue; and i) after said step h), applying a high frequency voltage between the active electrode and the return electrode, wherein the overlying tissue is ablated via localized molecular dissociation of overlying tissue components.

7. The method of claim 6, further comprising:

j) prior to or during said step i), delivering an electrically conductive fluid to the active electrode such that the electrically conductive fluid provides a current flow path between the active electrode and the return electrode.

8. The method of claim 6, further comprising:

k) during said step i), moving the active electrode against a surface of the overlying tissue to create an incision in the overlying tissue.

9. The method of claim 8, further comprising effecting hemostasis of the overlying tissue at the incision.

10. The method of claim 6, wherein the active electrode consists essentially of a single blade electrode having an active edge and first and second blade sides, the overlying tissue comprises the sternum, said step i) generates a high current density in the region of the active edge such that an incision is formed in the sternum, and at least one of the first and second blade sides engages the incised sternum, wherein hemostasis of the incised sternum is effected.

11. The method of claim 5, wherein the overlying tissue is a sternum, an intercostal space, or the skin of the patient.

12. The method of claim 1, wherein said step a) comprises:

l) positioning the active electrode of the electrosurgical probe in at least close proximity to the connective tissue adjacent to the graft vessel; and m) after said step l), applying a high frequency voltage between the active electrode and the return electrode, wherein at least a portion of the connective tissue adjacent to the graft vessel is ablated via localized molecular dissociation of connective tissue components.

13. The method of claim 12, further comprising:

n) prior to or during said step m), providing an electrically conductive fluid between the active electrode and the return electrode.

14. The method of claim 12, wherein during said steps c) and m) the graft vessel and the connective tissue, respectively, are exposed to a temperature in the range of from about 40° C. to 70° C.

15. The method of claim 12, wherein said step m) comprises effecting hemostasis of the connective tissue.

16. The method of claim 1, wherein said steps a) through c) are performed in a minimally invasive procedure or with laparascopic access.

17. The method of claim 1, wherein the method is performed intercostally.

18. The method of claim 1, wherein the method comprises a coronary artery bypass graft (CABG) procedure.

19. The method of claim 1, wherein said steps a) through c) are performed in conjunction with a median sternotomy.

20. The method of claim 1, wherein the graft vessel is a saphenous vein or an internal mammary artery.

21. The method of claim 1, wherein the high frequency voltage has a frequency in the range of from about 50 kHz to about 500 kHz.

22. The method of claim 1, wherein the high frequency voltage is in the range of from about 10 volts RMS to about 500 volts RMS.

23. The method of claim 1, wherein the active electrode consists essentially of a single blade electrode having an active edge and first and second blade sides.

* * * * *